United States Patent
Üren et al.

(10) Patent No.: US 11,202,792 B2
(45) Date of Patent: Dec. 21, 2021

(54) CD99 INHIBITORS AND THEIR USES

(71) Applicant: GEORGETOWN UNIVERSITY, Washington, DC (US)

(72) Inventors: Aykut Üren, Rockville, MD (US); Haydar Celik, Potomac, MD (US); Jeffrey A. Toretsky, Silver Spring, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 16/340,831

(22) PCT Filed: Oct. 12, 2017

(86) PCT No.: PCT/US2017/056348
§ 371 (c)(1),
(2) Date: Apr. 10, 2019

(87) PCT Pub. No.: WO2018/071675
PCT Pub. Date: Apr. 19, 2018

(65) Prior Publication Data
US 2019/0262370 A1  Aug. 29, 2019

Related U.S. Application Data

(60) Provisional application No. 62/407,116, filed on Oct. 12, 2016.

(51) Int. Cl.
| | |
|---|---|
| A61K 31/7076 | (2006.01) |
| A61P 37/06 | (2006.01) |
| A61P 35/00 | (2006.01) |
| A61K 9/00 | (2006.01) |
| A61K 31/506 | (2006.01) |
| A61K 45/06 | (2006.01) |

(52) U.S. Cl.
CPC ........ *A61K 31/7076* (2013.01); *A61K 9/0019* (2013.01); *A61K 31/506* (2013.01); *A61K 45/06* (2013.01); *A61P 35/00* (2018.01); *A61P 37/06* (2018.01)

(58) Field of Classification Search
CPC .............. A61K 31/7076; A61K 9/0019; A61K 31/506; A61K 45/06; A61K 2300/00; A61P 35/00; A61P 37/06
See application file for complete search history.

(56) References Cited

U.S. PATENT DOCUMENTS

| | | | | |
|---|---|---|---|---|
| 7,772,206 B2* | 8/2010 | Wood | ............ | A61K 31/34 514/46 |
| 8,263,575 B2* | 9/2012 | McGuigan | ............ | C07H 19/20 514/47 |
| 9,757,380 B2* | 9/2017 | Xu | ............ | A61K 31/355 |
| 9,956,176 B2* | 5/2018 | Nagy | ............ | A61K 9/0043 |
| 10,369,104 B2* | 8/2019 | Nagy | ............ | A61K 31/713 |
| 2008/0262003 A1 | 10/2008 | Xu | | |
| 2009/0155211 A1 | 6/2009 | Wood et al. | | |
| 2009/0215715 A1 | 8/2009 | Mcguigan et al. | | |

FOREIGN PATENT DOCUMENTS

| | | |
|---|---|---|
| WO | 2015153805 A2 | 10/2015 |
| WO | 2018071675 A1 | 4/2018 |

OTHER PUBLICATIONS

"Ciofarabine-5'-triphosphate", Jena Bioscience, Retrieved from the Internet http://www.jenabioscience.com/images/PDF/NU-OXEL008. pdf on Dec. 19, 2017, Feb. 26, 2015, 1 page.
Ambros et al., "MIC2 is a Specific Marker for Ewing's Sarcoma and Peripheral Primitive Neuroectodermal Tumors. Evidence for a Common Histogenesis of Ewing's Sarcoma and Peripheral Primitive Neuroectodermal Tumors From MIC2 Expression and Specific Chromosome Aberration", Cancer, vol. 67, No. 7, Apr. 1, 1991, pp. 1886-1893.
Arndt et al., "Common Musculoskeletal Tumors of Childhood and Adolescence", The New England Journal of Medicine, vol. 341, Jul. 29, 1999, pp. 342-352.
Aubrit et al., "The Biochemical Characterization of E2, a T Cell Surface Molecule Involved in Rosettes", European Journal of Immunology, vol. 19, No. 8, Aug. 1989, pp. 1431-1436.
Bernard et al., "A T Cell Surface Molecule Different From CD2 is Involved in Spontaneous Rosette Formation With Erythrocytes", J Immunol., vol. 140, No. 6, Mar. 15, 1988, pp. 1802-1807.
Bixel et al., "Mouse CD99 Participates in T-Cell Recruitment Into Inflamed Skin", Blood, vol. 104, No. 10, Nov. 15, 2004, pp. 3205-3213.

(Continued)

*Primary Examiner* — Lawrence E Crane
(74) *Attorney, Agent, or Firm* — Kilpatrick Townsend & Stockton LLP

(57) ABSTRACT

Provided herein are methods of treating a bone or connective tissue cancer in a subject. The methods comprise administering to the subject an effective amount of a CD99 inhibitor, wherein the CD99 inhibitor is a compound having the formula

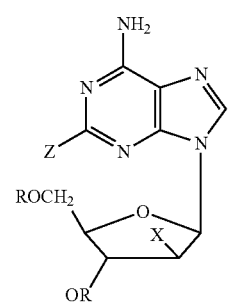

wherein R, each of which may be the same or different, is hydrogen, or a protecting group; wherein Z is selected from the group consisting of F, Cl and Br; wherein X is H or F; and pharmaceutically acceptable salts thereof.

8 Claims, 41 Drawing Sheets

Specification includes a Sequence Listing.

(56) References Cited

OTHER PUBLICATIONS

Bonate et al., "Discovery and Development of Clofarabine: A Nucleoside Analogue for Treating Cancer", Nature Reviews Drug Discovery, vol. 5, No. 10, Oct. 2006, pp. 855-863.
Brohl et al., "The Genomic Landscape of the Ewing Sarcoma Family of Tumors Reveals Recurrent STAG2 Mutation", PLoS Genet., vol. 10, No. 7, Jul. 10, 2014, 13 pages.
Celik et al., "Abstract 1933: Discovery of First-in-Class Small Molecule CD99 Inhibitors for Targeted Therapy of Ewing Sarcoma", Proceedings of the American Association for Cancer Research Annual Meeting 2017, Cancer Research, vol. 77, Issue 13, Jul. 1, 2017, 1 page.
Celik et al., "Clofarabine Inhibits Ewing Sarcoma Growth Through a Novel Molecular Mechanism Involving Direct Binding to CD99", Oncogene, vol. 37, No. 16, Jan. 31, 2018, pp. 2181-2196.
Celik et al., "Ezrin Binds to DEAD-Box RNA Helicase DDX3 and Regulates Its Function and Protein Level", Mol Cell Biol., vol. 35, No. 18, Sep. 2015, pp. 3145-3162.
Choi et al., "Detection of Homodimer Formation of CD99 Through Extracelluar Domain Using Bimolecular Fluorescence Complementation Analysis", Experimental & Molecular Medicine, vol. 39, No. 6, Dec. 2007, pp. 746-755.
Chung et al., "CD99 Is a Therapeutic Target on Disease Initiating Stem Cells in Acute Myeloid Leukemia and the Myelodysplastic Syndromes", Blood, vol. 124, No. 21, 2014, p. 3760.
Chung et al., "CD99 Is a Therapeutic Target On Disease Stem Cells In Acute Myeloid Leukemia and The Myelodysplastic Syndromes", Blood, vol. 122, No. 21, 2013, 1 page.
Chung et al., "CD99 is a Therapeutic Target on Disease Stem Cells in Myeloid Malignancies", Science Translational Medicine, vol. 9, No. 374, Jan. 25, 2017, 27 pages.
Cox et al., "Investigating CD99 Expression in Leukemia Propagating Cells in Childhood T Cell Acute Lymphoblastic Leukemia", PLoS One., vol. 11, No. 10, Oct. 20, 2016, 13 pages.
Davies et al., "Mutations of the BRAF Gene in Human Cancer", Nature, vol. 417, No. 6892, Jun. 27, 2002, pp. 949-954.
Dworzak et al., "CD99 (MIC2) Expression in Paediatric B-Lineage Leukaemia/Lymphoma Reflects Maturation-associated Patterns of Normal B-Lymphopoiesis", Br. J. Haematol., vol. 105, No. 3, Jun. 1999, pp. 690-695.
Dworzak et al., "Flow Cytometric Assessment of Human MIC2 Expression in Bone Marrow, Thymus, and Peripheral Blood", Blood, vol. 83, No. 2, Jan. 15, 1994, pp. 415-425.
Ellis et al., "PBDX is the XG Blood Group Gene", Nature Genetics, vol. 8, No. 3, Nov. 1, 1994, pp. 285-290.
Fellinger et al., "Immunohistochemical Analysis of Ewing's Sarcoma Cell Surface Antigen p30/32MIC2", Am. J. Pathol., vol. 139, No. 2, Aug. 1991, pp. 317-325.
Franzetti et al., "MiR-30a-5p Connects EWS-FLI1 and CD99, Two Major Therapeutic Targets in Ewing Tumor", Oncogene, vol. 32, No. 33, Aug. 15, 2013, pp. 3915-3921.
Gaspar et al., "Ewing Sarcoma: Current Management and Future Approaches Through Collaboration", Journal of Clinical Oncology, vol. 33, No. 27, Sep. 20, 2015, pp. 3036-3046.
Gelin et al., "The E2 Antigen, a 32 kd Glycoprotein Involved in T-cell Adhesion Processes, is the MIC2 Gene Product", EMBO J., vol. 8, No. 11, Nov. 1, 1989, pp. 3253-3259.
Gellini et al., "Generation of Human Single-Chain Antibody to the CD99 Cell Surface Determinant Specifically Recognizing Ewing's Sarcoma Tumor Cells", Current Pharmaceutical Biotechnology, vol. 14, No. 4, 2013, pp. 449-463.
Giovannoni et al., "A Placebo-Controlled Trial of Oral Cladribine for Relapsing Multiple Sclerosis", N. Engl. J. Med., vol. 362, No. 5, Feb. 4, 2010, pp. 416-426.
Gollnest et al., "Lipophilic Prodrugs of Nucleoside Triphosphates as Biochemical Probes and Potential Antivirals", Nature Communications, vol. 6, Article No. 8716, Oct. 27, 2015, 15 pages.

Gollnest et al., "Membrane-Permeable Triphosphate Prodrugs of Nucleoside Analogues", Angewandte Chemie, vol. 55, No. 17, Apr. 18, 2016, pp. 5255-5258.
Guerzoni et al., "CD99 Triggering in Ewing Sarcoma Delivers a Lethal Signal through p53 Pathway Reactivation and Cooperates with Doxorubicin", Clin Cancer Res., vol. 21, No. 1, Jan. 1, 2015, pp. 146-156.
Halliday et al., "Diagnostic Utility of MIC-2 Immunocytochemical Staining in the Differential Diagnosis of Small Blue Cell Tumors", Diagn. Cytopathol., vol. 19, No. 6, Dec. 1998, pp. 410-416.
Hu-Lieskovan et al., "EWS-FLI1 Fusion Protein Up-regulates Critical Genes in Neural Crest Development and is Responsible for the Observed Phenotype of Ewing's Family of Tumors", Cancer Research, vol. 65, No. 11, Jun. 1, 2005, pp. 4633-4644.
Husak et al., "CD99 Ligation Upregulates HSP70 on Acute Lymphoblastic Leukemia Cells and Concomitantly Increases NK Cytotoxicity", Cell Death & Disease, vol. 3, Nov. 15, 2012, 6 pages.
Husak et al., "Death Induction by CD99 Ligation in TEL/AML1-Positive Acute Lymphoblastic Leukemia and Normal B Cell Precursors", Journal of Leukocyte Biology, vol. 88, No. 2, Aug. 2010, pp. 405-412.
Kawasaki et al., "Relationship of Deoxycytidine Kinase and Cytoplasmic 5'-Nucleotidase to the Chemotherapeutic Efficacy of 2-Chlorodeoxyadenosine", Blood, vol. 81, No. 3, Feb. 1, 1993, pp. 597-601.
Khoury, "Ewing Sarcoma Family of Tumors", Advances in Anatomic Pathology, vol. 12, No. 4, Jul. 2005, pp. 212-220.
Kim et al., "Identification of Cyclophilin A as a CD99-binding Protein by Yeast Two-Hybrid Screening", Immunology Letters, vol. 95, No. 2, Sep. 2004, pp. 155-159.
Kovar, "Ewing's Sarcoma and Peripheral Primitive Neuroectodermal Tumors After Their Genetic Union", Current Opinion in Oncology, vol. 10, No. 4, Jul. 1998, pp. 334-342.
Kovar et al., "Overexpression of the Pseudoautosomal Gene MIC2 in Ewing's Sarcoma and Peripheral Primitive Neuroectodermal Tumor", Oncogene, vol. 5, No. 7, Jul. 1990, pp. 1067-1070.
Kovar et al., "The Second European Interdisciplinary Ewing Sarcoma Research Summit—A Joint Effort to Deconstructing the Multiple Layers of a Complex Disease", Oncotarget, vol. 7, No. 8, Feb. 23, 2016, pp. 8613-8624.
Kreppel et al., "Suppression of KCMF1 by Constitutive High CD99 Expression is Involved in the Migratory Ability of Ewing's Sarcoma Cells", Oncogene, vol. 25, No. 19, May 4, 2006, pp. 2795-2800.
Lawlor et al., "Twenty Years On: What Do We Really Know About Ewing Sarcoma and What is the Path Forward?", Critical Reviews™ in Oncogenesis, vol. 20, Nos. 3-4, Sep. 2015, pp. 155-171.
Lee et al., "Analysis of the Dimerization of Human CD99 Using Bimolecular Fluorescence Complementation Technique", J Microbiol Biotechnol., vol. 18, No. 3, Mar. 2008, pp. 472-476.
Lee et al., "EWS/FLI-1 Fusion Transcript Detection and MIC2 Immunohistochemical Staining in the Diagnosis of Ewing's Sarcoma", Pediatric Pathology & Laboratory Medicine, vol. 16, No. 3, May-Jun. 1996, pp. 379-392.
Longhi et al., "Late Effects of Chemotherapy and Radiotherapy in Osteosarcoma and Ewing Sarcoma Patients", Cancer, vol. 118, No. 20, Oct. 15, 2012, pp. 5050-5059.
Lucas et al., "Ewing Sarcoma vs Lymphoblastic Lymphoma: A Comparative Immunohistochemical Study", American Journal of Clinical Pathology, vol. 115, No. 1, Jan. 1, 2001, pp. 11-17.
Manara et al., "CD99 Acts as an Oncosuppressor in Osteosarcoma", Molecular Biology of the Cell, vol. 17, No. 4, Apr. 1, 2006, pp. 1910-1921.
Miyagawa et al., "Inducible Expression of Chimeric Ews/ets Proteins Confers Ewing's Family Tumor-like Phenotypes to Human Mesenchymal Progenitor Cells", Mol. Cell. Biol., vol. 28, No. 7, Apr. 2008, pp. 2125-2137.
Moricoli et al., "Process Development of a Human Recombinant Diabody Expressed in *E. coli*: Engagement of CD99-Induced Apoptosis for Target Therapy in Ewing's Sarcoma", Applied Microbiology and Biotechnology, vol. 100, No. 9, May 2016, pp. 3949-3963.
International Application No. PCT/US2017/056348 , "International Preliminary Report on Patentability", dated Apr. 25, 2019, 7 pages.

(56) References Cited

OTHER PUBLICATIONS

International Application No. PCT/US2017/056348, "International Search Report and Written Opinion", dated Jan. 4, 2018, 10 pages.
Perlman et al., "Ewing's Sarcoma—Routine Diagnostic Utilization of MIC2 Analysis: A Pediatric Oncology Group/children's Cancer Group Intergroup Study", Human Pathology, vol. 25, No. 3, Mar. 1994, pp. 304-307.
Rocchi et al., "CD99 Inhibits Neural Differentiation of Human Ewing Sarcoma Cells and Thereby Contributes to Oncogenesis", The Journal of Clinical Investigation, vol. 120, No. 3, Mar. 1, 2010, pp. 668-680.
Schenkel et al., "CD99 Plays a Major Role in the Migration of Monocytes Through Endothelial Junctions", Nature Immunology, vol. 3, No. 3, Feb. 2002, pp. 143-150.
SCHLEYER, "Charmm: the Energy Function and Its Parameterization", Encyclopedia of Computational Chemistry, vol. 1, No. A-D, 1998, pp. 271-277.
Schneider et al., "NIH Image to Imagej: 25 Years of Image Analysis", Nature Methods, vol. 9, No. 7, Jul. 2012, pp. 671-675.
Scotlandi et al., "CD99 Engagement: An Effective Therapeutic Strategy for Ewing Tumors", Cancer Res., vol. 60, No. 18, Sep. 15, 2000, pp. 5134-5142.
Scotlandi et al., "Targeting CD99 in Association With Doxorubicin: an Effective Combined Treatment for Ewing's Sarcoma", European Journal of Cancer, vol. 42, No. 1, Jan. 2006, pp. 91-96.
Sigal et al., "Beyond Hairy Cell: the Activity of Cladribine in Other Hematologic Malignancies", Blood, vol. 116, No. 16, Oct. 21, 2010, pp. 2884-2896.
Sohn et al., "Engagement of CD99 Induces Apoptosis Through a Calcineurin-Independent Pathway in Ewing's Sarcoma Cells", The American Journal of Pathology, vol. 153, No. 6, Dec. 1998, pp. 1937-1945.
Suh et al., "Cloning, Genomic Organization, Alternative Transcripts and Expression Analysis of CD99L2, a Novel Paralog of Human CD99, and Identification of Evolutionary Conserved Motifs", Gene, vol. 307, Mar. 27, 2003, pp. 63-76.
Ventura et al., "CD99 Regulates Neural Differentiation of Ewing Sarcoma Cells Through miR-34a-Notch-Mediated Control of NF-κB Signaling", Oncogene, vol. 35, No. 30, Jul. 28, 2016, pp. 3944-3954.
Watson et al., "Endothelial CD99 Signals Through Soluble Adenylyl Cyclase and PKA to Regulate Leukocyte Transendothelial Migration", Journal of Experimental Medicine, vol. 212, No. 7, Jun. 22, 2015, pp. 1021-1041.
Weidner et al., "Immunohistochemical Profile of Monoclonal Antibody O13: Antibody That Recognizes Glycoprotein p30/32MIC2 and is Useful in Diagnosing Ewing's Sarcoma and Peripheral Neuroepithelioma", The American Journal of Surgical Pathology, vol. 18, No. 5, May 1994, pp. 486-494.
Winger et al., "Cutting Edge: CD99 is a Novel Therapeutic Target for Control of T Cell-mediated Central Nervous System Autoimmune Disease", J. Immunol., vol. 196, No. 4, Feb. 15, 2016, pp. 1443-1448.
Zucchini et al., "CD99 Suppresses Osteosarcoma Cell Migration Through Inhibition of ROCK2 Activity", Oncogene, vol. 33, No. 15, Apr. 10, 2014, pp. 1912-1921.

\* cited by examiner

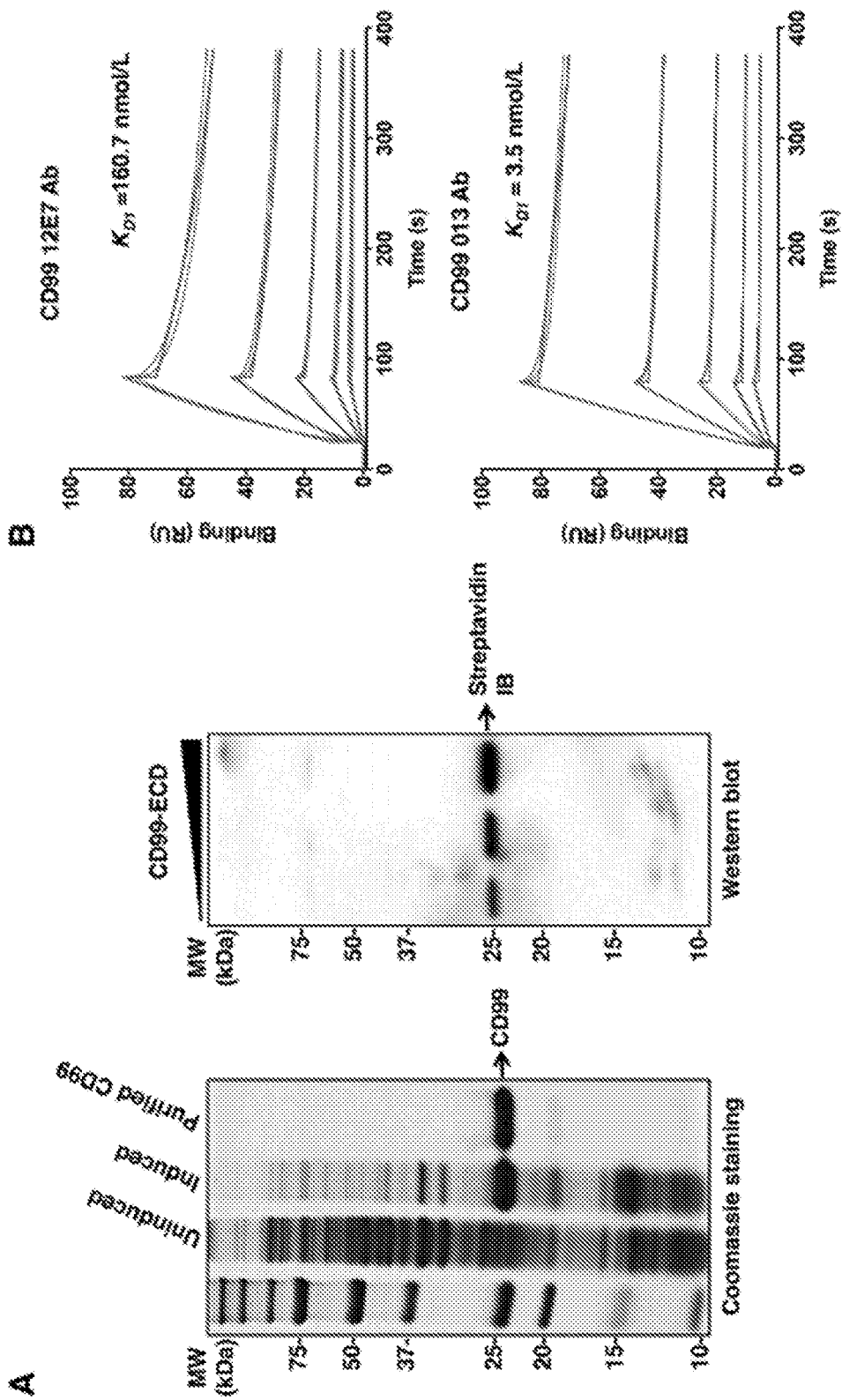
FIGURES 2A-B

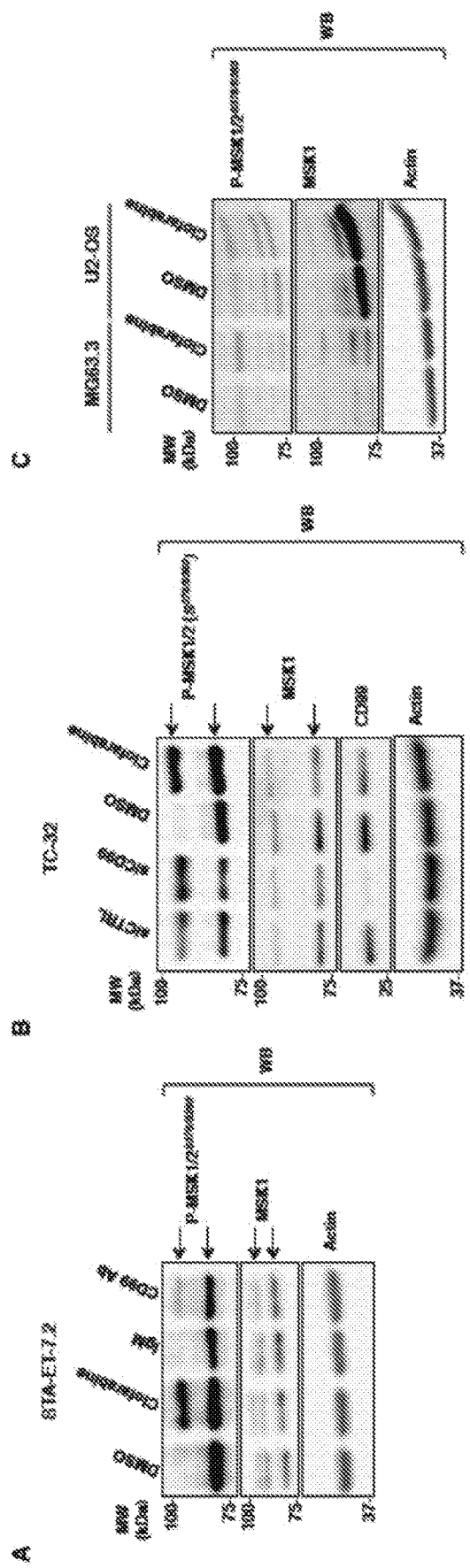
FIGURES 23A-C

SEQUENCE LISTING

```
<160> NUMBER OF SEQ ID NOS: 1

<210> SEQ ID NO 1
<211> LENGTH: 62
<212> TYPE: DNA
<213> ORGANISM: Artificial sequence
<220> FEATURE:
<223> OTHER INFORMATION: Synthetic construct

<400> SEQUENCE: 1
gatccggctg gccattatta agtcttcaag agagacttaa taatggccag ccttttttgga    60 aa                                                                    62
```

CD99 INHIBITORS AND THEIR USES

This application is a national stage application under 35 U.S.C. § 371, of International Application No. PCT/US2017/056348, filed on Oct. 12, 2017, which claims priority to U.S. Provisional Application No. 62/407,116, filed Oct. 12, 2016, which is hereby incorporated in its entirety by this reference.

BACKGROUND

The American Cancer Society estimates that, in 2017, about 1,600,000 new cases of cancer will be diagnosed. Thus, compositions and methods for treating cancer are necessary. Similarly, over 50 million Americans suffer from autoimmune disease. Therefore, compositions and methods for treating autoimmune disease are necessary

SUMMARY

Provided herein are methods for treating a CD99 antigen (CD99)+ cancer in a subject. The methods comprise administering a CD99 inhibitor.

Also provided is a method of treating a bone or soft tissue cancer in a subject comprising administering a CD99 inhibitor to the subject, wherein the cancer is a CD99+ cancer.

Further provided is a method of treating cancer in a subject comprising administering to the subject with cancer an effective amount of a membrane impermeable CD99 inhibitor, wherein the cancer is a CD99+ cancer.

Also provided is a method of treating an autoimmune disorder in a subject comprising administering to the subject with an autoimmune disorder an effective amount of a membrane impermeable CD99 inhibitor.

BRIEF DESCRIPTION OF THE FIGURES

FIGS. 2A-B show purification and characterization of recombinant bacterial CD99-ECD. In FIG. 2A, the extracellular domain of CD99 (CD99-ECD) was cloned into a bacterial expression vector as a fusion protein with a N-terminal Bioease tag for in vivo biotinylation and a C-terminal 6xHis tag. Protein expression was induced by IPTG and total bacterial lysates were run on a 12% acrylamide gel. Recombinant protein was then purified by affinity chromatography on a nickel-charged Hi-Trap chelating high-performance column. Approximately 4 µg of purified protein were run on a gel and stained with Coomassie blue (left panel). The biotinylation of the protein was confirmed by Western blotting using streptavidin-HRP conjugate (right panel). In FIG. 2B, the SPR sensorgrams show binding of CD99 monoclonal antibodies to CD99-ECD immobilized on a CM5 Biacore sensorchip. Antibodies were injected in duplicates at five increasing concentrations ranging from 15.6 to 250 and 1.25 to 20 nmol/L for clones 12E7 and 013, respectively. The solid lines show real data and the dotted lines represent curve fits for the bivalent analyte-binding model.

FIG. 3A shows that recombinant CD99-ECD was captured on a neutravidin-coated sensor chip and small molecules (50 µmol/L) were individually injected over the surface to measure direct binding in a Biacore T200 instrument. Each dot represents a small molecule. Relative binding, given in the Y-axis, was normalized for binding to an empty flow cell, a buffer alone injection and binding to the negative control protein. Any compound showing at least 20-fold difference in relative binding to CD99 over the negative control protein in terms of normalized response was selected as a primary hit. FIG. 3B shows that 160 primary hits identified from the initial binding screening were further screened for their effect on cell viability in two ES cell lines (TC-71 and RDES) vs. a negative control cell line U-2 OS to distinguish nonspecific CD99 binders from functionally relevant compounds. After 48 h treatment with each compound at 10 µmol/L concentration, cell viability was determined by WST-1 assay. Single points in the shaded area represent the secondary hits that reduced cell viability of ES cells more than 70% and OS cells less than 10%. Values are presented as the mean of three replicates. Each of FIGS. 3C and 3D show a representative steady-state affinity curve and sensorgram (inset) showing binding kinetics of clofarabine and cladribine to the purified recombinant human full-length CD99. Recombinant human full-length CD99 protein produced in HEK293 cells was immobilized by amine coupling on a CM4 Biacore sensor chip in a Biacore T200 instrument. Compounds were injected over the chip surface at 1.25, 2.5, 5 and 10 µmol/L concentrations for clofarabine and 0.625, 1.25, 2.5, 10 µmol/L concentrations for cladribine in duplicate. The final $K_D$ values were 5.3±3.2 µmol/L (n=3 separate experiments) and 3.8±3.3 µmol/L (n=4 separate experiments) for clofarabine and cladribine, respectively.

In FIG. 6A, total cell lysates were prepared from a panel of 9 ES and 13 non-ES cell lines. Immunoblotting was performed using anti-actin and anti-CD99 clone 12E7 antibodies. The purified CD99-ECD protein (150-1200 ng/lane) was used as a standard for immunoquantification. Densitometric analysis was performed as described in the Examples. Correlation analysis was performed between clofarabine (FIG. 6B) and cladribine (FIG. 6C) sensitivity and CD99 expression levels in human ES and non-ES cell lines. The $IC_{50}$ values for clofarabine and cladribine are given in FIGS. 1, 4 and 7. Statistical analysis for correlation was performed using Spearman's correlation analysis with two-tailed P values and 95% confidence interval. The solid lines represent correlations between CD99 levels and $IC_{50}$ values for clofarabine and cladribine in human ES and non-ES cell lines.

In FIG. 7A, STA-ET-7.2 ES cells were incubated with either drug at 5 µmol/L concentration or DMSO for 1 h. The cells were treated with cross-linking agent $BS^3$ as described in the Examples. The lysates were resolved in 12% SDS-PAGE followed by immunoblotting with anti-actin and anti-CD99 clone 013 antibodies. M and D represent monomeric and dimeric forms of CD99, respectively. Values given below the lanes on the immunoblot represent the relative density of the bands, and were determined using ImageJ 1.48v software. In FIG. 7B, RDES or STA-ET-7.2 ES cells were treated with 3 µmol/L of either drug for 6 h. Endogenous CD99 was immunoprecipitated from total cell lysates using either anti-CD99 clone 12E7 antibody or anti-CD99 clone 013 antibody. Immunoblot (IB) analysis was performed for cyclophilin A, CD99 and PKA-RIIα using both cell lysates (TCL) and immunoprecipitated (IP) samples. Values given below the lanes on each immunoblot represent the relative density of the bands, and were determined using ImageJ 1.48v software. In FIG. 7C, SAOS-2 and U-2 OS cells were transiently transfected with an empty mammalian expression vector (EV) or an expression construct containing a cDNA encoding full length human CD99. The growth rate of cells was monitored by electrical impedance in real time. CD99-forced expression in OS cells resulted in reduced growth rate, which was dose-dependently rescued by the addition of cladribine. The results are presented as the percentage of cell index values corresponding to 70 h and 42 h for SAOS-2 and U-2 OS cells, respectively. Values are presented as the mean±SD of four and two technical replicates for SAOS-2 and U-2 OS cells, respectively. (Asterisks indicate statistically significant differences between treatments (*p<0.05; vs. CD99 transfected control using Student's unpaired t test, two-tailed). In FIG. 7D, CD99 protein expression in cells from panel C was confirmed by immunoblotting using CD99 clone 12E7 antibody in total cell lysates.

FIG. 8A shows results with RDES, 6647, IOR/CAR and TC-71 ES cells treated with cladribine (CLA) or clofarabine (CLO) at indicated concentrations for 24 h. Immunoblot analysis was performed on total cell lysates for ROCK2 and GAPDH expression. In FIG. 8B, TC-71 control and TC-CD99-shRNA #2 cells were treated with either drug at indicated concentrations for 1, 3 and 6 h. Immunoblot analysis was performed on total cell lysates for ROCK2 and GAPDH expression. In FIG. 8C, cell migration experiments were performed using Boyden chamber transwell migration assay with 10% serum serving as the chemoattractant in the lower chamber. 6647 and TC-71 cells were pre-treated for 24 h with cladribine at 1 or 3 µmol/L and clofarabine at 0.3 or 0.5 µmol/L concentrations, respectively. The number of migrated cells was then quantified by counting the cells in the bottom chamber under the microscope. Asterisks indicate statistically significant differences between treatments (*p<0.05; vs. control using a Student's unpaired t test).

FIG. 10A shows a steady-state affinity curve and sensorgram (inset) showing binding kinetics of a membrane-impermeable analog of clofarabine, clofarabine-5'-triphosphate, to the purified recombinant human full-length CD99. Recombinant human full-length CD99 protein produced in HEK293 cells was immobilized by amine coupling on a CM4 Biacore sensor chip in a Biacore T200 instrument. Compound was injected over the chip surface at 2.5, 5, 10 and 20 µmol/L concentrations in duplicate. FIG. 10B shows cell viability evaluated by WST-1 assay following 48 h treatment of TC-71 (left panel) and A4573 ES cells (right panel) with clofarabine and clofarabine-5'-triphosphate. The $IC_{50}$ values were determined by nonlinear regression analysis using GraphPad Prism version 6.0 h software. FIG. 10C and FIG. 10D show MG63.3 OS and TC32 ES cell lines, respectively, were transiently transfected with control or DCK siRNA. DCK protein expression was confirmed by immunoblotting in total cell lysates.

In FIG. 11A, TC-71, 6647 and RDES cells and U-2 OS cells were treated with both drugs at indicated concentrations for 48 h (doses are expressed as µmol/L). Histograms display the percentage of hypodiploid cells based on DNA contents analyzed by cell sorting. Values are presented as the mean±SD of three independent experiments. In FIG. 11B, TC-71, 6647 and RDES cells were plated in semi-solid medium with either clofarabine or cladribine and all ES cells exhibited a dose-dependent inhibition in colony formation as determined by soft agar assay. The data are represented as the mean±SD of triplicate determinations. Shown in FIG. 11C are representative images of brightfield colonies from the soft agar assay (scale bar 200 μm). Asterisks indicate statistically significant differences between treatments (*p<0.05; vs. control using a Student's unpaired t test).

In FIG. 12A parental TC-71 and stably CD99 targeting shRNA expressing TC-71 cells (TC-CD99-shRNA #1 and TC-CD99-shRNA #2) were plated in semi-solid medium with either clofarabine or clofarabine-5'-triphosphate. A dose-dependent inhibition in colony formation as determined by soft agar assay was observed, which was lost in TCCD99-shRNA #1 cells with reduced CD99 expression. The data are presented as the mean±SD of triplicate determinations. Representative images of bright field colonies from the soft agar assay are shown. In FIG. 12B the same soft agar assay was done with 6647 and RDES cell lines. Asterisks indicate statistically significant differences between treatments (*p<0.05; vs. control using a Student's unpaired t test, two-tailed).

FIG. 18A shows Kaplan-Meier event-free survival curves generated for mice treated with clofarabine were compared with that of vehicle-treated mice. n indicates the number of mice per group. Statistical significances between treatments were calculated using long-rank (Mantel-Cox) test. FIG. 18B shows that tumors were measured each day. The number of mice per group for each day throughout the study is given on top of the graph. The data are represented as the mean±SD. The bar on the bottom of the figure shows the duration of the drug treatment. Asterisks indicate statistically significant differences between treatments (CTRL, control; CLF, clofarabine; ns, non-significant; *p<0.05; vs. control using non-parametric Mann-Whitney U test, two-tailed).

FIGS. 23A-D shows that clofarabine activates MSK1/2 in ES but not in OS cells. In FIG. 23A, STA-ET-7.2 cells were treated with either 0.6 μmol/L clofarabine or vehicle (DMSO) control for 24 h. In a parallel set of experiment, cells were also treated with 15 μg/mL of either mouse control IgM or CD99 blocking antibody for the same duration. Total cell lysates were analyzed by immunoblotting for MSK1/2 phosphorylation. In FIG. 23B, TC-32 cells were treated with either 0.5 μmol/L clofarabine or vehicle (DMSO) control for 24 h. In a parallel set of experiment, cells were transfected with either siRNA control or siRNA targeting the coding region of CD99 protein. Total cell lysates were analyzed after 48 h by immunoblotting for MSK1/2 phosphorylation after cell transfection. In FIG. 23C, MG63.3 and U-2 OS cells were treated with 1.0 μmol/L clofarabine for 24 h and MSK1/2 phosphorylation levels were evaluated by immunoblotting. In FIG. 23D, SCID/beige mice were implanted with TC-71 xenografts in their tibia. Three control and four clofarabine treated TC71 xenograft-bearing animals were euthanized after two days of treatment (30 mg/kg oral). Tumor lysates were analyzed by immunoblotting for MSK1/2 phosphorylation. The right panel shows the densitometric analysis of the p-MSK1/2 bands normalized to the corresponding MSK1/2 controls in clofarabine- vs. vehicle control-treated group.

DETAILED DESCRIPTION

Figure 1:
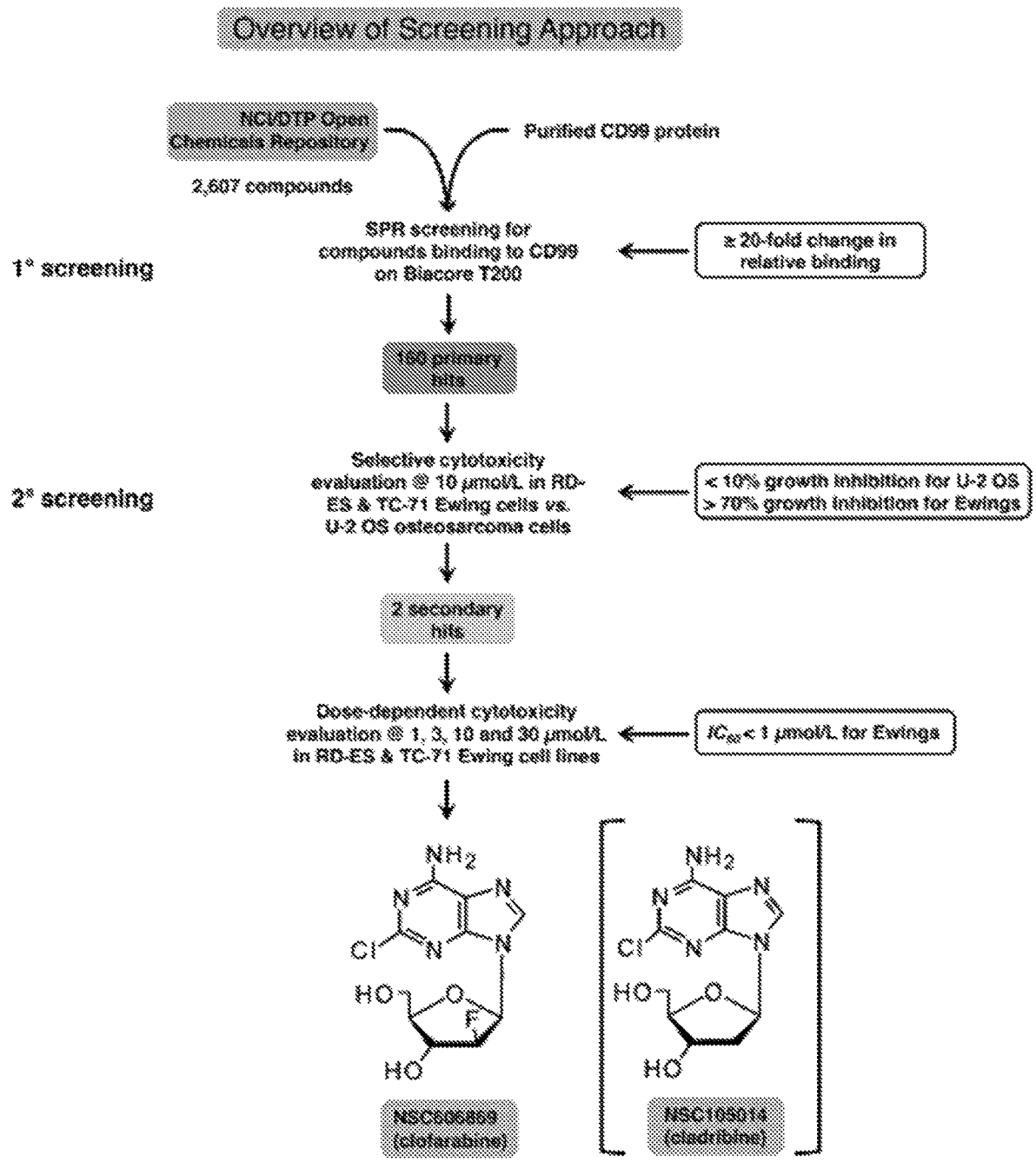
FIG. 1 is a schematic overview of a screening strategy for identification of small molecule inhibitors of CD99. NCI/DTP small molecule libraries comprised of 2,607 compounds were screened by surface plasmon resonance (SPR) technology for their ability to directly bind purified recombinant extracellular domain of human CD99 protein. The primary hits (N=160) were further tested in a secondary functional assay at 10 µmol/L concentration for their selective growth-inhibitory activity in TC-71 and RDES ES cell lines and compared with a negative control cell line, U-2 OS cell, following a 48 hour incubation period. Two compounds were identified as achieving >70% growth inhibition in ES cells with a growth-inhibitory activity of <10% in U-2 OS cells. The secondary hits were subsequently confirmed in a dose-dependent cytotoxicity assay in TC-71 and RD-ES cell lines. The chemical structure of clofarabine (NCBI PubChem ID: NSC606869) that showed a highly potent selective growth-inhibitory activity against ES cells is given. Another compound identified among 160 primary hits, cladribine (NCBI PubChem ID: NSC105014), shares a high structural similarity to clofarabine that differs only by the presence of one fluorine atom. Cladribine exhibited some degree of selective cytotoxicity in secondary screening against ES cells, and a subsequent dose-dependent cytotoxicity assay revealed an $IC_{50}$ lower than 1 µmol/L for TC-71 and RD-ES cell lines too.

Provided herein are methods for treating a CD99+ cancer in a subject. The methods comprise administering a CD99 inhibitor. For example, provided herein is a method of treating a bone or connective tissue cancer in a subject comprising administering to the subject with the bone or connective tissue cancer an effective amount of a CD99 inhibitor, wherein the cancer is a CD99+ cancer.

Also provided is a method of treating cancer in a subject comprising administering to the subject with cancer an effective amount of a membrane impermeable CD99 inhibitor, wherein the cancer is a CD99+ cancer.

Also provided are methods of treating an autoimmune disorder in a subject. The methods comprise administering a CD99 inhibitor to the subject. Further provided is a method of treating an autoimmune disorder in a subject comprising administering to the subject with an autoimmune disorder an effective amount of a membrane impermeable CD99 inhibitor.

In the methods provided herein, the CD99 inhibitor can, for example, be selected from the group consisting of a small molecule, a polypeptide, a peptidomimetic, an antibody or a combination thereof. For example, and not to be limiting, the CD99 inhibitor can be a compound having Formula I,

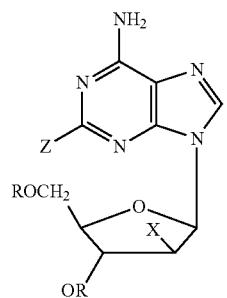

wherein R, each of which may be the same or different, is hydrogen, or a protecting group; wherein Z is selected from the group consisting of F, Cl and Br; wherein X is H or F; or a pharmaceutically acceptable salt thereof.

In the methods provided herein, the CD99 inhibitor can be a compound of Formula I having Formula II (clofarabine) or a pharmaceutically acceptable salt thereof.

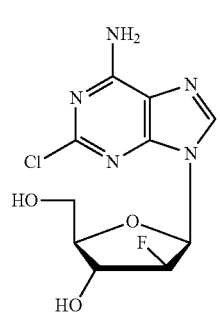

The CD99 inhibitor can also be a compound of Formula I having Formula III (cladribine) or a pharmaceutically acceptable salt thereof.

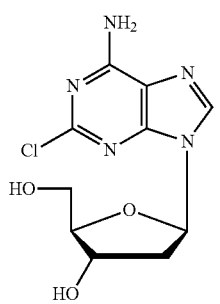

Other CD99 inhibitors include, but are not limited to, NSC255109 (17-amino-17-demethoxygeldanamycin; 17-AG), NSC126771 (dichloroallyl lawsone), clofarabine-5'-triphosphate, NSC269148, NSC89671, NSC662825, NSC265450, NSC403148, NSC145150, NSC326231 and NSC149046. It is understood that all NSC numbers provided herein correspond to substances or chemicals available from the Cancer Chemotherapy National Service Center (NSC) maintained by the Developmental Therapeutics Program (DTP) at the National Cancer Institute (https://dtp.cancer.gov/databases_tools/data_search.htm). Optionally, any of the CD99 inhibitors described herein, including membrane-impermeable CD99 inhibitors, can have decreased ability to decrease or inhibit DNA synthesis in a cell as compared to a CD99 inhibitor that inhibits DNA synthesis in a cell. Optionally, the ability of the CD99 inhibitor to inhibit DNA synthesis is decreased by about 10%, 20%, 30%, 40%, 50%, 60%, 70%, 80%, 90%, 100% or any percentage in between these percentages. Optionally, any of the CD99 inhibitors described herein, including membrane-impermeable CD99 inhibitors, can have a reduced ability to effect cell cycle arrest in a cell as compared to a CD99 inhibitor that effects cell cycle arrest in a cell. Optionally, the ability of the CD99 inhibitor to effect cell cycle arrest is reduced or decreased by about 10%, 20%, 30%, 40%, 50%, 60%, 70%, 80%, 90%, 100% or any percentage in between these percentages.

In any of the methods provided herein, the CD99+ inhibitor can be a membrane-impermeable CD99 inhibitor. For example, the membrane-impermeable CD99+ inhibitor can be a membrane impermeable analog of Formula I, Formula II, Formula III, NSC255109 (17-amino-17-demethoxygeldanamycin; 17-AG), NSC126771 (dichloroallyl lawsone) clofarabine-5'-triphosphate, NSC269148, NSC89671, NSC662825, NSC265450, NSC403148, NSC145150, NSC326231, NSC149046 or a pharmaceutically acceptable salt thereof. As used throughout, a membrane-impermeable CD99 inhibitor is an inhibitor that has decreased ability to cross the cell membrane and/or enter a cell as compared to a control, for example, a membrane-permeable CD99 inhibitor. Optionally, the ability of the membrane-impermeable CD99 inhibitor to cross the cell membrane is decreased by about 50%, 55%, 60%, 65%, 70%, 75%, 80%, 85%, 95%, or 99% as compared to a membrane permeable inhibitor. Optionally, the ability of the membrane-impermeable CD99 inhibitor to inhibit DNA synthesis is decreased by about 10%, 20%, 30%, 40%, 50%, 60%, 70%, 80%, 90%, 100% or any percentage in between these percentages. Optionally, the membrane impermeable inhibitor exhibits decreased toxicity against normal, or non-malignant cells as compared to a membrane permeable CD99 inhibitor. For example, the membrane-impermeable CD99 inhibitor can be about 25%, 30%, 40%, 50%, 60%, 70%, 80%, 90%, 95%, 100% or any percentage in between the percentages less toxic to normal or non-malignant cells as compared to a membrane permeable CD99 inhibitor.

For example, and not to be limiting, the analog can be a compound having Formula IV (clorfarabine-5'-triphosphate) or a pharmaceutically acceptable salt thereof.

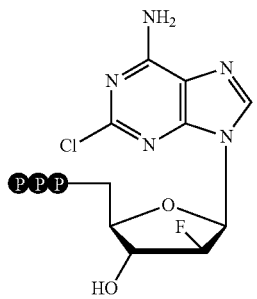

IV

As used throughout, CD99 antigen (Cluster of differentiation 99; CD99), also known as MIC2 or single-chain type-1 glycoprotein, is a heavily O-glycosylated transmembrane protein that is encoded by the CD99 gene in humans. CD99 regulates various cellular response, including cell adhesion and leukocyte extravasation. As used throughout, a CD99+ cancer is a cancer characterized by one or more cell types that express CD99 on their cell surface. CD99 is found on the cell surface of cancer tumors, for example, bone cancer tumors such as Ewing's sarcoma tumors and malignant glioma. CD99 is also found on disease stem cells of myeloid malignancies such as leukemia, for example, acute myeloid leukemia and acute lymphocytic leukemia. Any of the methods provided herein can further comprise diagnosing a subject with a CD99+ cancer, i.e., a cancer associated with CD99 expression and/or CD99 activity, including increased expression and/or activity as compared to a subject that does not have cancer. The methods can further comprise diagnosing a subject with an autoimmune disorder associated with CD99 expression and/or CD99 activity, including increased expression and/or activity as compared to a subject that does not have an autoimmune disorder. Diagnosing a subject can include, one or more of a biopsy, CAT scan, angiogram, ultrasound, X ray, MRI, blood chemistry tests, immunohistochemistry and the like.

In the methods provided herein an inhibitor of CD99 inhibits or decreases expression and/or at least at least one activity of CD99, for example, cancer cell growth or proliferation, CD99 cell surface dimerization, CD99 binding to PKA and/or cyclophilin A, CD99-mediated inhibition of MSK1/2 phosphorylation, cell motility or cell invasion, to name a few. It is understood that inhibition of CD99 does not have to be complete. Therefore, the CD99 inhibitors provided herein can inhibit or decrease expression and/or at least one activity of CD99, for example, cancer cell growth and/or proliferation by about 10%, 20%, 30%, 40%, 50%, 60%, 70%, 80%, 90%, 100% or any percentage in between these percentages.

Provided herein are CD99 inhibitors having the structure of Formula I, II, III or IV. Also provided is a composition comprising one or more of the CD99 inhibitors provided herein, including one or more membrane-impermeable CD99 inhibitors. For example, the composition can comprise a CD99 inhibitor having the structure of Formula I, II, III or IV, or a pharmaceutically acceptable salt thereof. In another example, the composition comprises a membrane-impermeable CD99 inhibitor that is an analog of Formula I, II, III or IV, or a pharmaceutically acceptable salt thereof.

As used herein, the term pharmaceutically acceptable salt refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds provided herein, for example, pharmaceutically acceptable salts of a compound of Formula I, II, III or IV include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, trifluoroacetic acid, undecanoate, valerate salts, and the like.

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The methods for treating cancer provided herein can be used to treat any CD99+ cancer. For example, the CD99+ cancer can be a glioma, a leukemia, a lymphoma, a bone cancer or a soft tissue cancer. In the methods for treating bone cancer provided herein, the bone or soft tissue cancer is optionally selected from the group consisting of osteosarcoma, chondrosarcoma, Ewing's sarcoma, fibrosarcoma, malignant fibrous histiocytoma, chondrosarcoma, leiomyosarcoma, chordoma, giant cell tumor of the bone and spindle cell sarcoma.

In the methods for treating an autoimmune disorder provided herein, the autoimmune disorder can be selected from the group consisting of multiple sclerosis, lupus, inflammatory bowel disease, rheumatoid arthritis, psoriasis, Guillain-Barre syndrome, Graves' disease, myasthenia gravis, vasculitis, amyloidosis, Addison's disease, Behcet's Disease, celiac Disease, Crohn's Disease, Hashimoto's thyroiditis, Kawasaki disease, psoriasis and scleroderma.

In the methods for treating cancer, treat, treating, and treatment refer to a method of reducing or delaying one or more effects or symptoms of a CD99+ cancer. The subject can be diagnosed with a CD99+ cancer. Treatment can also refer to a method of reducing the underlying pathology rather than just the symptoms. The effect of the administration to the subject can have the effect of, but is not limited to, reducing one or more symptoms (e.g., reduced pain, reduced size of the tumor, etc.) of the cancer, a reduction in the severity of the cancer (e.g., reduced rate of growth of a tumor or rate of metastasis), the complete ablation of the cancer, or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between.

In the methods for treating an autoimmune disorder, treat, treating, and treatment refer to a method of reducing or delaying one or more effects or symptoms of an autoimmune disorder. The subject can be diagnosed with an autoimmune disorder. Treatment can also refer to a method of reducing the underlying pathology rather than just the symptoms. The effect of the administration to the subject can have the effect of, but is not limited to, reducing one or more symptoms of the autoimmune disorder (e.g., reduced pain, reduced inflammation, fatigue, etc.), a reduction in the severity of the autoimmune disorder, the complete ablation of the autoimmune disorder, or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between. It is understood that treatment does not necessarily refer to a cure or complete ablation of the disease, condition, or symptoms of the disease or condition, although treatment can include a cure or complete ablation of the disease, condition, or symptoms of the disease or condition.

As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

The methods provided herein optionally further include administering a second therapeutic agent to the subject. For example, in the methods for treating cancer, the second therapeutic agent can be a tyrosine kinase inhibitor such as, for example, imatinib, dasatinib, nilotinib, sorafenib, pazopanib, erlotinib, lapatinib, sunitinib or bosutinib, to name a few. The second therapeutic agent can be a chemotherapeutic agent. Examples of chemotherapeutic agents include, but are not limited to doxorubicin, cisplatin, carboplatin, etoposide, ifosfamide, cyclophosphamide, methotrexate and vincristine, to name a few. Any of the methods provided herein can optionally further include administering radiation therapy to the subject. Any of the methods provided herein can optionally further include surgery.

In the methods for treating an autoimmune disorder, the second therapeutic agent can be, but is not limited to one or more of a corticosteroid, methotrexate, cyclophosphamide, azathioprine, cyclosporine, interferon beta-1a, glatiramer acetate, daclizumab, teriflunomide, fingolimod, dimethyl fumarate, alemtuzumab, mitoxantrone, ocrelizumab or natalizumab, to name a few.

The term effective amount, as used throughout, is defined as any amount of a CD99 inhibitor necessary to produce a desired physiologic response. For example, one or more CD99 inhibitors can be administered at a dosage of about 10-100 mg/m$^2$ per day. When administering a CD99 inhibitor, for example, a compound of Formula I, II, III, or a membrane impermeable analog thereof, the effective amount is optionally less than the amount used in chemotherapeutic methods to treat leukemia, but is an amount sufficient to inhibit CD99. Thus, the dosage of a compound of Formula I, II, III, or a membrane impermeable analog thereof in the present methods is optionally lower than a chemotherapeutic dosage of Formula I, II, III. For example, the dosage is optionally less than about 52 mg/m$^2$ or less than about 2 mg/kg. Optionally, the dosage can be less than about 50, 45, 40, 35, 30, 25 or 20 mg/m$^2$. Optionally, the dosage can be less than about 2, 1.9, 1.8, 1.7, 1.6, 1.5, 1.4, 1.3, 1.2, 1.1, 1, 0.9, 0.8, 0.7, 0.6, 0.5, 0.4 or 0.3 mg/kg. However, it is understood that other dosages of a CD99 inhibitor can be used. Exemplary dosage amounts for a mammal include doses from about 0.5 to about 200 mg/kg of body weight of active compound per day, which may be administered in a single dose or in the form of individual divided doses, such as from 1 to 4 times per day can be used. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 1 to about 5 mg/kg of body weight of active compound per day, about 20 mg/kg of body weight of active compound per day, about 10 mg/kg of body weight of active compound per day, or about 5 mg/kg of body weight of active compound per day. One of skill in the art would adjust the dosage as described below based on specific characteristics of the inhibitor and the subject receiving it.

Effective amounts and schedules for administering the CD99 inhibitor can be determined empirically and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, unwanted cell death, and the like. Generally, the dosage will vary with the type of inhibitor, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

The CD99 inhibitors described herein can be provided in a pharmaceutical composition. These include, for example, a pharmaceutical composition comprising a therapeutically effective amount of one or more CD99 inhibitors and a pharmaceutical carrier.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012).

Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

The compositions are administered in a number of ways depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Pharmaceutical compositions can also be delivered locally to the area in need of treatment, for example by topical application or local injection. Any of the compositions can be delivered via an implant, for example, a bone implant that releases a CD99 inhibitor. Effective doses for any of the administration methods described herein can be extrapolated from dose-response curves derived from in vitro or animal model test systems.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Study Approval

All animal studies were conducted under an animal use protocol approved by the Georgetown University's Institutional Animal Care and Use Committee in accordance with NIH guidelines for the ethical treatment of animals.

Chemical Libraries and Drugs

The chemical library collection, consisting of Diversity Set, Mechanistic Set, and Natural Products Set, used in this work was kindly supplied by NCI/DTP Open Chemical Repository. The compounds were supplied as 1 or 10 mmol/L stock solutions in DMSO in 96-well microtiter plates. The primary hits identified from the initial compound-CD99 binding screening were obtained as powder samples in vials from the NCI/DTP Open Chemical Repository, and dissolved in DMSO as 10 mmol/L stock solutions. Clofarabine was purchased from Sigma Aldrich (St. Louis, Mo.; #C7495) or Selleck Chemicals (Houston, Tex.; #S1218). Cladribine was obtained from Sigma Aldrich (#C4438 or #1134200). Dasatinib (#S1021) was purchased from Selleck Chemicals.

Cell Lines and Culturing

Embryonic stem (ES) cell lines RDES, TC-71, STA-ET-7.2 and MHH-ES were grown in RPMI supplemented with 10% FBS and 10 mmol/L HEPES. TC32 and A4573 cells were maintained in RPMI with 10% FBS. SKES cells were grown in McCoy's medium with 15% FBS. COG-E-352, CHLA-9 and CHLA-10 cells were grown in IMEM with 15% FBS and 1% (v/v) ITS (Sigma Aldrich). IOR/CAR, SK—N—MC, A673 and 6647 cells were grown in IMDM, supplemented with 100 U/ml penicillin, 100 μg/ml streptomycin, and 10% FBS. The leukemia cell lines MOLT-4 and Jurkat were maintained in RPMI with 10% FBS. The glioblastoma cell line A172 was grown in DMEM with 10% FBS. U-87 MG cells were grown in DMEM with 10% FBS and 1% (v/v) nonessential amino acids (Gibco (Waltham, Mass.)). The human OS cell lines HOS-MNNG, SAOS-2/LM7, SAOS-2, U-2 OS and MG63.3 and mouse OS cell lines K7M2 and K12 were grown in DMEM with 10% FBS. IOR/MOS, MG-63, IOR/OS20, IOR/OS14, IOR/OS9, IOR/OS10 cells and the rhabdomyosarcoma cell lines RD/18, RH4, RH30 and RH1 were routinely cultured in IMDM supplemented with 10% FBS, 100 U/ml penicillin and 100 µg/ml streptomycin. The breast cancer cell line MCF-7 and human lung adenocarcinoma cell line A549 were maintained in RPMI with 10% FBS. The prostate cancer cell line PC3 was grown in RPMI with 10% FBS with 10 mmol/L HEPES. The human embryonic kidney cell line HEK293 was grown in DMEM with 10% FBS. All cell lines were maintained in a fully humidified atmosphere of 5% $CO_2$ at 37° C., and tested mycoplasma-negative using MycoAlert kit (Lonza (Basel, Switzerland)).

Cell Viability and Proliferation Assays

Cell viability was assayed by using the MTT (Trevigen (Gaithersburg, Md.)) or WST-1 (Roche Diagnostics (Basel, Switzerland) cell proliferation assays according to the manufacturer's instructions. For assessment of cell proliferation in real time, the xCELLigence system (RTCA; ACEA Biosciences Inc. (San Diego, Calif.)) was used. After background impedance measurement, cells were seeded to each well (5,000-10,000 cells/well in 100 µL) in E-Plate 16 (ACEA Biosciences Inc.), and allowed to attach overnight. The day after, the medium was replaced with 100 µL of fresh medium containing test agents at indicated concentrations. The plate was installed into the RTCA system, and the electrical impedance (represented as cell index) was measured every 10 min.

Cloning and Preparation of Recombinant CD99-ECD Protein

The Champion™ pET104 BioEase™ Gateway® Expression System (Invitrogen (Carlsbad, Calif.)) was used to produce CD99-ECD fused with a N-terminal biotin tag, as directed by the manufacturer's instructions. Briefly, the DNA sequence encoding the extracellular domain (Asp23-Asp122) of human CD99 was amplified by PCR using pcDNA3.1 expression vector (Life Technologies (Carlsbad, Calif.)) carrying the full-length human CD99 cDNA transcript variant 1 as template. The primers were designed to include an additional C-terminal 6×His tag in the protein. The PCR product was gel purified with a QIAquick gel extraction kit (Qiagen (Hilden, Germany)) and subcloned into the pDONR 221 entry vector. The entry clone was then subjected to a recombination reaction with pET104.1-DEST destination vector, an expression vector with a N-terminal BioEase tag. The presence of an insert was confirmed by DNA sequencing.

CD99-ECD was expressed in *Escherichia coli* BL21 (DE3) cells. A saturated overnight culture of cells was diluted by 20-fold into fresh LB medium containing 100 µg/mL ampicillin. To induce the expression of CD99-ECD, cells were grown to $OD_{600nm}$ 0.5-0.7 at 37° C. and induced by the addition of isopropyl-β-D-thiogalactopyranoside to a final concentration of 1 mmol/L. The cultures were grown for an additional 3 h at 37° C. Cells were harvested by centrifugation at 8,000×g for 15 min, resuspended in 50 mmol/L sodium phosphate buffer, pH 7.4, containing 500 mmol/L NaCl, 10 mmol/L imidazole and 1 Complete EDTA-free protease inhibitor tablet/50 mL (Roche Diagnostics), and lysed by sonication. The lysates were then centrifuged at 13,500×g for 10 min at 4° C. to get rid of any cell debris, and subjected to an affinity chromatography on a nickel-charged Hi-Trap chelating high-performance column (GE Healthcare Bio-Sciences (Pittsburgh, Pa.)) in an AKTA Explorer chromatography system (GE Healthcare Bio-Sciences). Protein fractions were finally eluted with a linear gradient of imidazole (10 to 1000 mmol/L) in the same buffer. The purity of the protein was assessed by SDS-PAGE followed by Coomassie staining. The eluted fractions were stored at −80° C. for further use.

Transient DNA Transfection

U-2 OS and SAOS-2 cells were transfected with pcDNA3.1 expression vector carrying the human full-length CD99 transcript variant 1 cDNA using the X-tremeGene 9 DNA transfection reagent (Roche Diagnostics) according to the manufacturer's recommendations. The expression of CD99 was assessed after 48 h by immunoblotting.

Gene Silencing with shRNA

Stable silencing of CD99 was obtained in TC-71 as previously described in Rocchi et al. ("CD99 inhibits neural differentiation of human Ewing sarcoma cells and thereby contributes to oncogenesis," *J Clin Invest* 120: 668-80 (2010)). Briefly, an shRNA plasmid (pSilencer 2.1-U6 Neo vector; Ambion (Waltham, Mass.)) expressing CD99 siRNA-1 (5'-GATCCGGCTGGCCATTATTAAGTCT-CAAGAGAGACTTAATAATGGCC AGCCTTTTTG-GAAA-3') (SEQ ID NO:1) was created and ES cells were transfected using the calcium phosphate transfection method. TC-CD99-shRNA clones (TC-CD99-shRNA #1 and TC-CD99-shRNA #2) were established after selection in neomycin (500 µg/ml) (Sigma-Aldrich). The expression of DCK and CD99 was suppressed transiently by using a validated small interfering RNA (siRNA) duplexes targeting coding region (Invitrogen (Carlsbad, Calif.); #s186 and #s8768, respectively). Silencer™ Select Negative Control No. 2 siRNA (Invitrogen) was used as the control. Cells were transfected with DCK or CD99 or control siRNA oligonucleotides using X-tremeGene siRNA transfection reagent (Roche Diagnostics (Basel, Switzerland)) according to the manufacturer's protocol. The cells were analyzed for DCK and CD99 knockdown after 45 or 72 h by immunoblotting.

Cell Cycle and Cell Death Analysis

ES and OS cell lines were treated with cladribine or clofarabine at different concentrations for 48 h. For the evaluation of cell cycle, cell cultures were incubated with 10 µmol/L bromodeoxyuridine (BrdU) (Sigma-Aldrich) for 1 h in a $CO_2$ atmosphere at 37° C. Harvested cells were fixed in ice-cold 70% ethanol for 30 min. After DNA denaturation with 2 N HCl for 30 min at room temperature, cells were washed with 0.1 M $Na_2B_4O_7$, pH 8.5 and processed for indirect immunofluorescence staining, using α-BrdU (BD Biosciences (San Jose, Calif.)) diluted 1:4 as a primary MAb and α-mouse FITC (1:100—Thermo Scientific (Waltham, Mass.)) as a secondary antibody. After treatment with 0.5 mg/ml RNase and staining with 20 µg/ml propidium iodide, cells were and analyzed by flow cytometry (FACSCalibur; Becton Dickinson (Franklin Lakes, N.J.)) for cell cycle evaluation and for assessing cell death by DNA content analysis.

Chemotaxis/Cell Migration Assay

Motility assay was done using Trans-well chambers (Costar; Corning (Corning, N.Y.)) according to manufacturer's instructions. 6647 and TC-71 cells were pre-treated for 24 h with the drugs (cladribine 1 µmol/L or 3 µmol/L and clofarabine 0.3 µmol/L or 0.5 µmol/L, respectively), counted, and 100,000 viable cells were seeded in the upper chamber for migration analysis to rule out possible effects of drug treatment on cell vitality that might affect cell migration.

Soft Agar Colony Formation Assay

Anchorage-independent growth was determined in 0.33% agarose (Sea-Plaque Agarose, Lonza) with a 0.5% agarose underlay. Cell suspensions (3,300 cells/60-mm dish) were plated in semisolid medium with or without clofarabine or cladribine and incubated at 37° C. in a humidified 5% $CO_2$ atmosphere. Colonies were counted after 7-12 days.

Synergy Analysis

The drugs used for initial synergy screening were the highest purity products obtained from commercial sources, and were as follows: Paclitaxel, Fludarabine, Irinotecan, Emcyt, Lapatinib, 5-Fluorouracil, Procarbazine, Azacitidine, Doxorubicin, Valrubicin, Bortezomib, Sorafenib, Dasatinib, Triethylenemelamine, Oxaliplatin, Gefitinib, Carmustine, Nilotinib, Quinacrine, Bleomycin, Tamoxifen, Pipobroman, Mitoxantrone and Topotecan. Synergistic interactions based upon calculation of the combination index (CI) were determined from each combinatorial experiment according to Chou and Talalay (*Adv. Enzyme REgul* 22: 27-55 (1984)), using the CompuSyn software (ComboSyn, Inc. (Paramus, N.J.)). The interactions were studied at a constant ratio based on the $IC_{50}$ concentrations of the drugs. Combination data were presented using effect-orientated Fa-CI plot, which is represented by combination data points as well as their simulated curves, and plots the fraction affected (Fa; i.e. $F_{a0.5}$ represents the $IC_{50}$ value) vs. CI. In this plot, combination indices are interpreted such that a CI=1 represents additive, CI>1 represents antagonistic and CI<1 represents synergistic effects of the drug combinations. CI values were generated for tested compounds in different ES cell lines after treatment for 48 h from single experiments in triplicates.

SPR Experiments

The initial binding screening of the NCI/DTP chemical libraries was performed on a Biacore T200 instrument at room temperature using a neutravidin-coated CM5 chip (GE Healthcare Bio-Sciences) coupled with biotinylated CD99-ECD on one flow cell at levels of ~3,000 response units (RU). A negative control protein, Ly6k was immobilized on another flow cell of the same chip (~11,000 RU), and the first flow cell was left empty for reference subtraction due to nonspecific binding. Analytes were diluted in HBS—P buffer [10 mmol/L HEPES, pH 7.4, 150 mmol/L NaCl, % 0.05 (v/v) surfactant P20], and were injected individually over all flow cells. The running buffer contained appropriate concentrations of DMSO in HBS—P to match the DMSO level of the samples. Kinetic studies for antibody- or compound-CD99 interactions were performed in a Biacore T200 instrument. Purified recombinant human full-length CD99 produced in HEK293 cells was purchased from Origene (Rockville, Md.) (#TP304056). The recombinant human full-length CD99 was immobilized on a CM5 sensor chip by the amine-coupling method in sodium acetate buffer, pH 4.0 (~10,000 RU). The first flow cell was left empty for background signal subtraction. Kinetic characterization of the interactions was done by injecting increasing concentrations of analytes as indicated over CD99-captured and control surface. $K_D$ (equilibrium dissociation constant) values were obtained using BiaEvaluation software (version 1.0) (Biacore) (GE Healthcare). All kinetic experiments were conducted in HBS—P buffer, which contained 1% (v/v) DMSO in case of compounds.

Preparation of Cell Lysates and Immunoblotting

Cells were lysed in phospholysis buffer (50 mmol/L HEPES, pH 7.9, 100 mmol/L NaCl, 4.0 mmol/L sodium pyrophosphate, 10 mmol/L EDTA, 10 mmol/L sodium fluoride, and 1% Triton X-100) containing 2.0 mmol/L sodium vanadate, 1.0 mmol/L PMSF, 4.0 µg/mL aprotinin, 4.0 µg/mL leupeptin, and 1.0 µg/mL calyculin A on ice. Cells were scraped off the plate, transferred to microcentrifuge tubes and incubated on ice for 30 min to complete the cell lysis. The samples were then vortexed briefly, and centrifuged at 16,000×g for 10 min to remove any cell debris. The clear supernatant was collected, protein content was measured by the BCA assay using bovine serum albumin as a standard (Pierce (Waltham, Mass.)), and stored at −80° C. for further use. Immunoblotting experiments were performed as previously described (*Mol. Cell. Biol.* 35: 3145-3162 (2015)). Equal amounts of proteins from the lysates were resolved by SDS-PAGE and then transferred to Immobilon P membranes (Millipore (Billerica, Mass.)). After the blocking step, proteins were probed using following primary antibodies: anti-CD99 clone 12E7 (Dako, Inc.; #M3601) at 1:500 dilution; anti-CD99 clone 013 (Invitrogen, #180235) at 1:1,000 dilution; anti-cyclophilin A (Abcam, #ab58144 (Cambridge, UK)) at 1:500 dilution; anti-PKA-RIIα (Santa Cruz Biotechnology, #sc-908) at 1:500 dilution; streptavidin-HRP (Cell Signaling, #3999 (Danvers, Mass.)) at 1:1, 000 dilution; anti-actin-HRP, (Santa Cruz Biotechnology, #sc-1615 (Santa Cruz, Calif.)) at 1:5,000 dilution. The bands were detected by incubating the membrane with Immobilon Western chemiluminescent HRP substrate (Millipore) according to the manufacturer's instructions, followed by imaging the resulting chemiluminescence using a Fujifilm LAS-3000 imaging system. Quantitative analysis of protein bands detected by immunoblotting was performed using ImageJ 1.48v software (*Nat. Methods* 9: 671-675 (2012)).

Immunoprecipitation and Immunoblotting

Immunoprecipitation (IP) and immunoblotting experiments were performed as previously described (*Mol. Cell Biol.* 35: 3145-3162 (2015) using the following primary antibodies: anti-CD99 clone 12E7 (Dako, Inc.; #M3601); anti-CD99 clone 013 (Invitrogen, #180235 or #MA5-12287); anti-CD99 clone [EPR3097Y] (Abcam, #75858), anti-cyclophilin A (Abcam (Cambridge, United Kingdom), #ab58144); anti-PKA-RIIα (Santa Cruz Biotechnology, #sc-908); streptavidin-HRP (Cell Signaling, #3999); anti-actin-HRP, (Santa Cruz Biotechnology (Dallas, Tex.), #sc-1615); anti-ROCK2 clone C20 (Santa Cruz Biotechnology, #sc-1851); anti-MSK1 (Cell Signaling (Danvers, Mass.), #3489); anti-phospho-MSK1(5376)/MSK2(5360) (R&D Systems (Minneapolis, Minn.), #MAB1094); anti-DCK (Abcam, #96599); anti-GAPDH (Santa Cruz Biotechnology, #sc-25778). Quantitative analysis of protein bands was performed using ImageJ 1.48v software. Immunoblotting was performed as described above.

CETSA

The CETSA method was used according to Martinez Molina et al. ("Monitoring drug target engagement in cells and tissues using the cellular thermal shift assay," *Science* 341: 84-87 (2013)) and Jafari et al. ("The cellular thermal shift assay for evaluating drug target interactions in cells," Nat Protoc 9:2100-22 (2014)). The total cell lysates from TC-71 cells were incubated with either vehicle (DMSO) control or 3.0 µmol/L clofarabine at room temperature for 30 min. The cell lysates in 60 µL volumes were individually heated in thin wall PCR tubes to the indicated temperatures for 3 min, by using Veriti 96-well Thermal Cycler (Applied Biosystems (Foster City, Calif.)). Samples were then centrifuged at 16,000×g for 30 min at 4° C. to remove insoluble proteins, and 40 ul of the resulting supernatants were transferred into new eppendorf tubes for subsequent SDS-PAGE and immunoblotting analysis.

Human Phospho-Kinase Array

The phosphorylation profile in the cells was analyzed using the Proteome Profiler Human Phospho-Kinase Array (R&D Systems) according to the manufacturer's instructions. STA-ET-7.2 cells were plated in a 100-mm dish and grown to produce a subconfluent culture. Cell lysate samples (0.6 mg in 2.0 mL) were applied per array set (A and B; 1.0 mL lysate for each) comprised of two nitrocellulose membranes with the spotted capture antibodies in duplicate. The spots were detected using the biotinylated antibodies and incubating the membrane with Immobilon Western chemiluminescent HRP substrate (Millipore (Billerica, Mass.)) according to the manufacturer's instructions. The resulting chemiluminescent signal was acquired using a Fujifilm LAS-3000 imaging system.

Chemical Cross-Linking with $BS^3$

A monolayer of STA-ET-7.2 ES cells were grown to 80-90% confluency in 10-cm tissue culture dishes, and incubated with clofarabine and cladribine at 5 μmol/L concentration or vehicle control (DMSO) for 1 h. The cells were rinsed 3 times with ice-cold PBS, and treated with 1 mmol/L $BS^3$ (Thermo Scientific) in PBS for 10 min at 37° C. according to manufacturer's instructions. The reaction was quenched with the addition of 20 mmol/L Tris-HCl, pH 7.5. Protein samples were then prepared by lysing the cross-linked cells in a lysis buffer as described above.

Orthotopic Mouse Xenograft Studies

Five-week-old female SCID/bg mice (Taconic Farm, Inc., Germantown, N.Y.) were injected intratibially with TC-71 (one million/50 μL PBS), SKES (two million/100 μL PBS) and A4573 (one million/100 μL PBS) cells. Sample sizes for all experiments were estimated using StatMate 2.0a software (GraphPad) assuming a mean tumor volume of 1.0 and 0.75 $cm^3$ for control and treatment groups as the endpoints, respectively, with control group standard deviation of 150 $mm^3$ at 0.95% power and a significance level (alpha) of 0.05 (two-tailed). After primary tumors reached ≈150-200 $mm^3$ in size, mice were randomly allocated to vehicle control (DMSO), clofarabine and cladribine treatment groups using the random number generator function in Microsoft Excel. Clofarabine and cladribine were solubilized in DMSO as 120 or 80 mg/mL stock solutions for i.p. administration, and the dosing solutions were prepared by 10x dilutions in sterile PBS. For oral administration, clofarabine was dissolved in PEG 400, then diluted to a final concentration of 25% PEG 400 in sterile 0.9% sodium chloride solution. Mice carrying TC-71 xenografts were treated by i.p. injection with clofarabine (30 mg/kg), cladribine (20 mg/kg) or vehicle (DMSO, 10% (v/v)) in a volume of 50 μL, or with clofarabine (30 mg/kg) administered orally by gavage in a volume of 100 μL, once daily, for 14 days. SKES and A4573 xenograft-bearing mice were treated by i.p. injection with clofarabine (30 mg/kg), cladribine (20 mg/kg) or vehicle (DMSO, 10% (v/v)), once daily for the indicated days. The tumor volumes were determined by the formula $(\pi/6)\times length^2 \times width$ and measured every day using a slide caliper. Animals found dead overnight with tumors smaller than 1.0 $cm^3$ in size or mice euthanized for tumor ulceration were censored from the survival analyses.

Histology and Immunohistochemistry

All tumor tissues were fixed in 10% neutral buffered formalin for 24 h, dehydrated through a graded series of alcohols and cleared in xylenes prior to embedding in paraffin. Embedded tissues were cut into 5 μm thick sections and stained with hematoxylin and eosin (H&E). Immunohistochemical staining was performed for CD99 and caspase 3 (cleaved). Five micron sections from formalin fixed paraffin embedded tissues were de-paraffinized with xylenes and rehydrated through a graded alcohol series. Heat induced epitope retrieval was performed by immersing the tissue sections at 98° C. for 60 min in 10 mmol/L citrate buffer (pH 6.0). Immunohistochemical staining was performed using a horseradish peroxidase labeled polymer from Agilent (Santa Clara, Calif.) (#K4001, #K4003) according to manufacturer's instructions. Briefly, slides were treated with 3% hydrogen peroxide and 10% normal goat serum for 10 min each, and exposed to primary antibodies for CD99 (Abcam, #ab8855) at a 1:100 dilution and for caspase 3 (cleaved) (Biocare (Pacheco, Calif.), #CP229A) at a 1:90 dilution in Da Vinci Green for one hour and stained on an DAKO Autostainer. Slides were exposed to the appropriate HRP labeled polymer for 30 min and DAB chromogen (Dako (Santa Clara, Calif.) for 5 min. Slides were counterstained with Hematoxylin (Fisher, Harris Modified Hematoxylin), blued in 1% ammonium hydroxide, dehydrated, and mounted with Acrymount. Consecutive sections with the primary antibody omitted were used as negative controls. The sections were evaluated in a blinded fashion by a board certified pathologist.

Statistics

All statistical analyses were performed using Prism version 6.0c (GraphPad Software, La Jolla, Calif.). Statistical significance was defined as P<0.05. Statistical analysis of differences in tumor volumes between the control and drug-treated animal groups was performed by Mann-Whitney U test. A long-rank (Mantel-Cox) test was used for determining the statistical significances in event-free survival differences of animals between treatments. Statistical analysis for correlation was performed using Spearman's correlation analysis with two-tailed P values and 95% confidence interval. A Student's unpaired t test, two-tailed, was used for statistical analysis of in vitro data. As part of the standard unpaired t test analysis, GraphPad Prism tests the assumption that the variance between the groups is identical using a F test.

A Chemical Library Screen for Small Molecules that Bind to CD99 with Selective Growth Inhibitory Activity in ES Cells A set of 2,607 compounds representing diverse molecular structural classes from the Developmental Therapeutics Program, the National Cancer Institute (The NCI/DTP Open Chemical Repository at https://dtp.cancer.gov) was screened to identify small molecules that directly bind to the purified CD99 protein with selective growth-inhibitory activity against ES cell lines. A summary of the screening approach is given in FIG. 1.

Figure 3A:
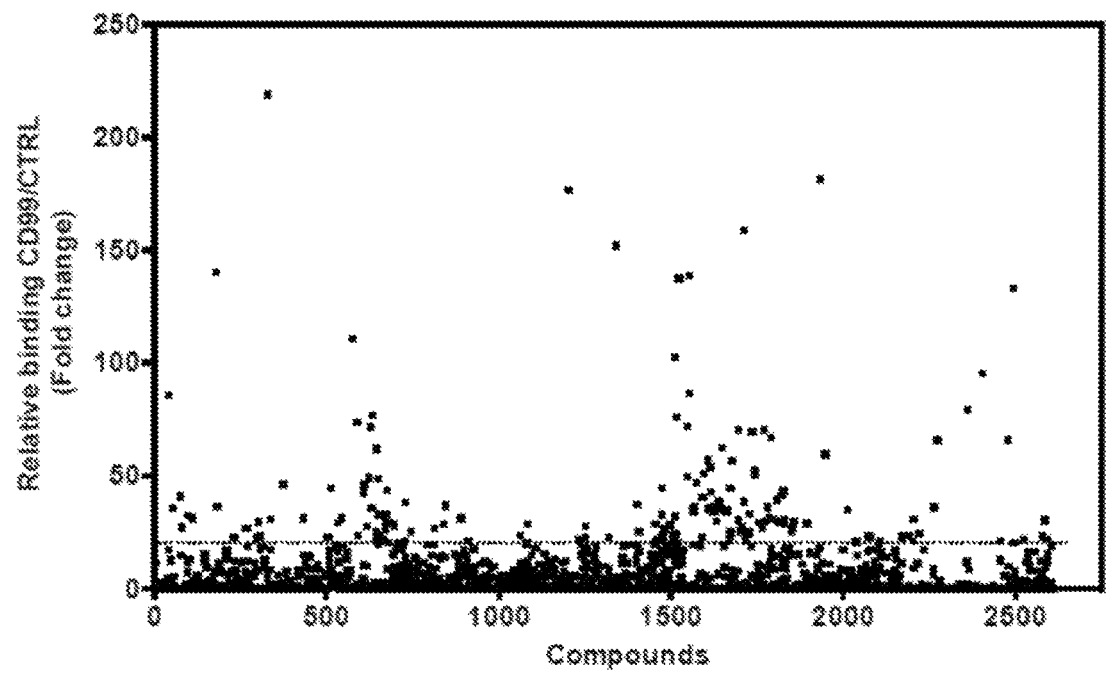
FIGS. 3A-D show screening of small molecule libraries for inhibitors of CD99-ECD.
Figure 3B:
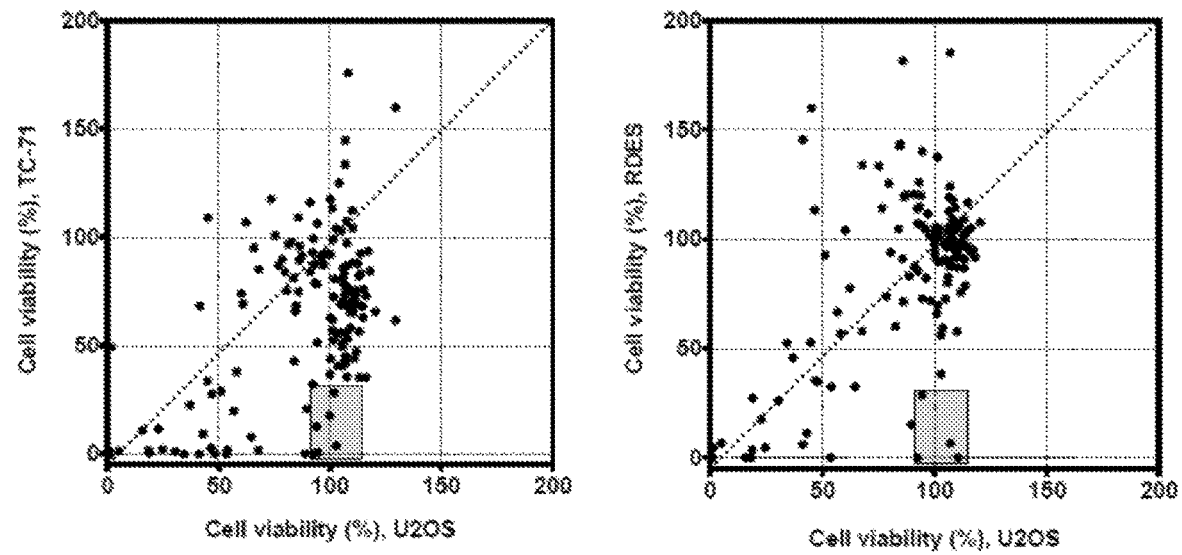

The primary screen was based on a direct binding assay using surface plasmon resonance (SPR) technology with purified extracellular domain of CD99 (CD99-ECD) protein that was immobilized on a neutravidin-coated sensor chip. Recombinant CD99-ECD was prepared from *Escherichia coli* in a highly purified form as a fusion protein with N-terminal Bioease and C-terminal 6×His tags (FIG. 2A, left panel). The purified protein was analyzed to check the biotinylation by immunoblotting using streptavidin-HRP (FIG. 2A, right panel). SPR analysis confirmed that CD99-ECD protein made in bacteria was recognized by monoclonal antibodies, indicating that antigenic determinant sites were preserved (FIG. 2B). A negative control protein was used in order to eliminate non-specific binders. Compounds with a CD99 binding level higher than 20% of $R_{max}$ (the analyte binding capacity or theoretical maximum response)

were included for hit selection. Primary hits were then defined as compounds that showed at least 20-fold difference in binding to CD99 over negative control protein (FIG. 3A). 160 compounds that passed hit selection criteria were further tested in a secondary functional screen to prioritize functionally relevant compounds having higher specificity towards ES. Compounds were evaluated based on their ability to inhibit cell proliferation at 10 µmol/L concentration following 48 h incubation period in ES cell lines RDES and TC-71, which express high levels of CD99 and show reduced growth response to CD99 blocking antibody treatment. A negative control cell line U-2 OS cells that express low levels of CD99 and are resistant to CD99 blocking antibodies was also used. While a majority of the compounds did not show any cytotoxicity, some compounds killed both ES and OS cells (FIG. 3B). From this screen, 2 compounds were identified as secondary hits (NSC606860 and NSC662825), which inhibited the growth of ES cell lines by ≥70%, and OS cell lines by ≤10% (FIG. 1 and FIG. 3B). Dose-response studies were performed with 2 compounds at 1, 3, 10 and 30 µmol/L concentration in ES cell lines. Two compounds, NSC105014 (cladribine) and NSC606869 (clofarabine, Clolar®) exhibited highest selective antiproliferative activity against ES cells compared with U-2 OS cells as shown by an $IC_{50}$ value lower than 1 µmol/L compared to 9 µmol/L of NSC662825 (FIG. 1). Therefore, clofarabine was selected over NSC662825 as the main lead compound. Furthermore, NSC105014 (cladribine, Leustatin®), another FDA-approved adenosine nucleoside analog, with high structural similarity to clofarabine that differ only by the absence of one fluorine atom, was present among 160 primary hits (FIG. 1). Cladribine exhibited some degree of selective cytotoxicity in secondary screening against ES cells, and a subsequent dose-dependent cytotoxicity assay revealed an $IC_{50}$ lower than 1 µmol/L for TC-71 and RD-ES cell lines too. For these reasons, cladribine was also included in many of the follow up studies.

Figure 3C:
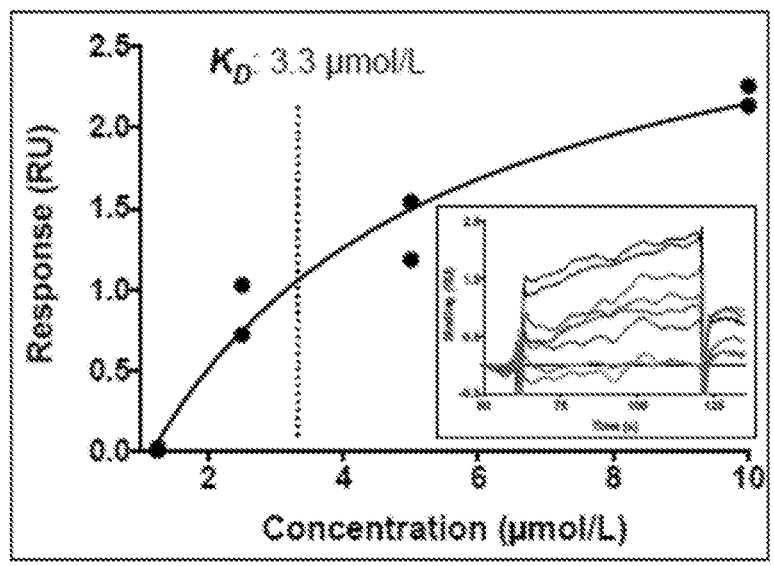
Figure 3D:
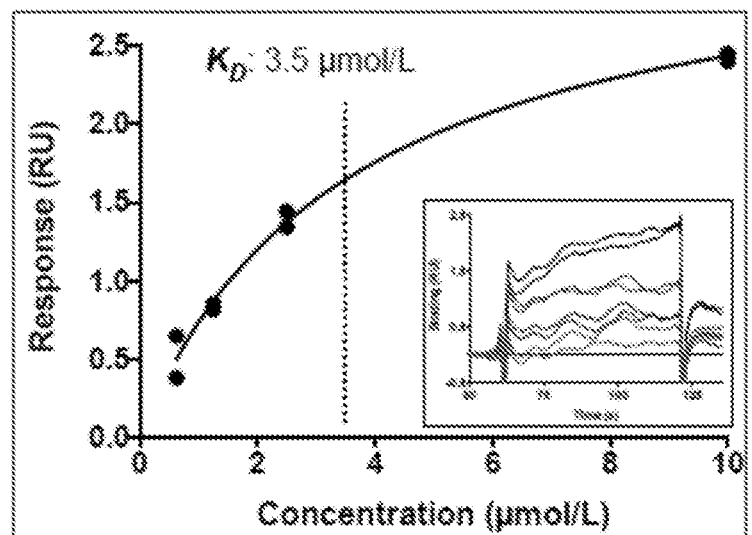

Clofarabine and Cladribine Directly Bind to CD99 and Selectively Inhibit the Growth of ES Cell Lines The binding affinity constants of clofarabine and cladribine for CD99 were determined by detailed SPR analysis using the recombinant human full-length CD99 expressed and purified from mammalian cells in a Biacore T200 instrument (FIGS. 3C and 3D). Titration of compounds onto immobilized CD99 yielded a $K_D$ value of 5.3±3.2 µmol/L (n=3 separate experiments) and 3.8±3.3 µmol/L (n=4 separate experiments) for clofarabine and cladribine, respectively. The use of properly folded and post-translationally modified CD99 protein produced in eukaryotic cells in binding assays is particularly more relevant for analysis of the protein-inhibitor interactions, given that CD99 is a heavily glycosylated protein. Analysis of binding kinetic data using CD99-ECD purified from bacteria also yielded comparable binding constants with $K_D$ values of 4.6±3.2 µmol/L (n=5 separate experiments) and 3.8±2.4 µmol/L (n=7 separate experiments), for clofarabine and cladribine, respectively, thereby validating the screening approach used herein.

Figure 4:
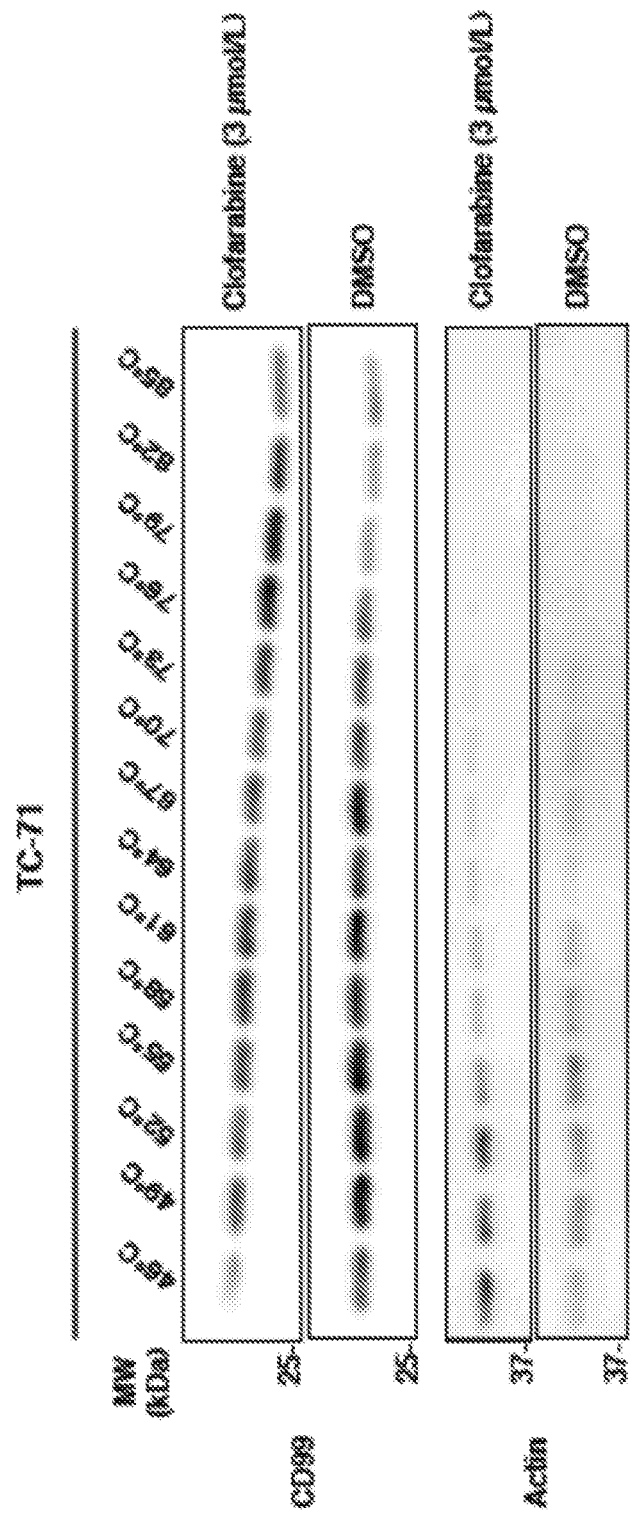
FIG. 4 shows that clofarabine increases the thermostability of CD99 protein in lysates at elevated temperatures, as shown by a cellular thermal shift assay (CETSA®). The total cell lysates from TC-71 cells were incubated with either vehicle (DMSO) control or 3.0 µmol/L clofarabine for 30 min at room temperature, followed by placing the lysates individually in tubes in a PCR machine for heating to a predefined temperature for 2 min. After temperature equilibration of the lysates for 2 min at room temperature, insoluble protein aggregates were removed by centrifugation, and the resulting supernatants were analyzed by immunoblotting for CD99 and actin.

The binding of clofarabine to CD99 in total cell lysates was also ascertained by using cellular thermal shift assay (CETSA). This method allows detection of drug-bound stabilized target protein in the solution at elevated temperatures unlike the unbound proteins, which denature and precipitate from the soluble protein fraction. The thermostability of endogenous CD99 protein increased in cell lysates from TC-71 cells incubated with clofarabine at high temperatures when compared to the control lysates, whereas such a response was not observed with the actin protein (FIG. 4).

Figure 5A:
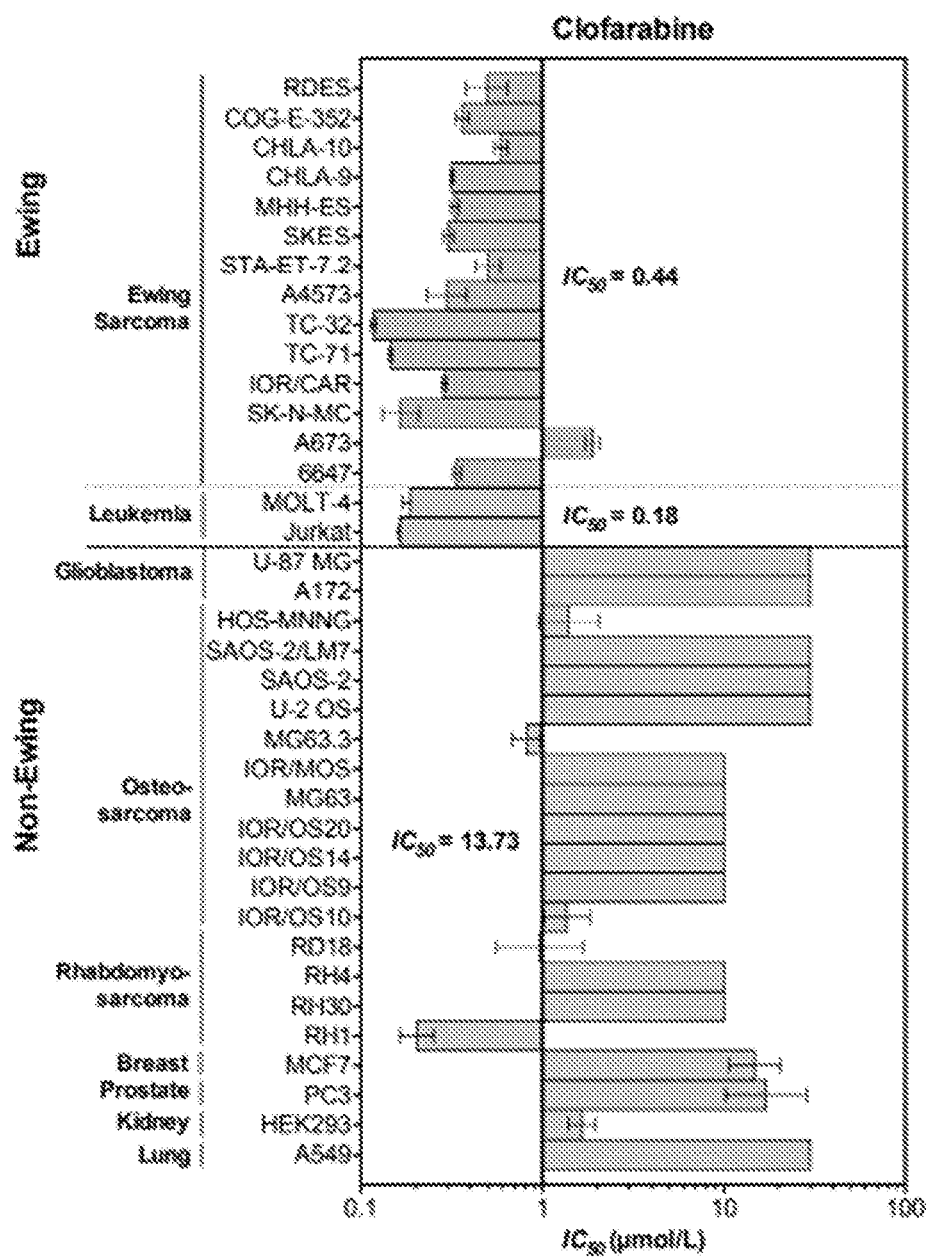
FIGS. 5A-B show that ES and leukemia cell lines are sensitive to clofarabine and cladribine. Cell viability was evaluated by WST-1 or MTT assay following 48 hour treatment with clofarabine (FIG. 5A) and cladribine (FIG. 5B). The $IC_{50}$ values were determined by nonlinear regression analysis using GraphPad Prism version 6.0 h software, or CalcuSyn software. The average $IC_{50}$ concentrations of clofarabine were 0.44±0.44 for ES, 0.18±0.01 for leukemia and 13.73±11.54 for non-ES cell lines. The average $IC_{50}$ concentrations of cladribine were 1.09±1.85 for ES, 0.34±0.03 for leukemia and 20.05±13.16 for non-ES cell lines. The average $IC_{50}$ concentration for non-ES cell lines was calculated using the highest concentrations tested (either 10 or 30 µmol/L) for resistant cell lines. Values are presented as the mean±SD of three technical replicates.
Figure 5B:
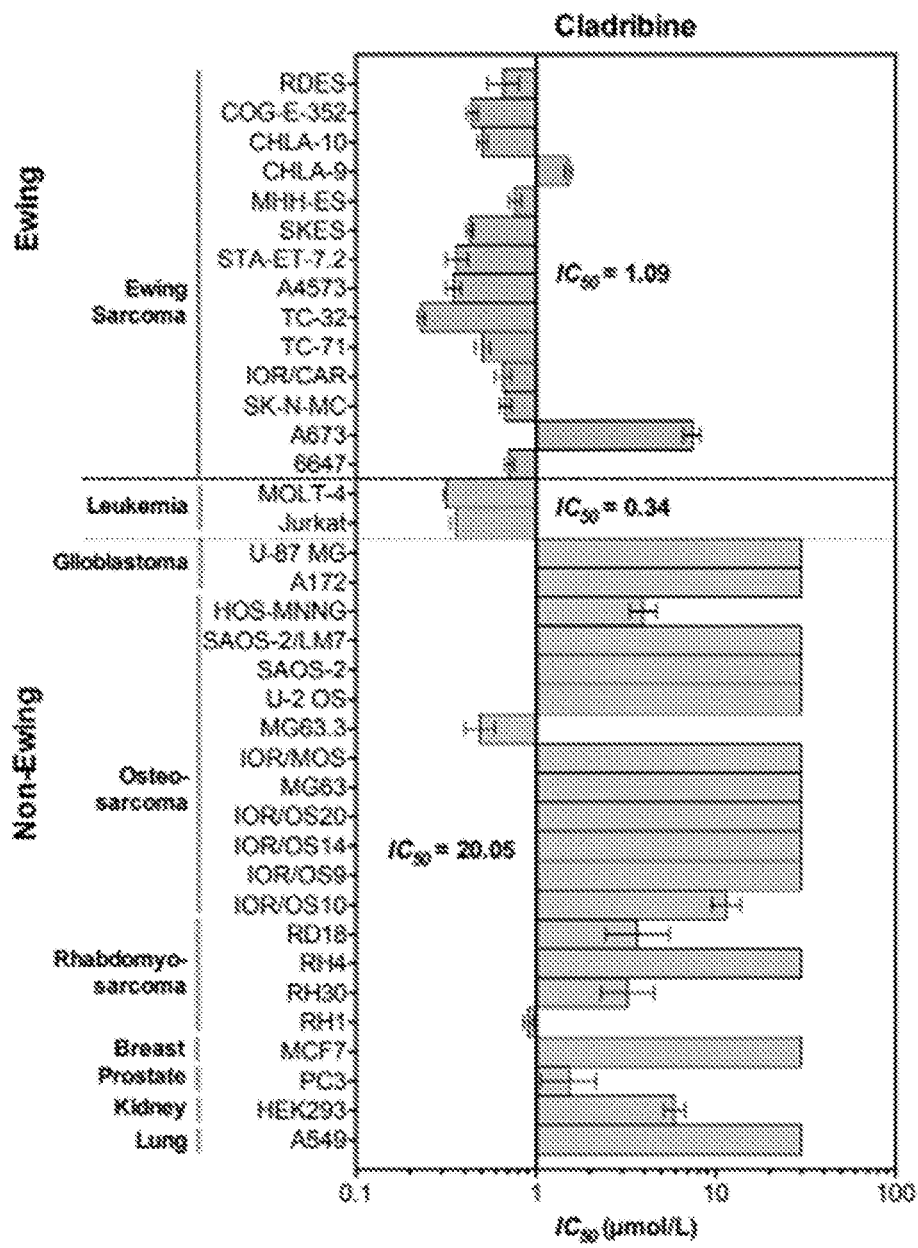

To further verify the selective cytotoxic activity of clofarabine and cladribine against ES, a detailed $IC_{50}$ analysis was performed on a panel of 14 ES cell lines and 28 non-ES cell lines, including 22 human cancer lines derived from 7 different tumor histotypes and HEK293 cell line (FIGS. 5A and B). Clofarabine and cladribine are approved by FDA for their use in patients with relapsed leukemia. Therefore, two leukemia cell lines, MOLT-4 and Jurkat, were included as positive controls in this experiment. Consistent with their clinical indications, both drugs inhibited the growth of leukemia cell lines with $IC_{50}$ of <1 µmol/L. Similar to leukemia cell lines, all ES cell lines, except for A673, which has a BRAF V600E mutation, were highly sensitive to both clofarabine and cladribine with $IC_{50}$ concentrations in the submicromolar range, and exhibited 31-fold and 18-fold increased sensitivity compared to non-ES cell lines, respectively.

CD99 Protein Expression Correlates with Clofarabine Sensitivity in Only ES Cells To investigate the relationship between the level of CD99 expression and drug sensitivity, the endogenous expression of CD99 was determined in a panel of 9 ES and 13 non-ES cell lines. The recombinant purified CD99-ECD protein was used to generate standard curves for immunoquantification of CD99 expression by immunoblotting (FIGS. 6B and 6C). A significant negative correlation was found between CD99 expression and $IC_{50}$ values for clofarabine (Spearman rho=−0.53, p=0.0120) and cladribine (Spearman rho=−0.56, p=0.0071) (FIGS. 6B and C). Cells with high CD99 expression had smaller $IC_{50}$ values and more sensitive to clofarabine and cladribine. Cells with low CD99 expression had bigger $IC_{50}$ values and less sensitive to clofarabine and cladribine. CD99 expression analysis of sarcoma cell lines by flow cytometry in a panel of 7 ES, 8 OS and 4 rhabdomyosarcoma cell lines and the subsequent correlation analysis also produced significant negative correlations for clofarabine and cladribine (Table 1).

TABLE 1

Correlation between CD99 protein levels and $IC_{50}$ values for cladribine and clofarabine in Ewing sarcoma (ES) cells, osteosarcoma (OS) and rhabdomyosarcoma (RM) cancer cells

| Tumor histotype | Cell lines | Cladribine $IC_{50}$ (µmol/L) | Clofarabine $IC_{50}$ (µmol/L) | CD99 expression (log mean intensity) |
| --- | --- | --- | --- | --- |
| ES | 6647 | 0.71 | 0.34 | 154.9 |
|  | A673 | 7.42 | 1.90 | 88.4 |
|  | SK-N-MC | 0.68 | 0.17 | 46.5 |
|  | SKES-1 | 0.43 | 0.30 | 55.8 |
|  | RDES | 0.66 | 0.49 | 117.9 |
|  | TC-71 | 0.50 | 0.15 | 57.1 |
|  | IOR/CAR | 0.66 | 0.29 | 104.2 |
| OS | IOR/OS10 | 11.4 | 1.37 | 7.9 |
|  | IOR/OS9 | >30 | >10 | 12.0 |
|  | IOR/OS14 | >30 | >10 | 10.5 |
|  | SAOS-2 | >30 | >30 | 17.2 |
|  | U-2-OS | >30 | >30 | 10.4 |
|  | IOR/OS20 | >30 | >10 | 41.5 |
|  | MG63 | >30 | >10 | 31.3 |
|  | IOR/MOS | >30 | >10 | 38.9 |

TABLE 1-continued

Correlation between CD99 protein levels and IC$_{50}$ values for cladribine and clofarabine in Ewing sarcoma (ES) cells, osteosarcoma (OS) and rhabdomyosarcoma (RM) cancer cells

| Tumor histotype | Cell lines | Cladribine IC$_{50}$ (μmol/L) | Clofarabine IC$_{50}$ (μmol/L) | CD99 expression (log mean intensity) |
|---|---|---|---|---|
| RM | RH1 | 0.90 | 0.20 | 52.1 |
|  | RH30 | 3.26 | >10 | 8.52 |
|  | RH4 | >30 | >10 | 8.70 |
|  | RD18 | 3.67 | 0.97 | 17.40 |
| Spearman correlation (r) |  | −0.65* | −0.65* |  |

*p < 0.05

The cytotoxicity of cladribine and clofarabine in TC-71 cells silenced for CD99 expression was determined. Two stable transfectants of TC-71 cell line, TC-CD99-shRNA #1 and TC-CD99-shRNA #2, were generated by using plasmids expressing either a shRNA targeting the 3' untranslated region (UTR) of CD99 or a scrambled shRNA control. CD99 knockdown resulted in increase of IC$_{50}$ values by 2.85- and 2.35-fold of cladribine and 3.70- and 1.63-fold of clofarabine in TC-CD99-shRNA #1 and TC-CD99-shRNA #2, respectively, compared with TC-71 parental cells (Table 2). These findings validate the functional involvement of CD99 as target of clofarabine and cladribine in ES cells.

TABLE 2

Fold changes in IC$_{50}$ values of cladribine and clofarabine in TC-CD99-shRNA#1 and TC-CD99-shRNA#2 experimental models compared with TC-71 parental cells.

| Cell lines | Fold changes | |
|---|---|---|
|  | Cladribine | Clofarabine |
| TC-71 | 1.02 ± 0.27 (n = 5)* | 1.10 ± 0.38 (n = 8) |
| TC-CD99-shRNA #1 | 2.85 ± 1.13** (n = 4) | 3.70 ± 2.98** (n = 5) |
| TC-CD99-shRNA #2 | 2.35 ± 1.43 (n = 2) | 1.63 ± 0.54 (n = 5) |

IC$_{50}$ values were calculated by nonlinear regression analysis using CalcuSyn software (Biosoft).
*n indicates the number of biological replicates. The data are represented as the mean ± SD.
**p < 0.05; vs. TC-71 using a Student's unpaired t test.

Clofarabine and Cladribine Inhibit CD99 Dimerization and Downstream Signaling.

Figure 6A:
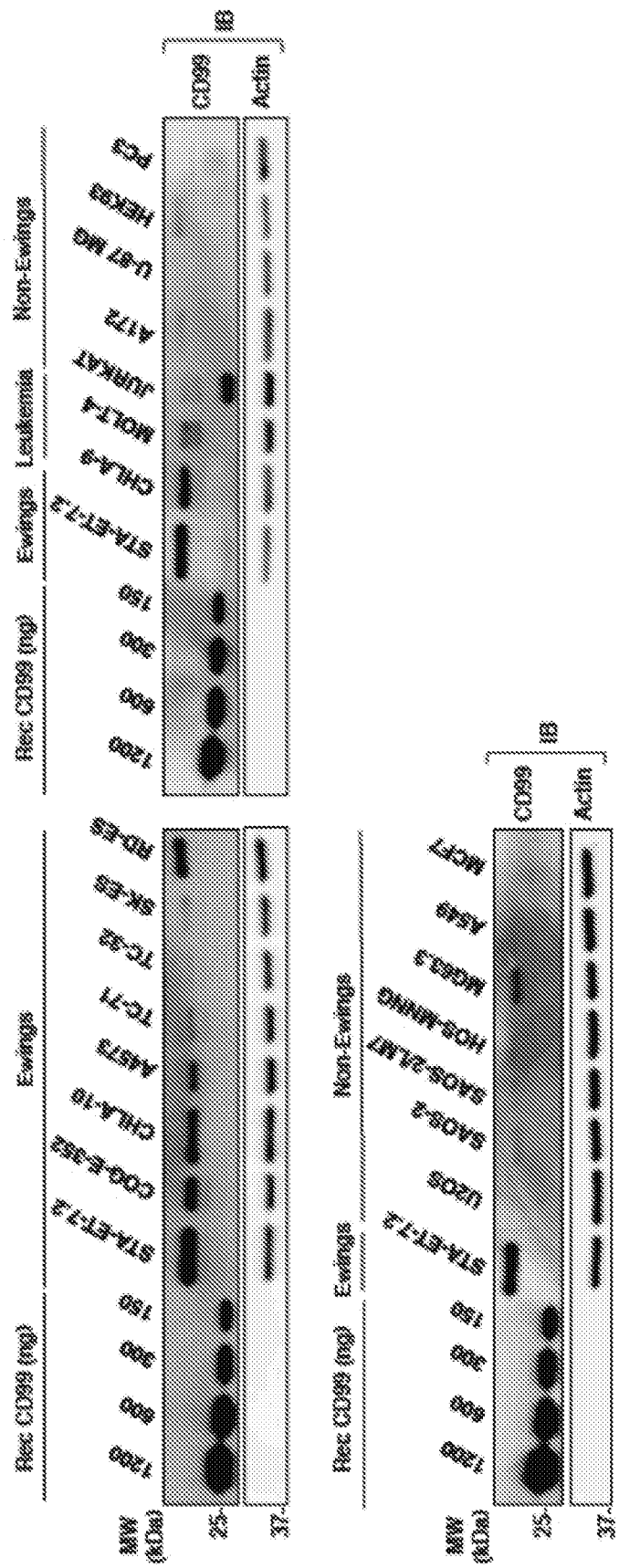
FIGS. 6A-C show that clofarabine and cladribine sensitivity correlates with CD99 levels in cancer cells.
Figure 6B:
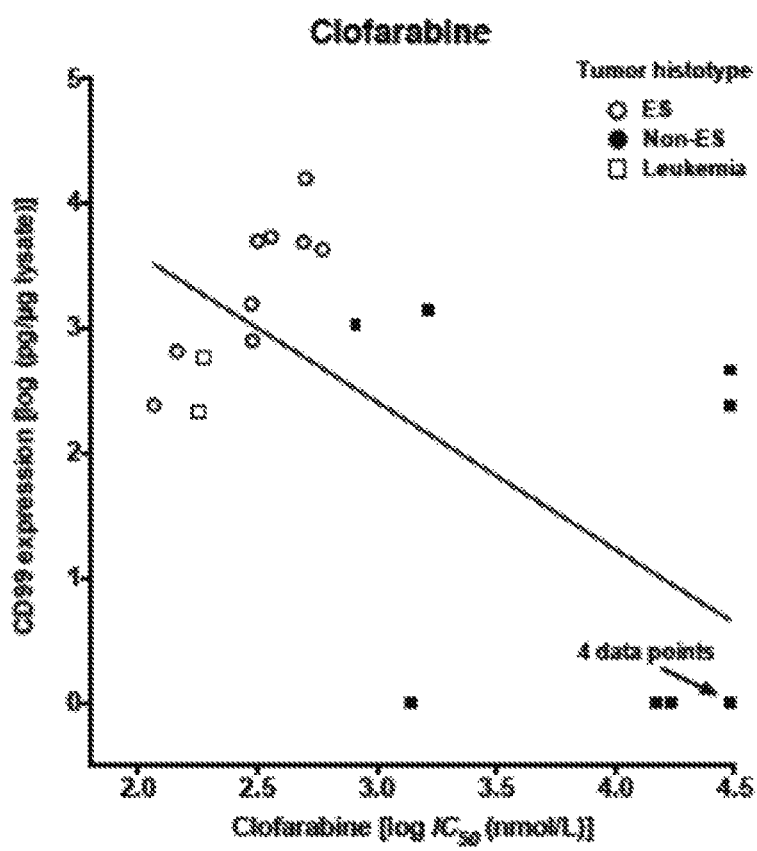
Figure 6C:
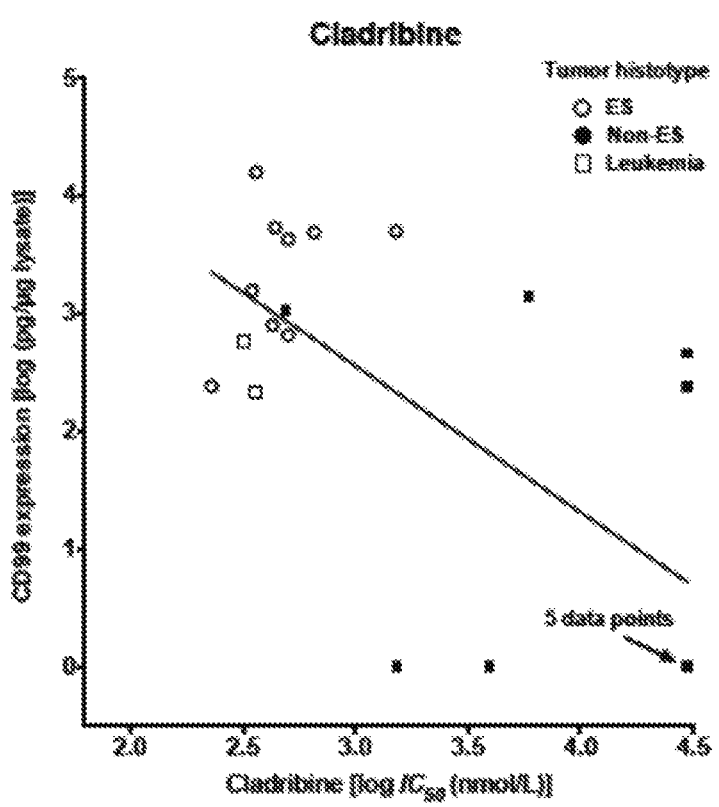
Figure 7A:
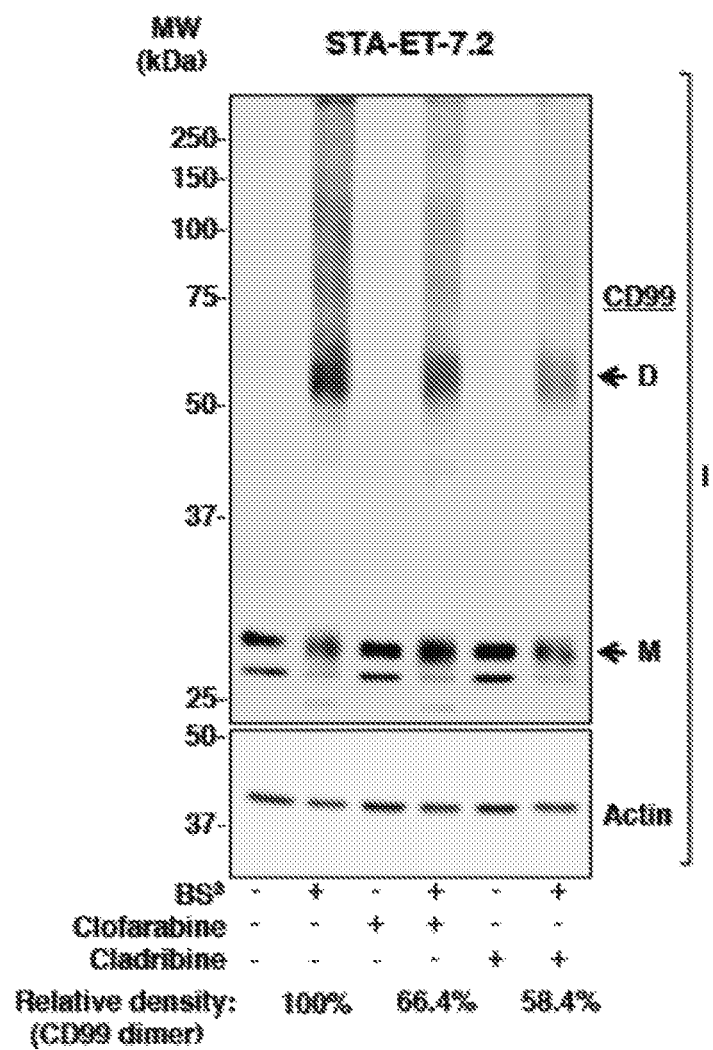
FIGS. 7A-D show that clofarabine and cladribine inhibit homodimer formation of CD99 and cyclophilin & PKA binding.

As CD99 could form homodimers through extracellular domain-mediated interactions and the homophilic CD99 interactions regulate transendothelial migration of immune cells, whether clofarabine and cladribine could block CD99 dimerization was examined in STA-ET-7.2 ES cells, which express the highest level of CD99 protein among all ES cell lines (FIG. 6A). To address this, in a chemical cross-linking assay, STA-ET-7.2 ES cells were preincubated with the inhibitors for 1 h at a final concentration of 5 μmol/L followed by the addition of 1 mmol/L BS$^3$, a membrane-impermeable chemical cross-linking agent. Immunoblot analysis demonstrated that cladribine significantly reduced the formation of CD99 homodimers. CD99 dimer formation was also blocked by treatment of the cells with clofarabine, albeit at a lower level than cladribine (FIG. 7A).

Figure 7B:
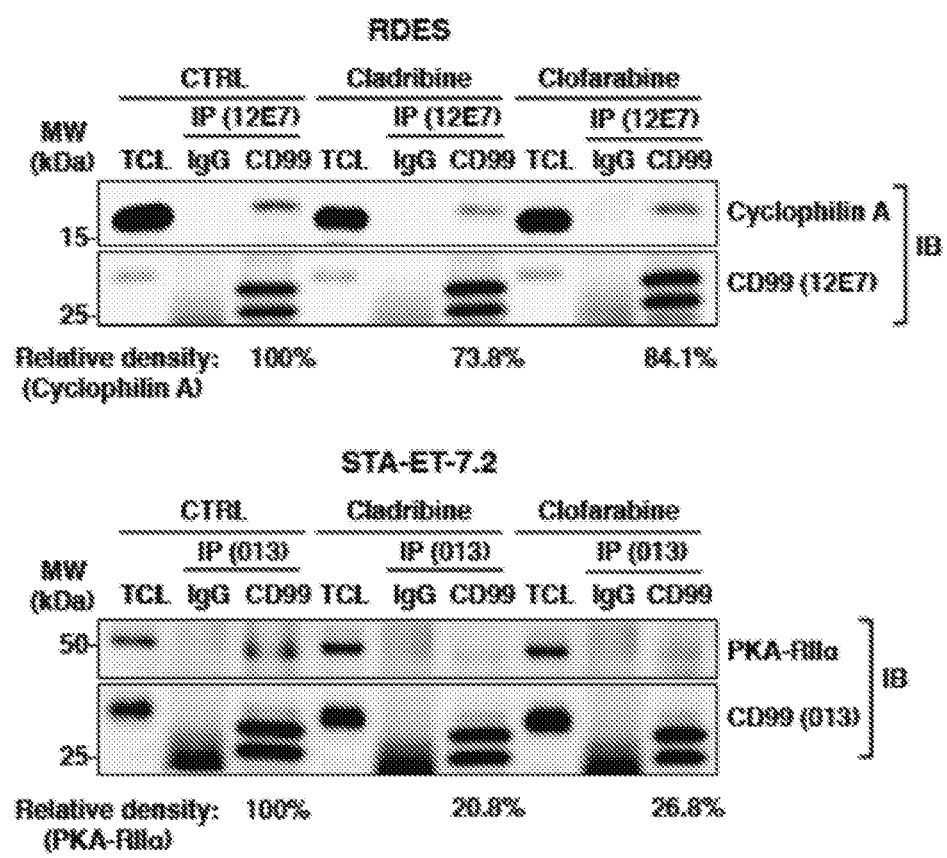

The interaction of CD99 with cyclophilin A and protein kinase A regulatory subunit IIα (PKA-RIIα) is implicated in downstream signaling pathways. Next, whether clofarabine and cladribine could block the interaction of CD99 with cyclophilin A and PKA-RIIα was determined. Endogenous CD99 was immunoprecipitated from RDES or STA-ET-7.2 ES cells and immunoblotted for CD99, cyclophilin A and PKA-RIIα. Consistent with the results of cross-linking experiments, the amount of coprecipitated cyclophilin A and PKARIIα proteins decreased significantly by cladribine and clofarabine (FIG. 7B).

Figure 8A:
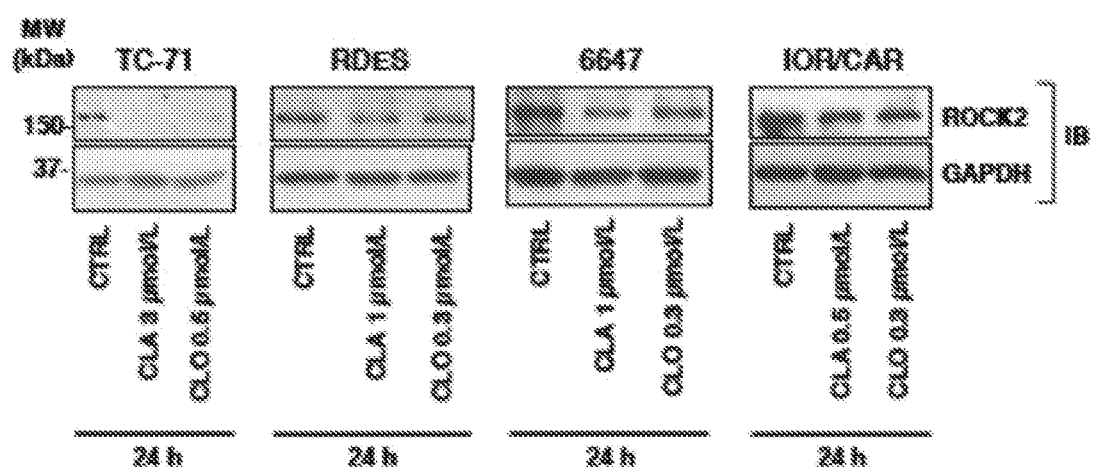
FIGS. 8A-C show that clofarabine and cladribine inhibit ROCK2 expression and the motility of ES cells.
Figure 8B:
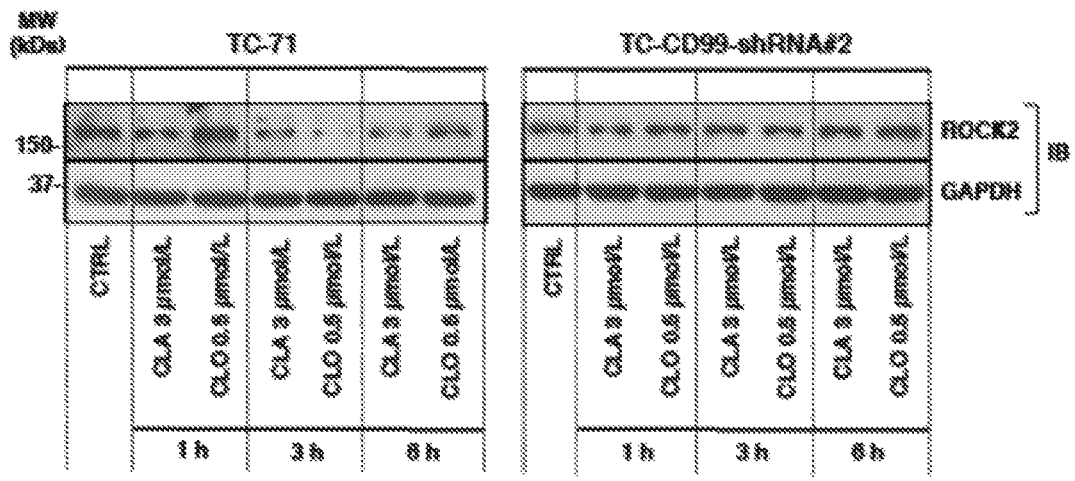
Figure 8C:
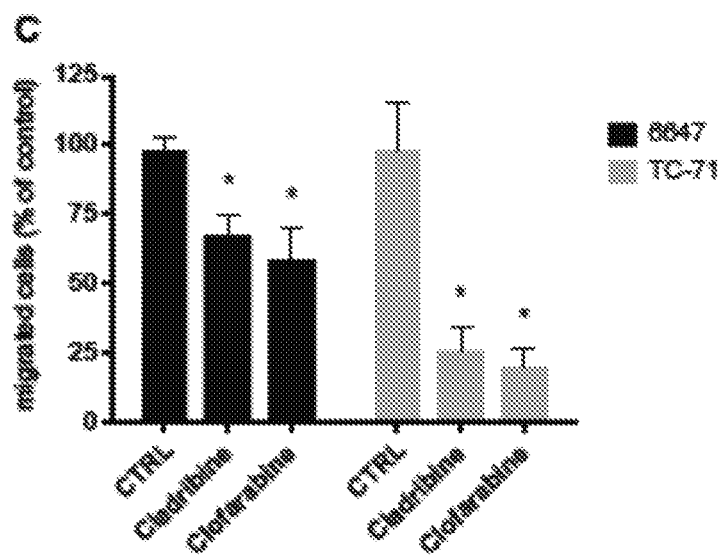

Clofarabine and Cladribine Inhibit ROCK2 Expression and the Motility of ES Cells ROCK2 is a key regulator of actin cytoskeletal remodeling and a crucial mediator of CD99-regulated cell adhesion and migration. Next, it was sought to determine whether pharmacological inhibition of CD99 could lead to a reduction in ROCK2 expression. RDES, 6647, IOR/CAR and TC-71 ES cells were treated with clofarabine and cladribine for 24 h. Immunoblot analysis showed that there was a notable decrease in ROCK2 expression in cells treated with either drug compared with DMSO-treated control cells (FIG. 8A). To ascertain the role of CD99 in drug-induced loss of ROCK2 expression, a loss-of-function approach was used. Knockdown of CD99 in TC-CD99-shRNA #2 cells abolished the inhibitory effect of drugs on ROCK2 expression, suggesting that the loss of ROCK2 expression by cladribine or clofarabine is mediated through CD99 signaling (FIG. 8B). The inhibitory effect of clofarabine and cladribine on the migration of 6647 and TC-71 ES cells by transwell migration assay was also determined. The cells were pre-treated with anti-CD99 compounds for 24 h followed by seeding of viable cells on the upper chamber. The number of migrated cells in the bottom chamber was significantly decreased when the cells exposed to either drug compared with control cells (FIG. 8C).

Figure 7C:
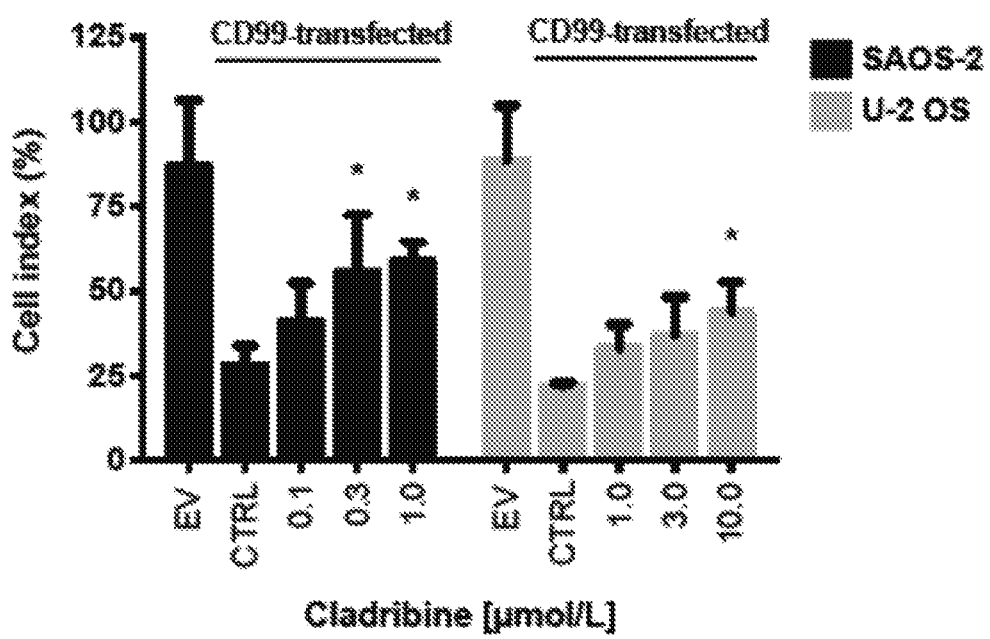
Figure 7D:
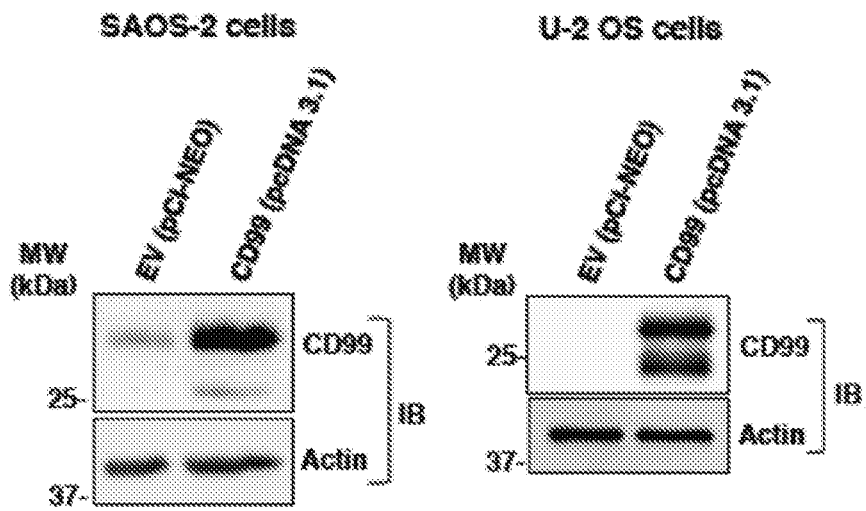
Figure 9:
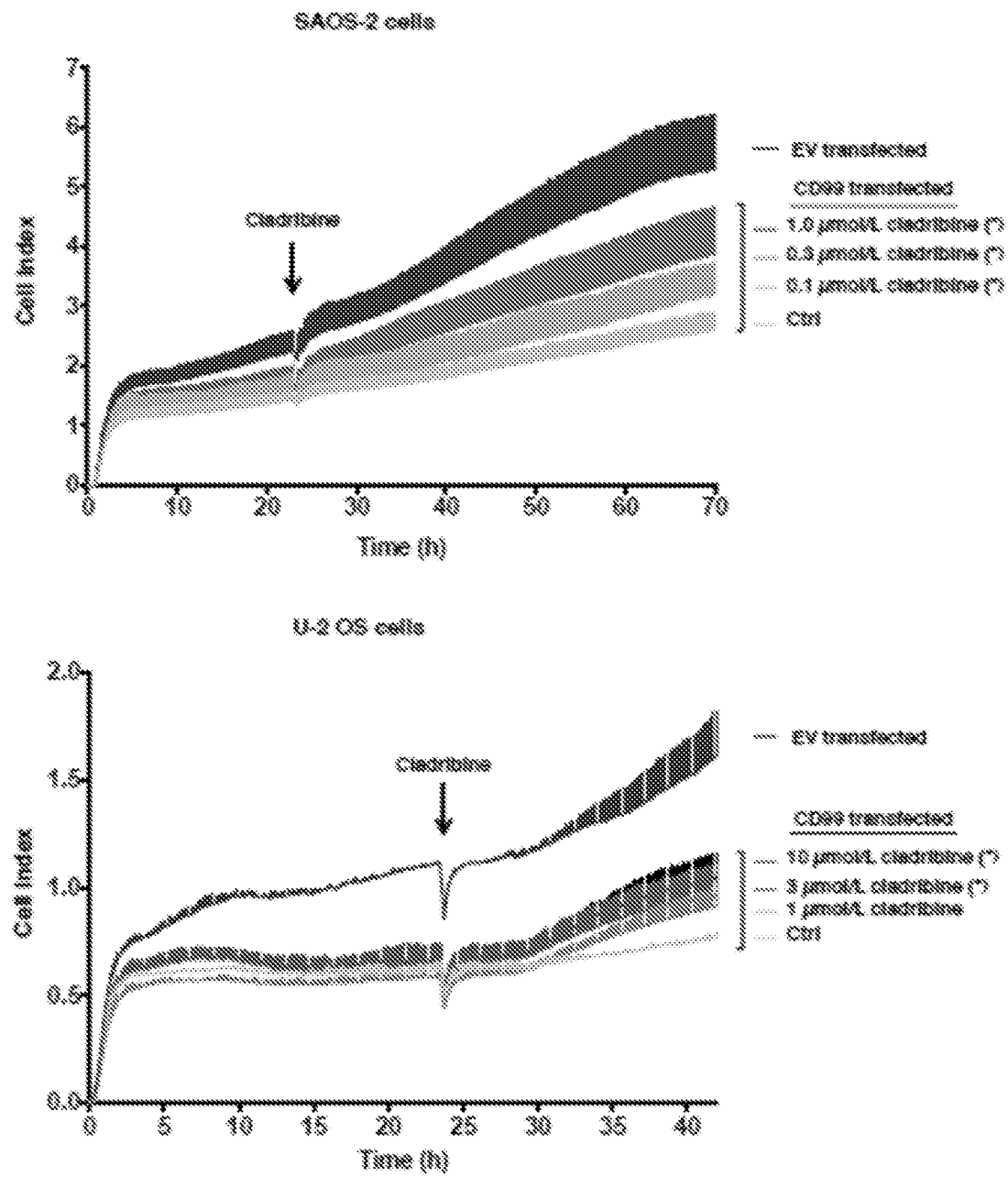
FIG. 9 shows that cladribine treatment of OS cells results in a rescue of reduced cell proliferation phenotype induced by CD99 expression. Real time proliferation curves for SAOS-2 (top panel) and U-2 OS cells (bottom panel) transfected with an empty vector (EV) or a vector expressing full length human CD99 in response to vehicle (DMSO) or cladribine treatment. The data, which are expressed as cell index, were generated using electrical impedance in xCELLigence RTCA instrument. The arrows show the time point when cladribine was added. Asterisks indicate statistically significant differences between treatments (ns, non-significant; *p<0.05; vs. CD99-transfected control using Student's unpaired t test test).

Cladribine Rescues Reduced Cell Proliferation Phenotype Induced by CD99 Expression in OS Cells OS cells express low levels of CD99 and the forced ectopic expression of CD99 reduces their growth. To test whether cladribine can rescue the reduced proliferation phenotype induced by overexpression of CD99, U-2 OS and SAOS-2 cells were transiently transfected with a mammalian expression vector containing cDNA encoding full length human CD99. As expected, CD99-forced expression suppressed cell proliferation compared with empty-vector transfected cells, which was rescued by the addition of cladribine in a dose-dependent manner (FIGS. 7C-D and FIG. 9). These results show that the growth-promoting effect of cladribine on SAOS-2 and U-2 OS cells is most likely due to the inhibition of CD99.

Figure 10A:
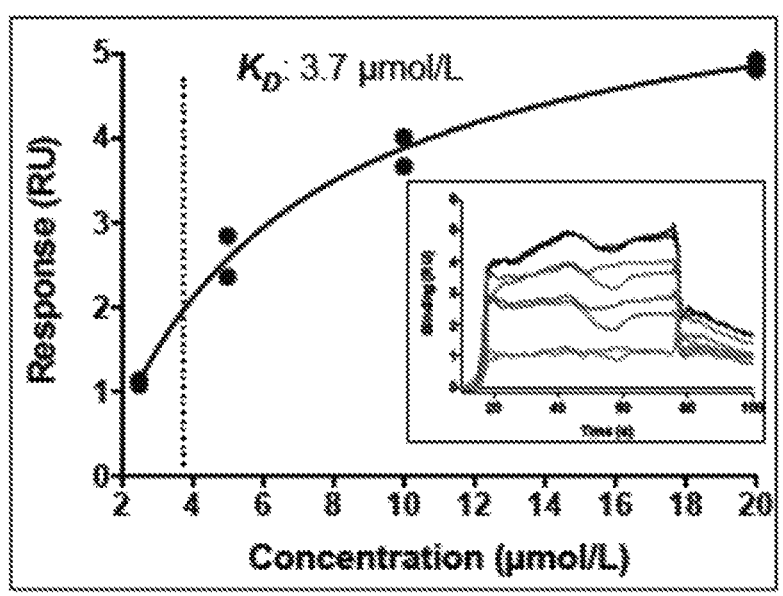
FIGS. 10A-D show that clofarabine can function through a mechanism involving CD99 inhibition other than inhibiting DNA synthesis.
Figure 10B:
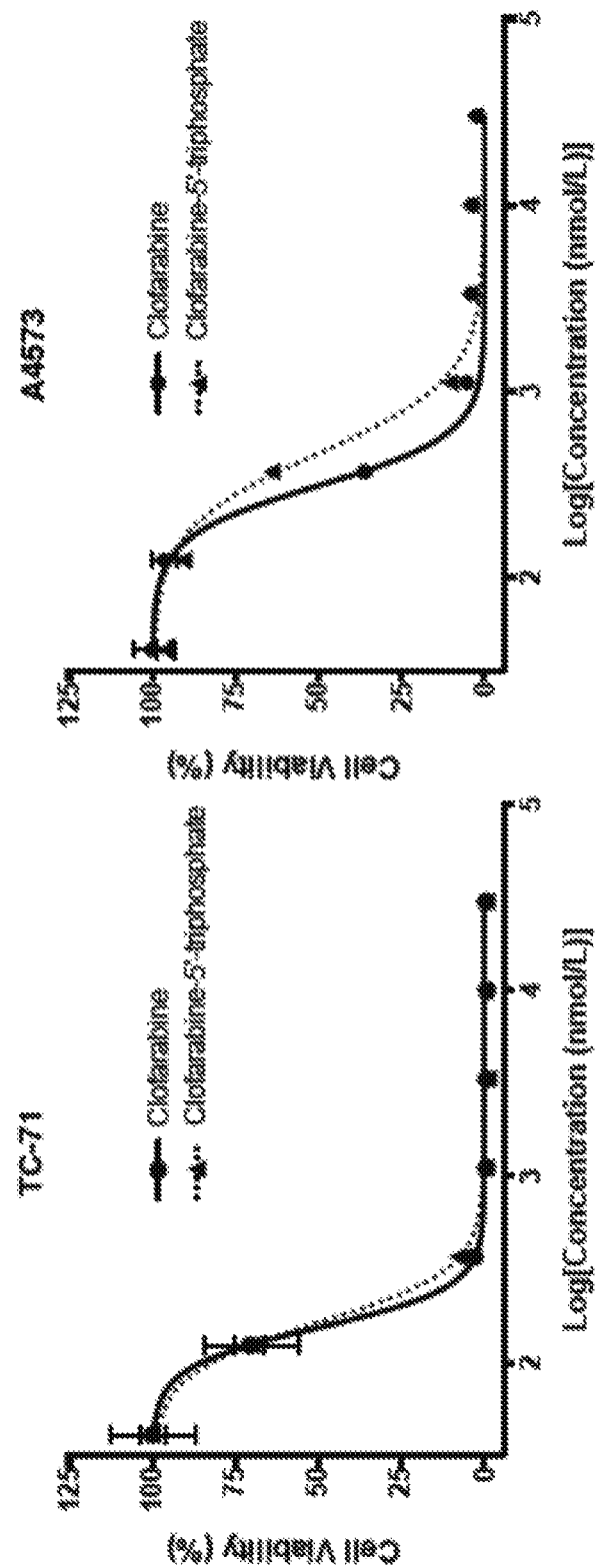

Membrane-Impermeable Analog of Clofarabine Shows Potent Cytotoxicity in ES Cells Nucleoside analogs exert their cytotoxic effects through disrupting DNA synthesis. It was hypothesized that a membrane-impermeable analog of clofarabine and cladribine could separate anti-CD99 activity from inhibition of DNA synthesis in ES cells. Because high polarity of phosphate moieties results in extremely poor, if any, membrane permeability, ES cells were treated with a triphosphate analog of clofarabine. The binding affinity of clofarabine-5'-triphosphate was determined for the recombinant human full-length CD99 expressed and purified from mammalian cells as 3.7 μmol/L by detailed SPR analysis (FIG. 10A). For the CD99-ECD purified from bacteria, the K$_D$ was calculated as 7.6 μmol/L. The dose-response curves showed that sensitivity of the ES cells to clofarabine and clofarabine-5'-triphosphate were highly similar with IC$_{50}$ concentrations of 0.15 and 0.17 μmol/L in TC-71 cells and 0.31 and 0.46 μmol/L in A4573 cells, respectively (FIG. 10B). Therefore, membrane-impermeable analogues of clofarabine and cladribine can function extracellularly by inhibiting CD99 to induce cell death in ES without affecting DNA synthesis.

Figure 10C:
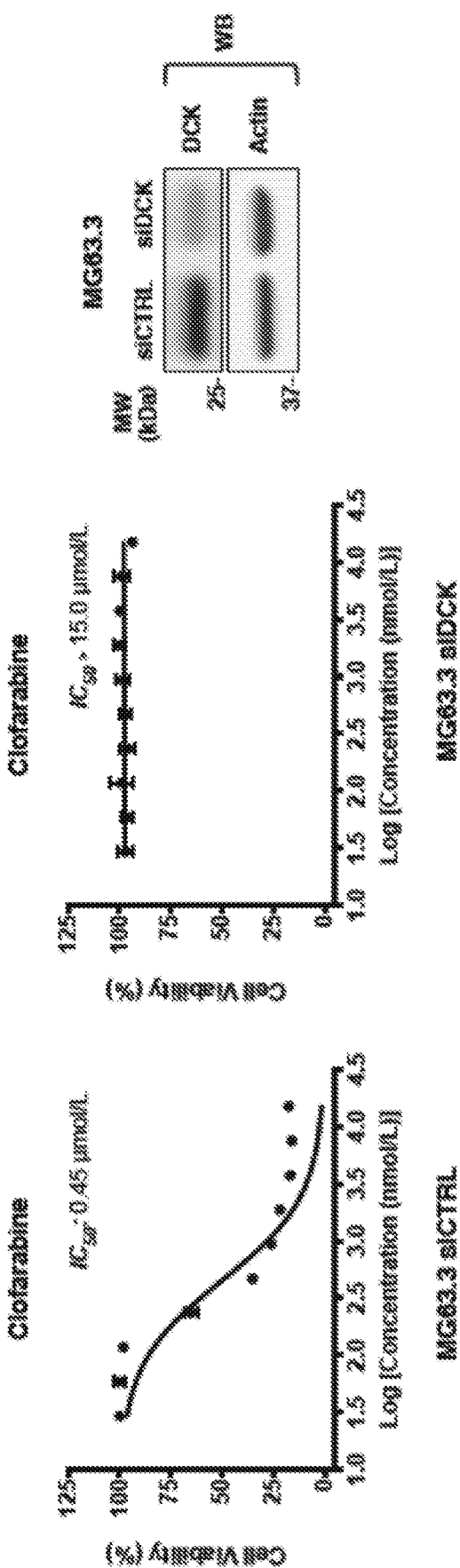
Figure 10D:
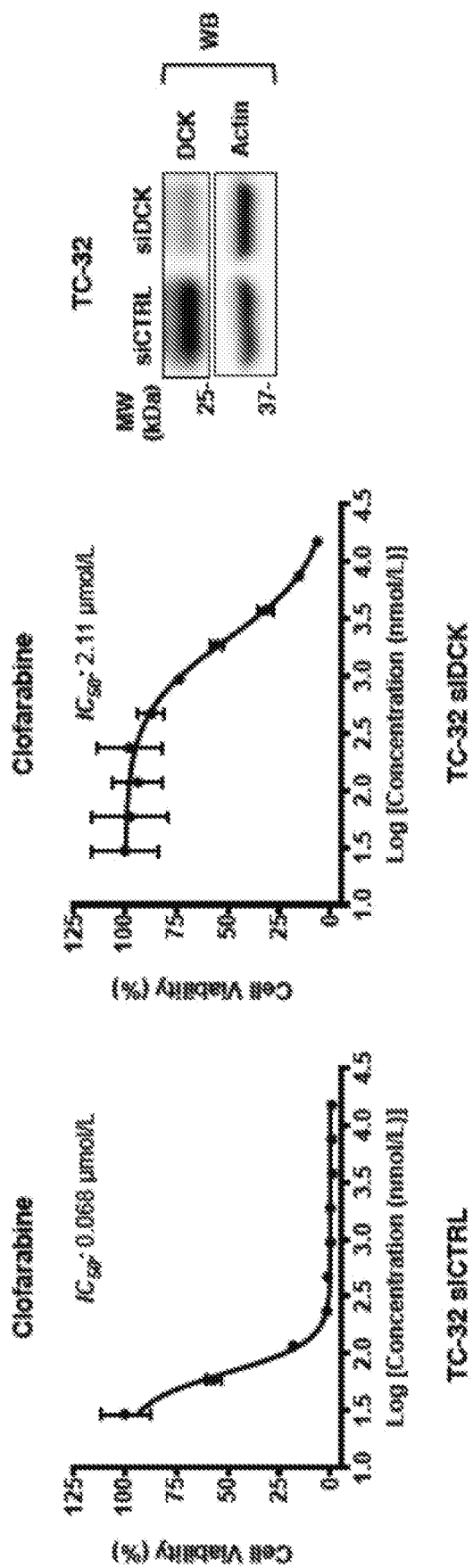

Clofarabine Functions Through a Mechanism Involving CD99 Inhibition in Addition to its Effects on DNA Metabolism Clofarabine and cladribine are prodrugs converted into their respective active metabolites, triphosphate forms, intracellularly by deoxycytidine kinase (DCK). In order to further validate the hypothesis that clofarabine and cladribine may also function by inhibiting CD99 other than inhibiting DNA synthesis, the expression of DCK was inhibited in ES and OS cell lines and their response to clofarabine was measured. In the OS cell line MG63.3, inhibiting DCK protein expression resulted in complete resistance to clofarabine, which suggest that the observed cell death in OS cells was entirely due to inhibition of DNA synthesis (FIG. 10C). In contrast, lack of DCK protein provided a shift to the right of the $IC_{50}$ curve in TC-32 cells (FIG. 10D), suggesting that the cell death observed in ES cells was a combined effect of both inhibition of DNA synthesis and CD99 function.

Figure 11A:
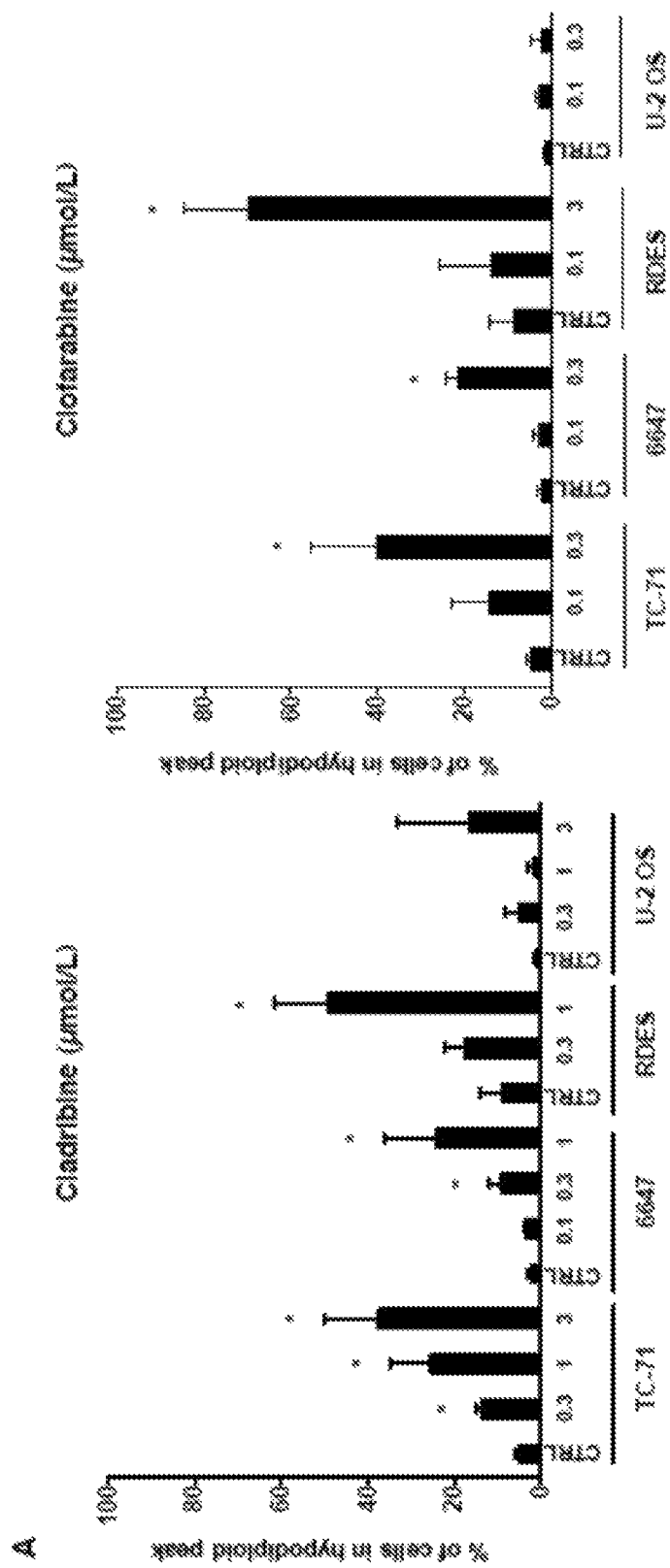
FIGS. 11A-C show that clofarabine and cladribine induce cell death and inhibit anchorage-independent cell growth in ES cells.
Figure 11B:
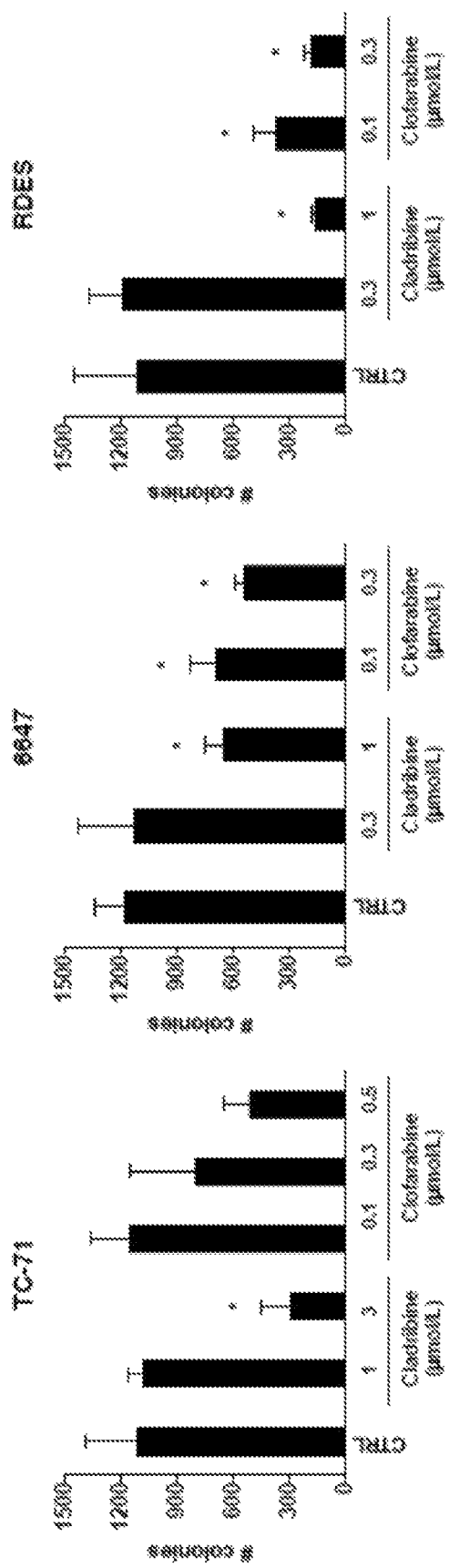
Figure 11C:
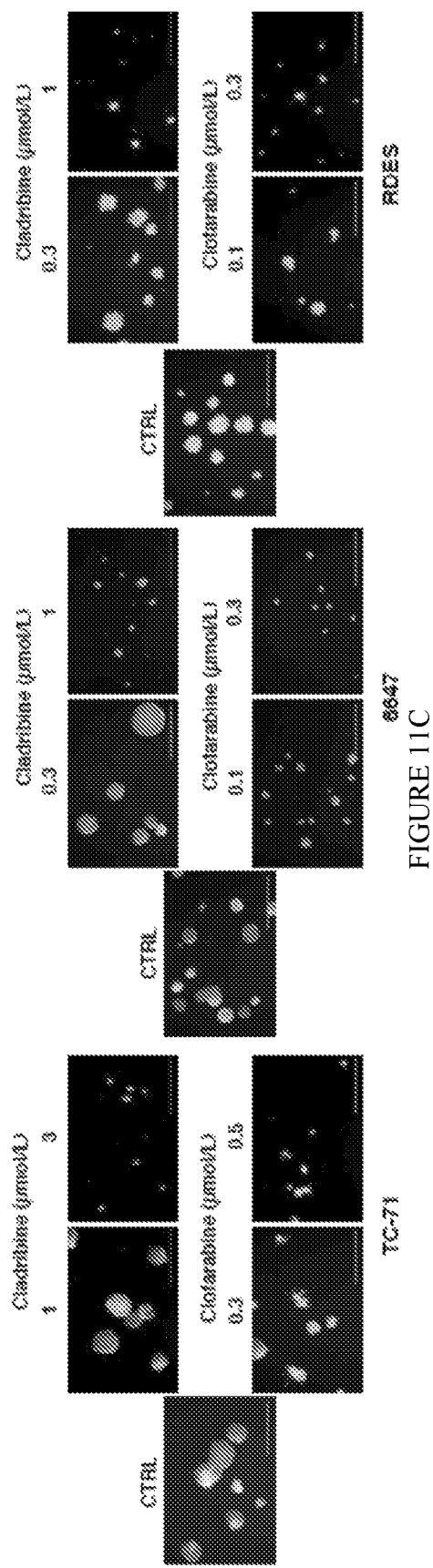

Clofarabine and Cladribine Suppress Anchorage-Independent Cell Growth and Inhibit Tumor Growth In Vivo A soft-agar colony formation assay was employed to examine the effects of CD99 inhibitors on the clonogenic survival/proliferation of cells under anchorage-independent conditions. Consistent with cell proliferation inhibition, both clofarabine and cladribine significantly inhibited colony formation of TC-71, 6647 and RDES ES cells in a dose-dependent manner (FIG. 11B-C).

To provide additional evidence that clofarabine inhibits anchorage-independent growth of ES cells through blocking CD99, TC-CD99-shRNA #1 and TC-CD99-shRNA #2 cells that showed increase of $IC_{50}$ values compared with TC-71 parental cells in regular culture conditions (Table 2) were evaluated. Both TC-CD99-shRNA #1 and TC-CD99-shRNA #2 formed fewer number of colonies compared to parental TC-71 cells (FIG. 12). However, treatment with clofarabine did not result in further decrease in colony formation of TC-CD99-shRNA #1 cells in soft-agar. This finding suggested that the lack of CD99 protein in TC-71 cells rendered them resistant to clofarabine.

Figure 12A:
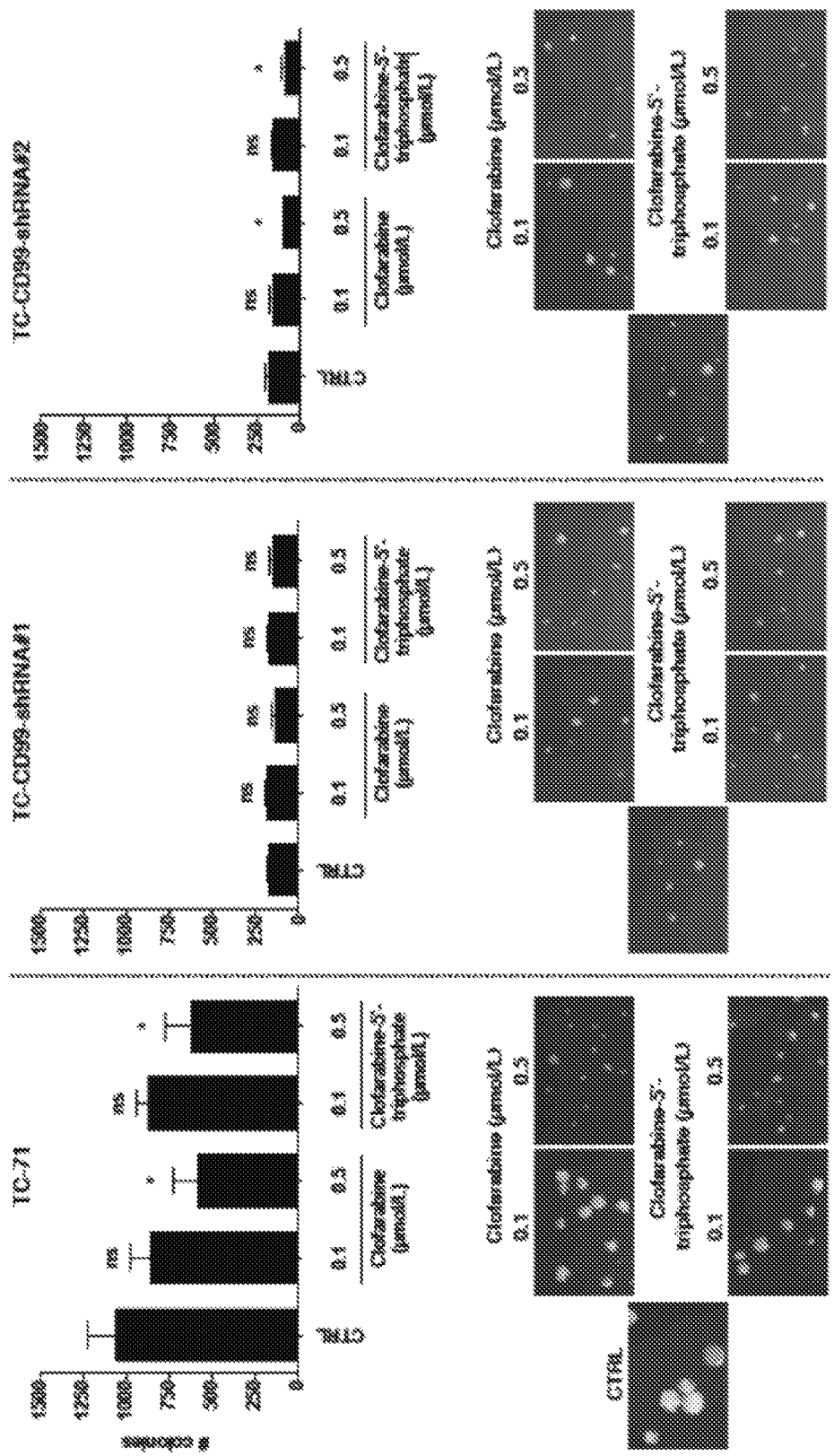
FIGS. 12A-B show that reduced CD99 expression renders ES cells resistant to clofarabine and clofarabine-5'-triphosphate in inhibition of anchorage-independent cell growth.
Figure 12B:
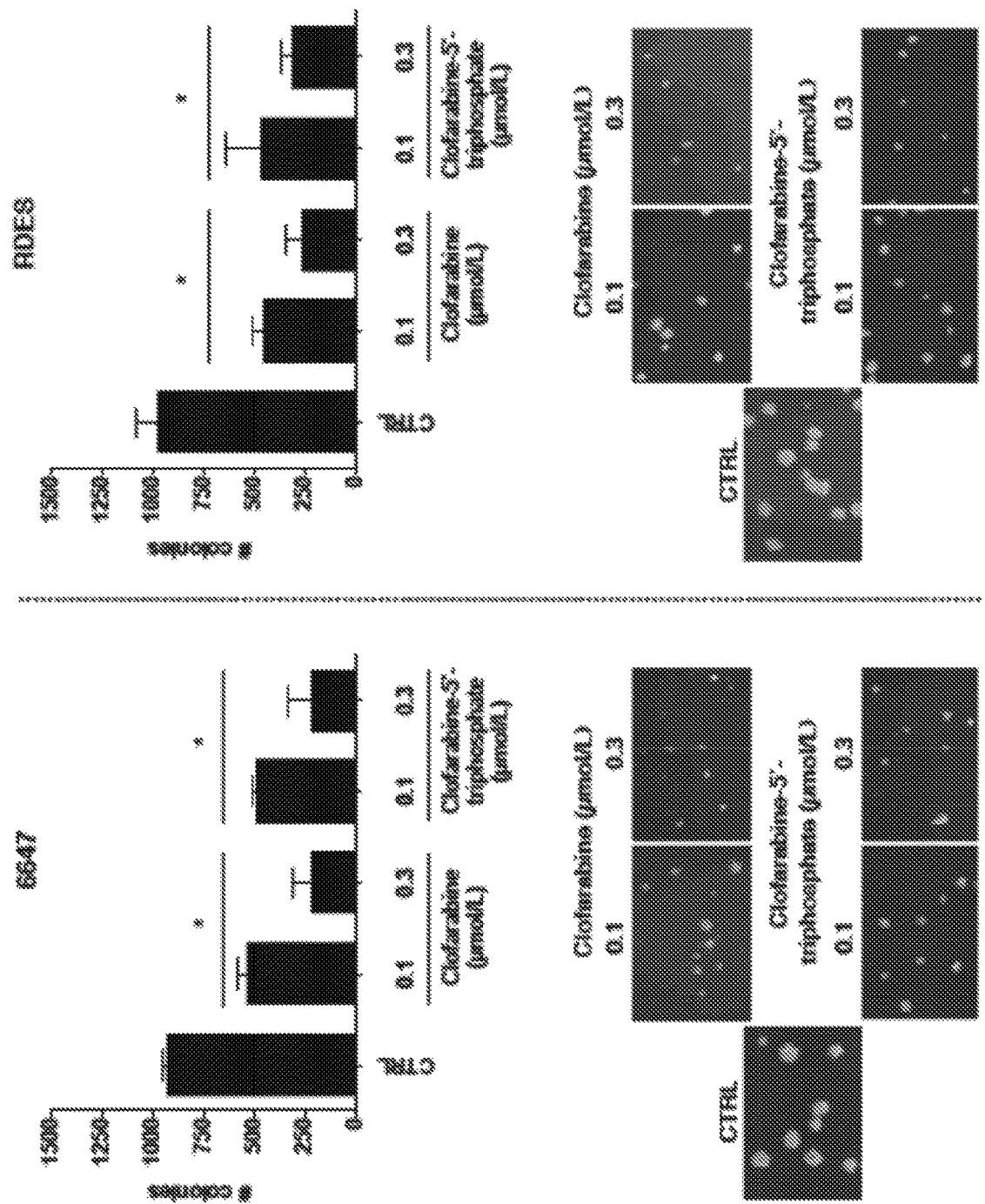

The effect of clofarabine-5'-triphosphate, which showed comparable cytotoxicity to clofarabine in normal culture conditions (FIG. 10B) was also evaluated. Clofarabine-5'-triphosphate inhibited the anchorage-independent growth of RDES, 6647 and TC-71 ES cells in a dose-dependent manner (FIGS. 12A and 12B). Similar to clofarabine, responsiveness of TC-CD99-shRNA #1 cells to clofarabine-5'-triphosphate in soft agar was diminished when CD99 expression was inhibited by an shRNA (FIG. 12A).

Clofarabine and Cladribine Inhibit Tumor Growth In Vivo

Figure 13:
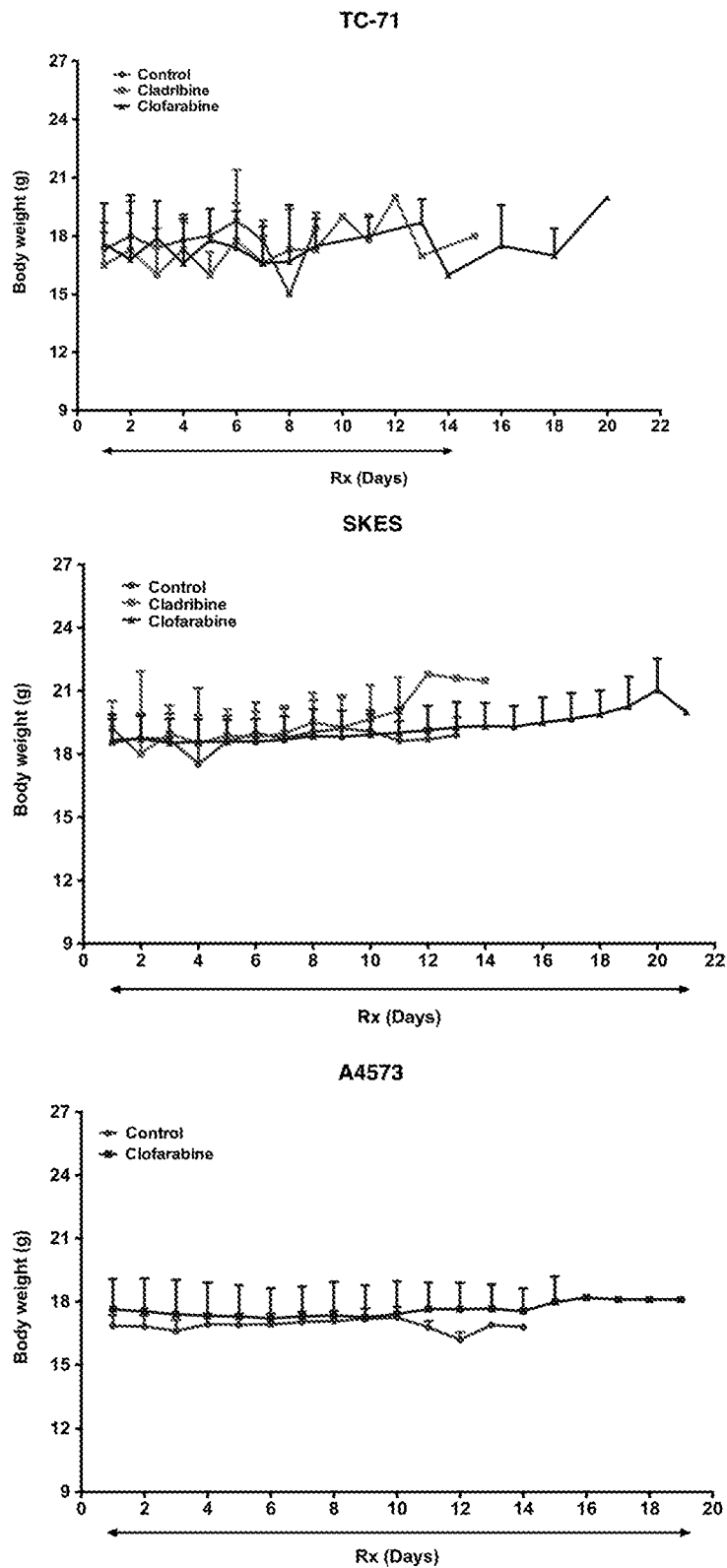
FIG. 13 shows that clofarabine and cladribine does not change total body weight during treatment. Mice in xenograft studies were weighed daily. Average body weight and S. D. in grams is given for each day for each experimental group. The horizontal arrow below the X-axis indicates those days that animals received treatment.
Figure 14A:
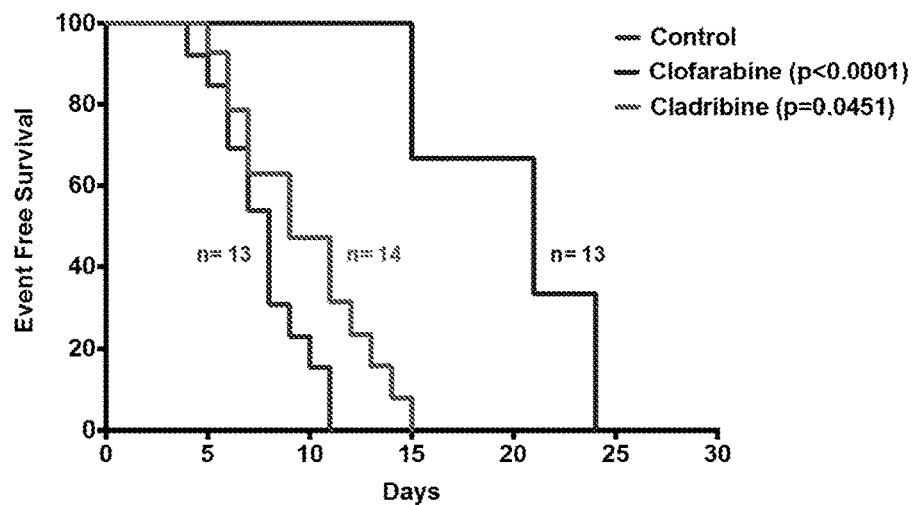
FIGS. 14A-C show that clofarabine significantly improves the event-free survival in orthotopic TC-71, SKES and A4573 xenograft mouse models of ES following intraperitoneal administration. SCID/beige mice bearing TC-71 (FIG. 14A), SKES (FIG. 14B) and A4573 (FIG. 14C) xenografts were treated daily with vehicle (DMSO) or CD99 inhibitors. TC-71 xenograft-bearing mice were given i.p. injections of clofarabine and cladribine at doses of 30 and 20 mg/kg, respectively, for 14 days. SKES xenograft-bearing mice were treated by i.p. injection with clofarabine and cladribine at 20 mg/kg doses for both, and mice carrying A4573 xenograft tumors were treated by i.p. injection with clofarabine at a 30 mg/kg dose for the study period. Tumors were measured each day. Kaplan-Meier event-free survival curves generated for clofarabine or cladribine treated-mice were compared with that of vehicle-treated mice. n indicates the number of mice per group. Statistically significances between treatments were calculated using long-rank (Mantel-Cox) test (*ns: non significant).
Figure 14B:
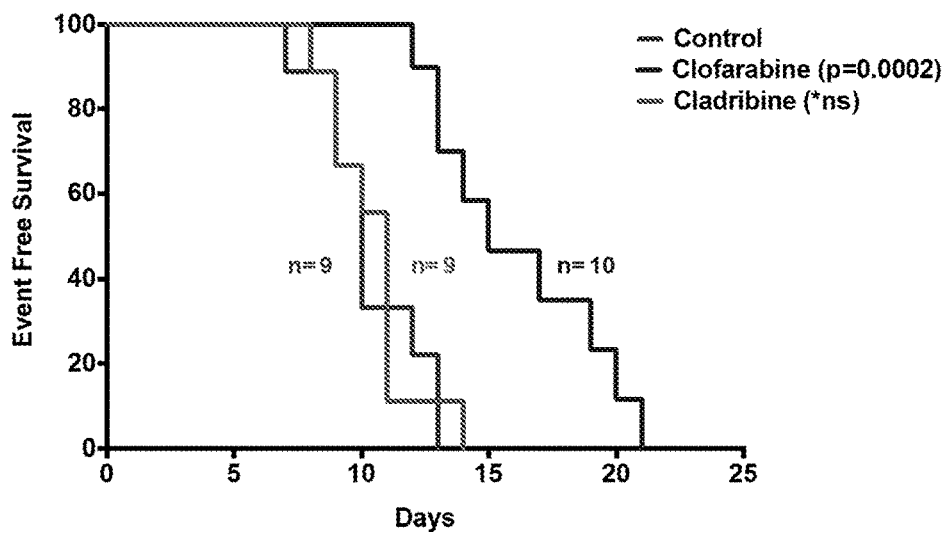
Figure 14C:
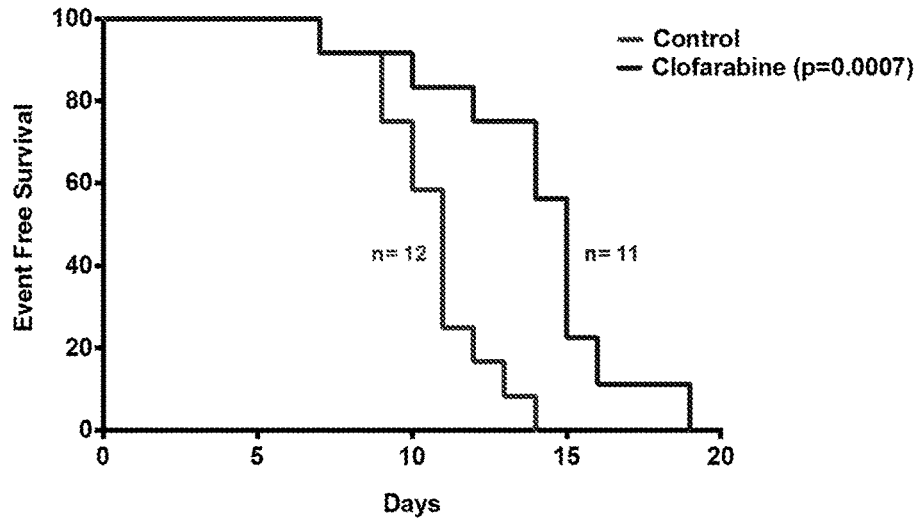
Figure 15A:
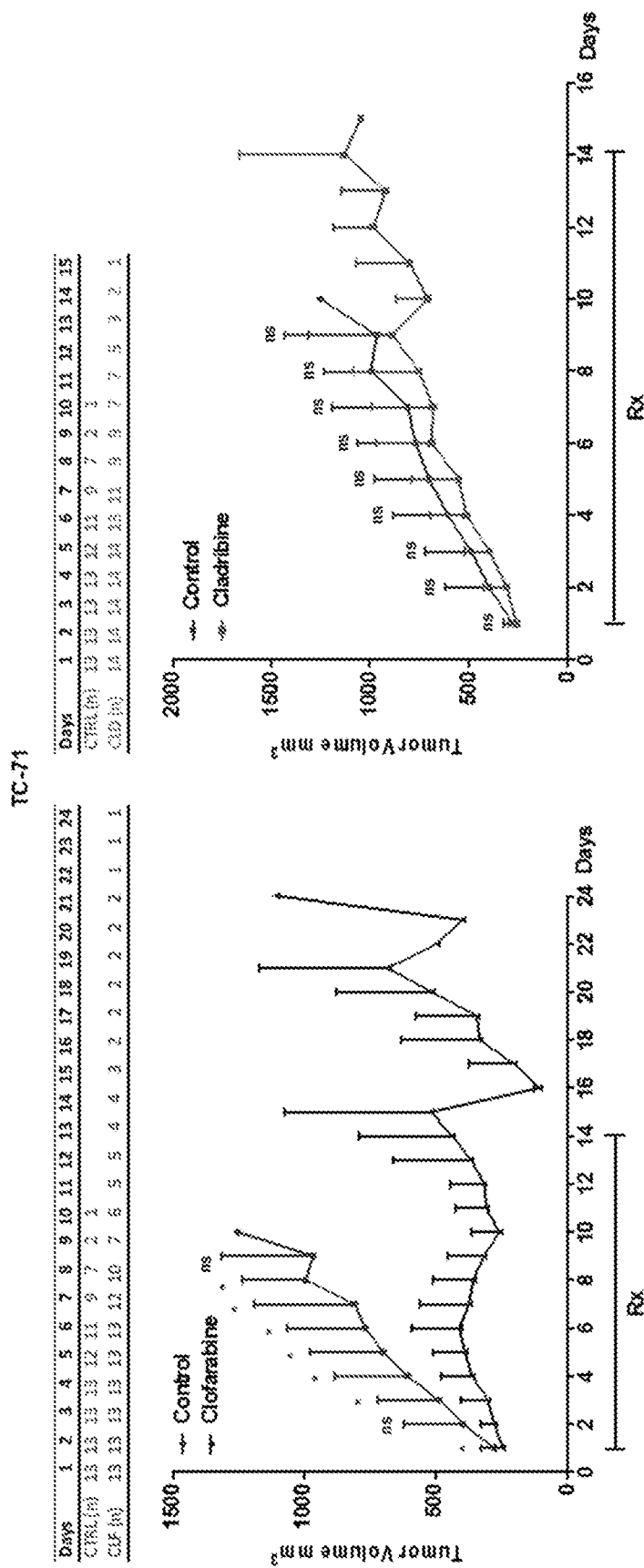
FIGS. 15A-C show that clofarabine administered intraperitoneally inhibits tumor growth in orthotopic TC-71, SKES and A4573 xenograft mouse models of ES. SCID/beige mice bearing TC-71 (FIG. 15A), SKES (FIG. 15B) and A4573 (FIG. 15C) xenografts were treated once daily with vehicle (DMSO), clofarabine or cladribine. TC-71 xenograft-bearing mice were given i.p. injections of clofarabine and cladribine at doses of 30 and 20 mg/kg, respectively, for 14 days. SKES xenograft-bearing mice were treated by i.p. injection with clofarabine and cladribine at 20 mg/kg doses for both, and mice carrying A4573 xenograft tumors were treated by i.p. injection with clofarabine at a 30 mg/kg dose for the indicated days. The bars on the bottom of the figures show the duration of the drug treatment. Tumors were measured each ay. The number of mice per group for each day throughout the study is given on top of each graph. The data are represented as the mean±SD. Asterisks indicate statistically significant differences between treatments (ns: non-significant; *p<0.05; vs. control using non-parametric Mann-Whitney U test, two-tailed).
Figure 15B:
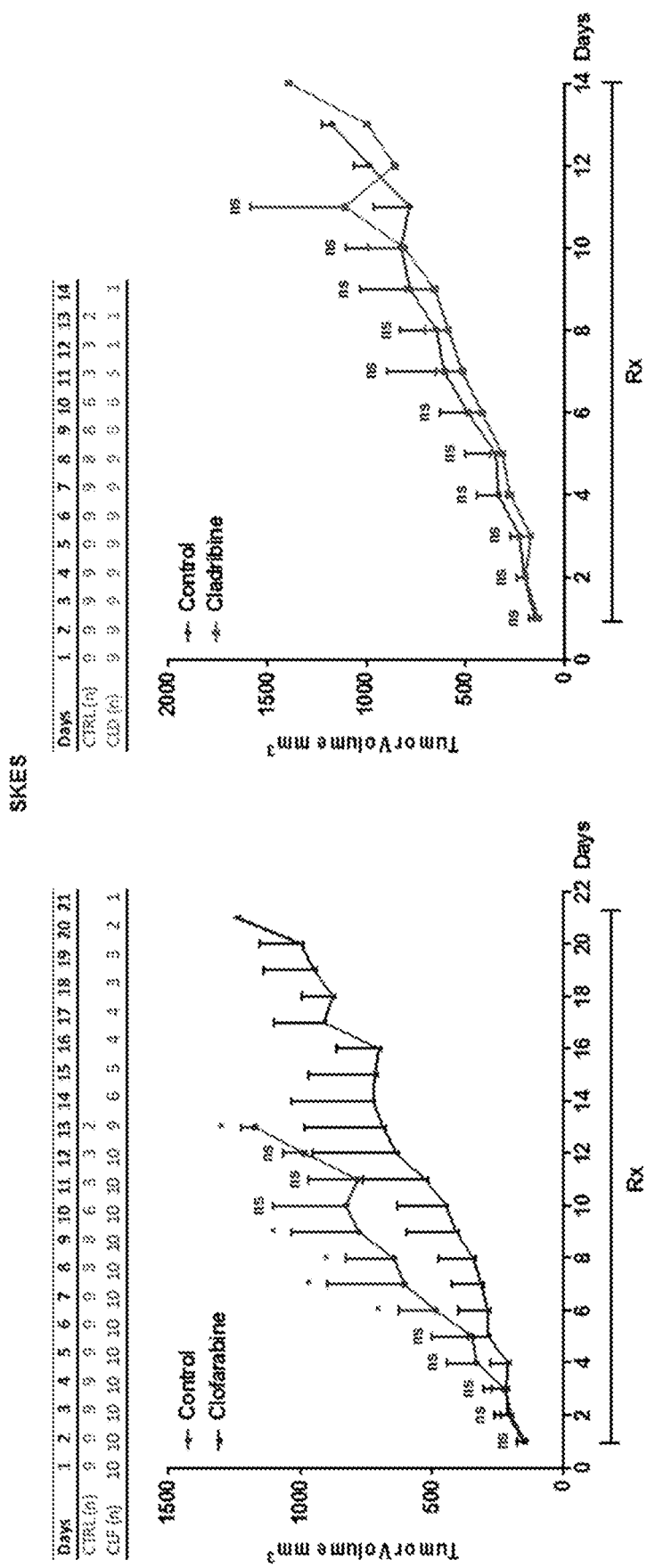
Figure 15C:
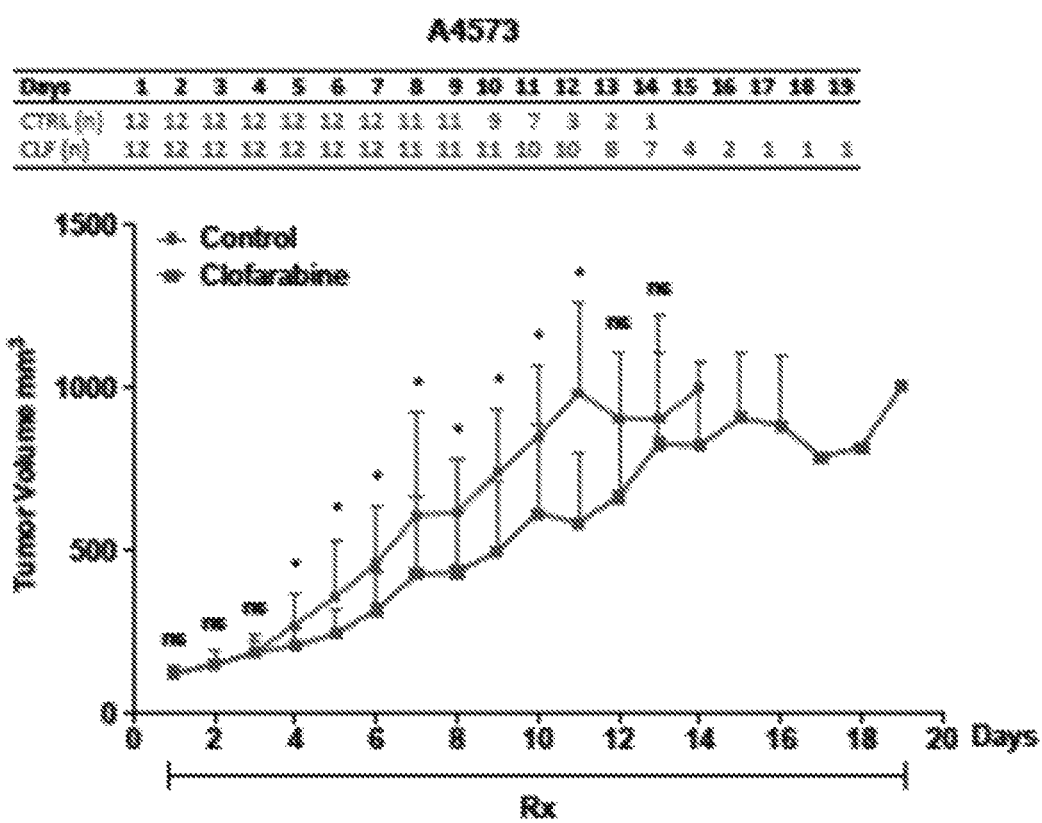

To evaluate the anti-tumor effect of clofarabine and cladribine, orthotopic ES xenografts of TC-71, SKES and A4573 cells in SCID/beige mice were established. The antitumor activity of drugs through intraperitoneal (i.p.) administration given once daily was determined. When tumor sizes reached to ≈150-200 mm³, the mice were randomly allocated into 3 treatment groups; DMSO, clofarabine and cladribine. Mice tolerated the drug treatment well. No meaningful reduction in total body weight, that was monitored daily, was observed (FIG. 13). The in vivo potencies of drug treatments were evaluated by event-free survival curves, where tumors that reached 1.0 cm³ in size considered an event. Clofarabine treatment significantly improved the event-free survival of mice in all three xenograft models, whereas the event-free survival of cladribine-treated mice was significantly different from that of the vehicle-treated group only in TC-71 xenograft model but not in SK-ES (FIGS. 14A-C). Therefore, cladribine was not used in the following A4573 xenograft study. Treatment of mice with clofarabine induced a significant inhibition of tumor growth compared to control mice in all xenograft models (FIGS. 15A-C). By contrast, cladribine was less effective, however the activity of this compound was encouraging in TC-71 xenograft model as the tumors in cladribine-treated mice grew slower than those in vehicle-treated mice (FIG. 15A). After 14 days of treatment surviving animals were monitored for tumor growth in TC-71 xenograft-bearing mice.

Figure 16:
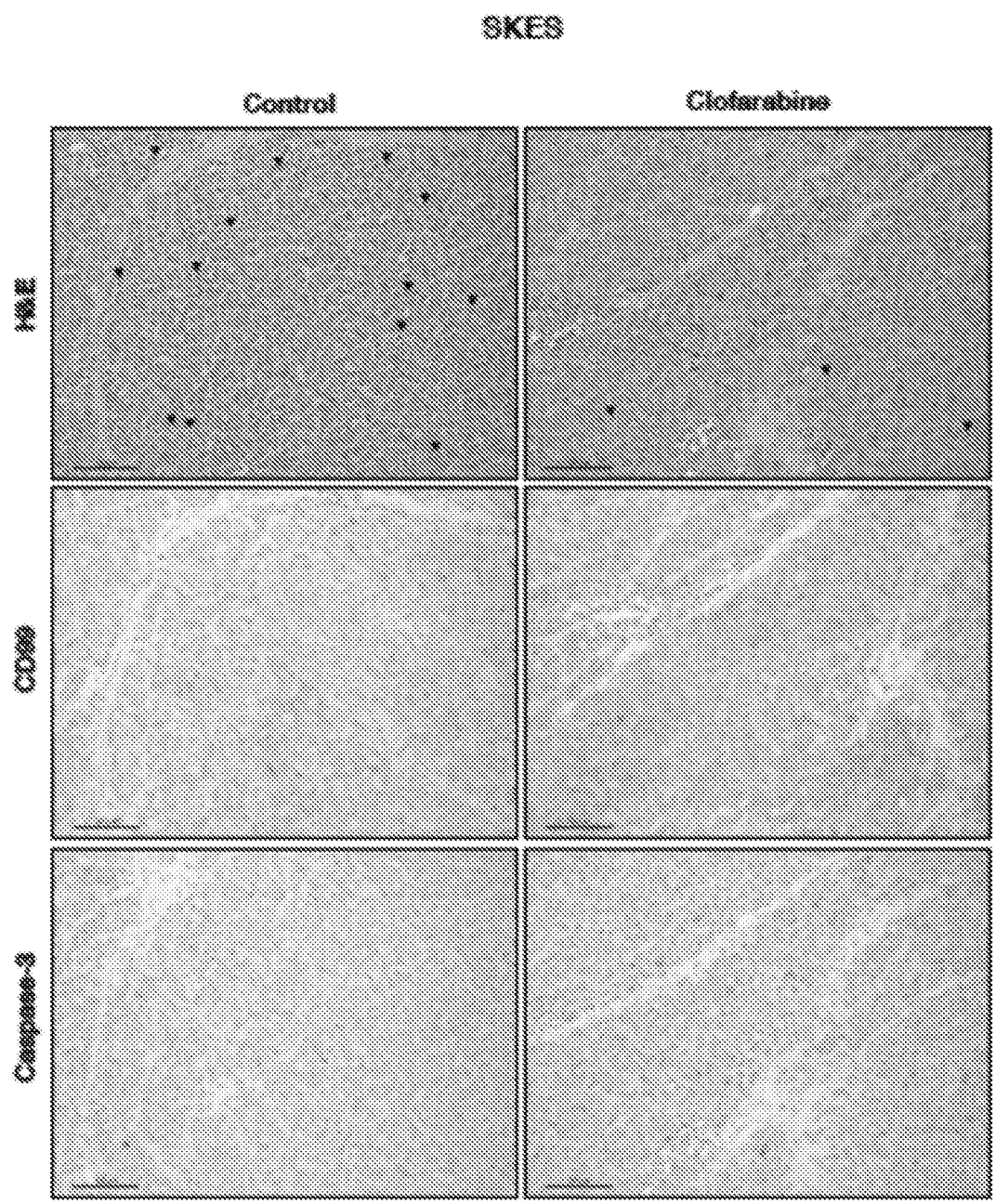
FIG. 16 is a histopathologic analysis of SKES xenografts treated with clofarabine. Representative images of SKES tumor samples collected during necropsy are provided. The column on the left contains images from DMSO control group. The column on the right contains images from the treatment group. Top row images are H&E stained, middle row images are stained for CD99 and bottom row images are stained for active caspase-3. Images are presented at 200-fold magnification. Scale bar is equal to 100 μm. Arrowheads on top row show mitotic figures.
Figure 17:
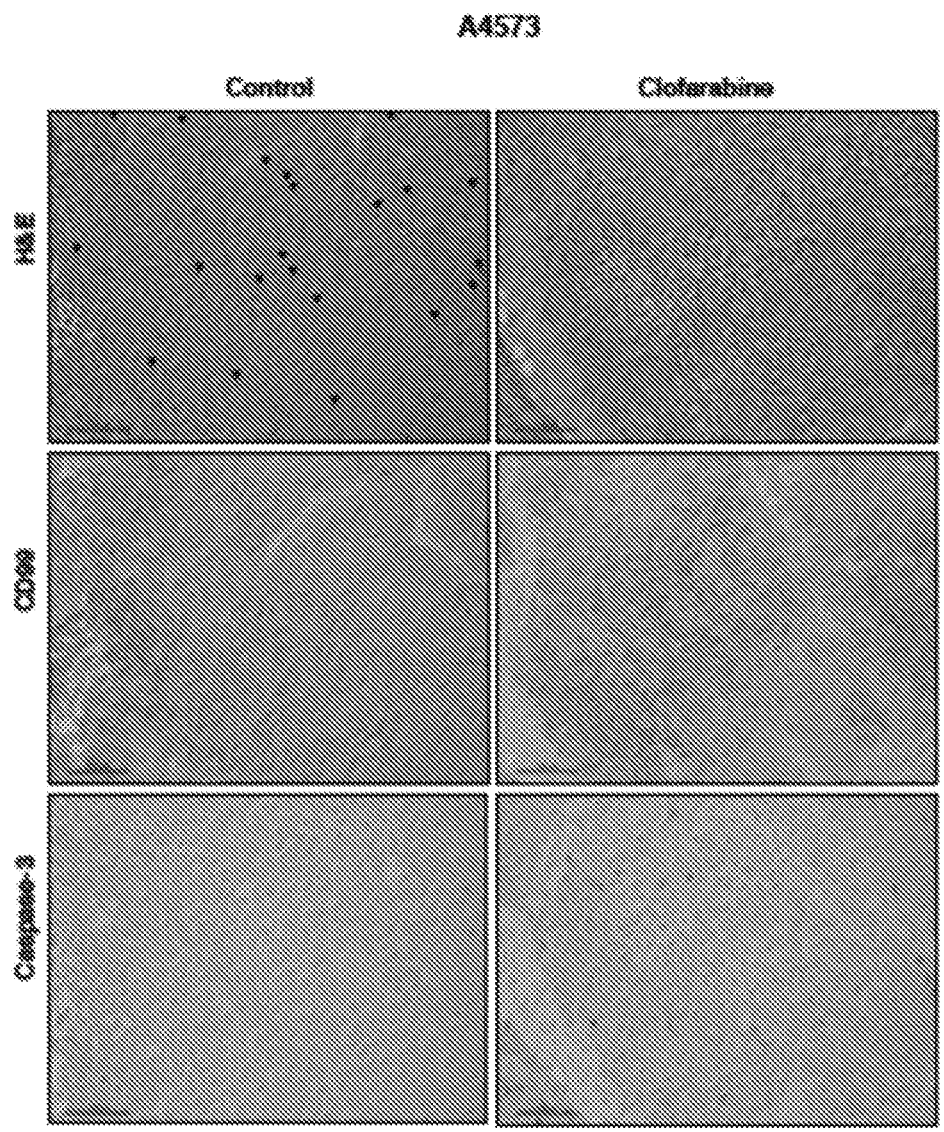
FIG. 17 is a histopathologic analysis of A4573 xenografts treated with clofarabine. Representative images of A4573 tumor samples collected during necropsy are provided. The column on the left contains images from DMSO control group. The column on the right contains images from the treatment group. Top row images are H&E stained, middle row images are stained for CD99 and bottom row images are stained for active caspase-3. Images are presented at 200-fold magnification. Scale bar is equal to 100 μm. Arrowheads on top row show mitotic figures.

Histopathological analysis of SKES and A4573 xenografts showed typical small round blue cell morphology in H&E stained samples and strong CD99 positivity in immunohistochemistry studies (FIGS. 16 and 17). No meaningful changes in CD99 expression were observed following clofarabine treatment. A4573 xenografts showed relatively stronger CD99 staining compared to SKES. In the DMSO control group, there were more than 15 mitotic figures per field in 200-fold magnification, which were reduced to 3 or less in treatment groups. There was significant increase in apoptotic cells in the treatment group that was observed in H&E slides. Increase in apoptosis was also confirmed by caspase-3 immunohistochemistry.

Figure 18A:
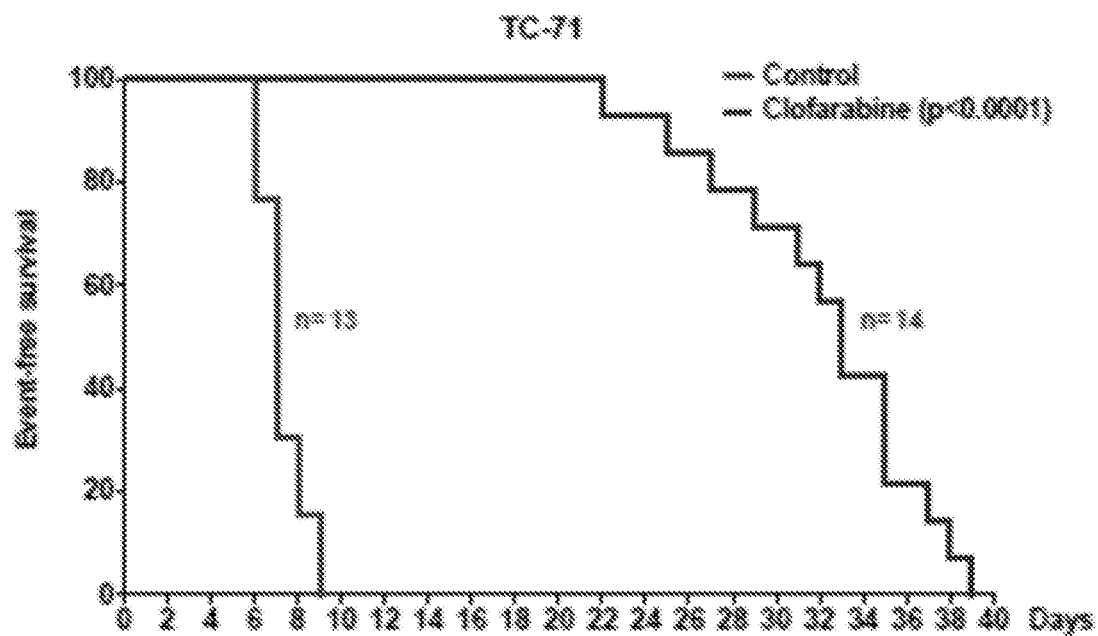
FIGS. 18A-B show that clofarabine administered orally shows potent antitumor activity in an orthotopic TC-71 xenograft mouse model of ES. SCID/beige mice bearing TC-71 xenografts were treated once daily for 14 days with vehicle or clofarabine (30 mg/kg) administered orally by gavage.
Figure 18B:
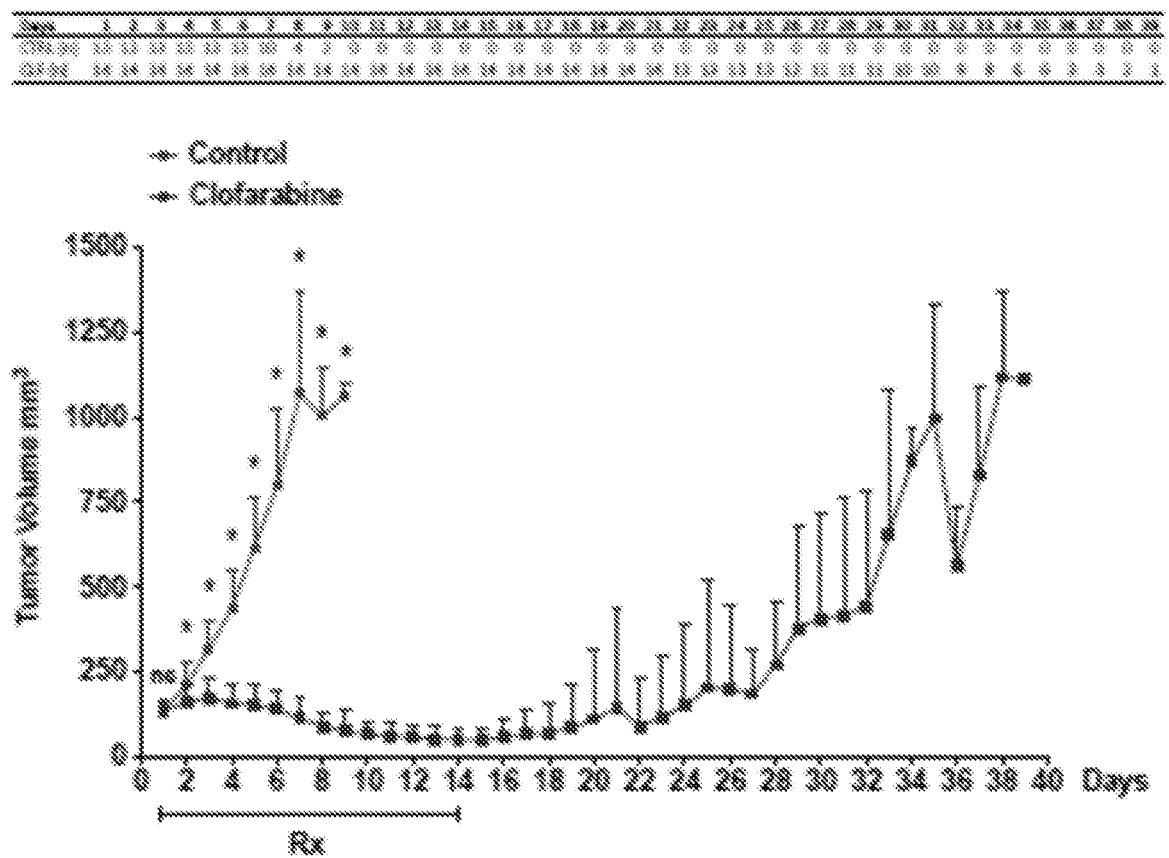
Figure 19:
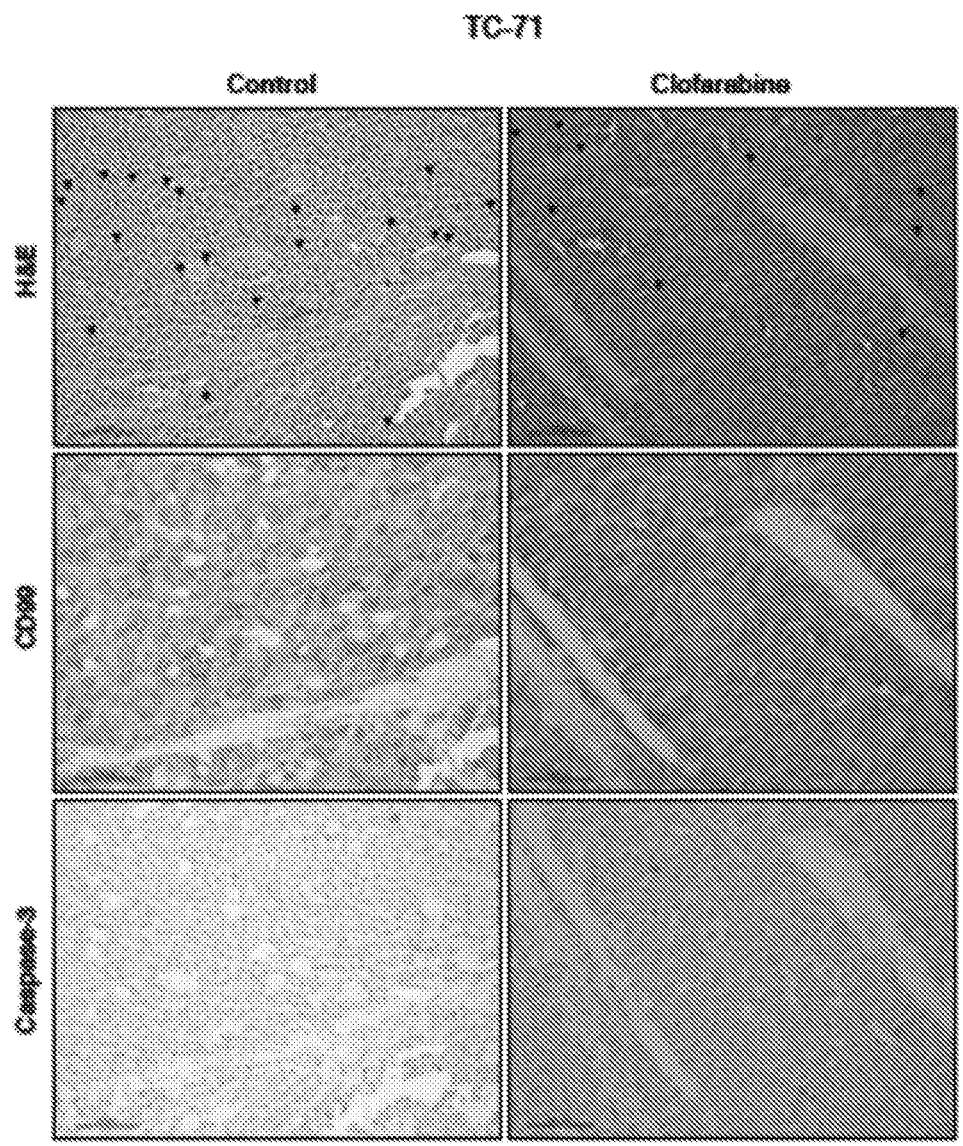
FIG. 19 is a histopathologic analysis of TC-71 xenografts treated with clofarabine (PO). Representative images of TC-71 tumor samples collected during necropsy are provided. The column on the left contains images from DMSO control group. The column on the right contains images from the treatment group. Top row images are H&E stained, middle row images are stained for CD99 and bottom row images are stained for active caspase-3. Images are presented at 200-fold magnification. Scale bar is equal to 100 μm. Arrowheads on top row show mitotic figures.

The antitumor activity of clofarabine (30 mg/kg) administered orally once daily for 14 days resulted in markedly enhanced antitumor activity compared to i.p. administration as shown by more significant inhibition of tumor growth and prolonged event-free survival (FIG. 18A-B). Clofarabine treatment significantly increased the median event-free survival from 7 to 33 days (p<0.0001) (FIG. 18A). TC-71 xenografts also showed typical small round blue cell morphology in H&E staining and CD99 staining even stronger than A4573 xenografts (FIG. 19). In this study, reduction in number of mitotic figures and increase in caspase-3 staining was less prominent. It was hypothesized that the reason for apparently reduced response to drug treatment in this group is the time of tissue harvest. In the oral study, animals responded to 14-day clofarabine treatment and they survived more than 30 days. Therefore, when the animals were euthanized for tumor regrowth they were not receiving any clofarabine. Their last dose of clofarabine was more than two week before the tissue harvest.

Figure 20:
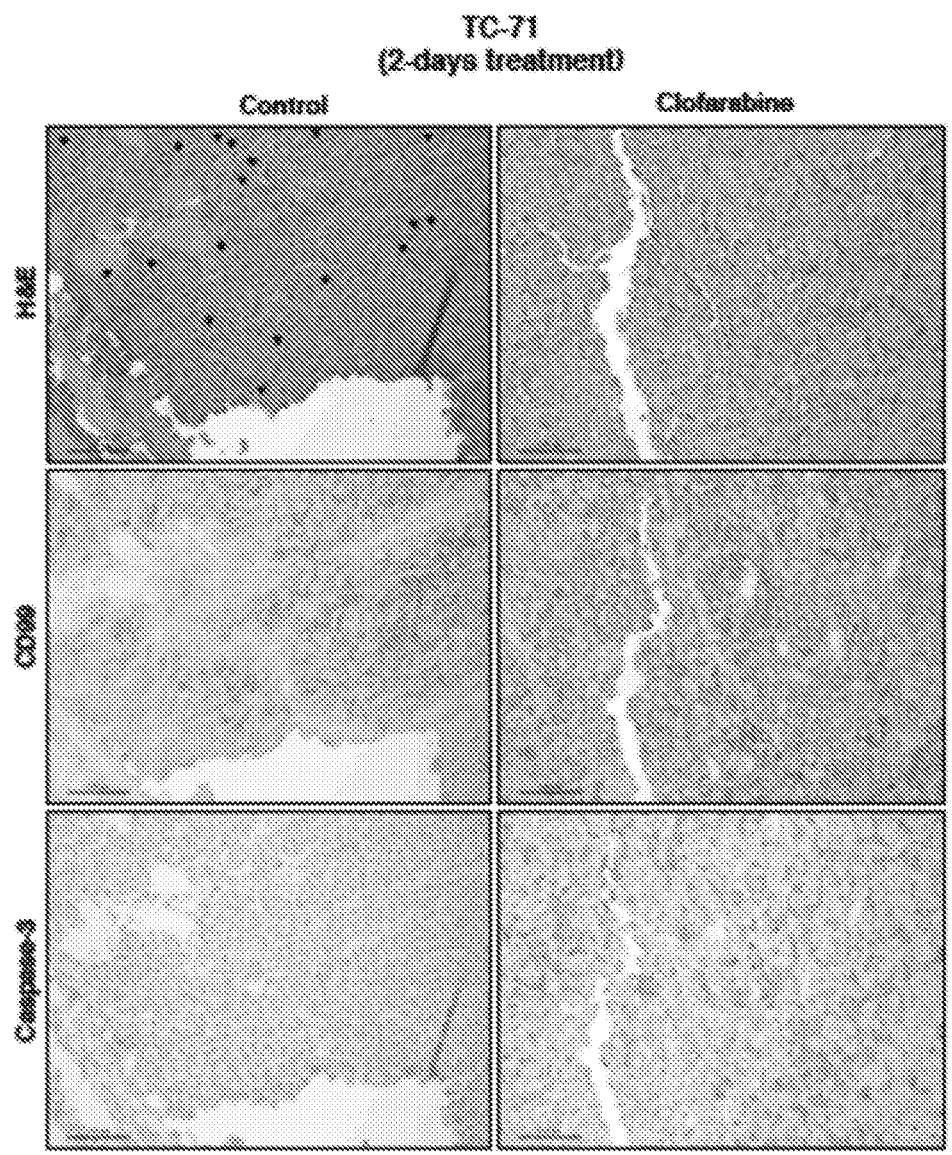
FIG. 20 is a histopathologic analysis of TC-71 xenografts following short-term (2-days) clofarabine treatment. Representative images of TC-71 tumor samples collected after two days of oral clofarabine treatment are shown. The column on the left contains images from DMSO control group. The column on the right contains images from the treatment group. Top row images are H&E stained, middle row images are stained for CD99 and bottom row images are stained for active caspase-3. Images are presented at 200-fold magnification. Scale bar is equal to 100 μm. Arrowheads on top row show mitotic figures.

In order to observe the true effect of clofarabine on TC-71 xenografts, the experiment was repeated with a smaller cohort and the animals were euthanized after 2 days of drug treatment (30 mg/kg administered orally). When the TC-71 xenografts were harvested immediately after 2 days of clofarabine treatment, complete loss of mitotic figures and a significant increase in apoptotic cells in H&E stained slides was observed, which was validated by very strong caspase-3 staining (FIG. 20).

Figure 22A:
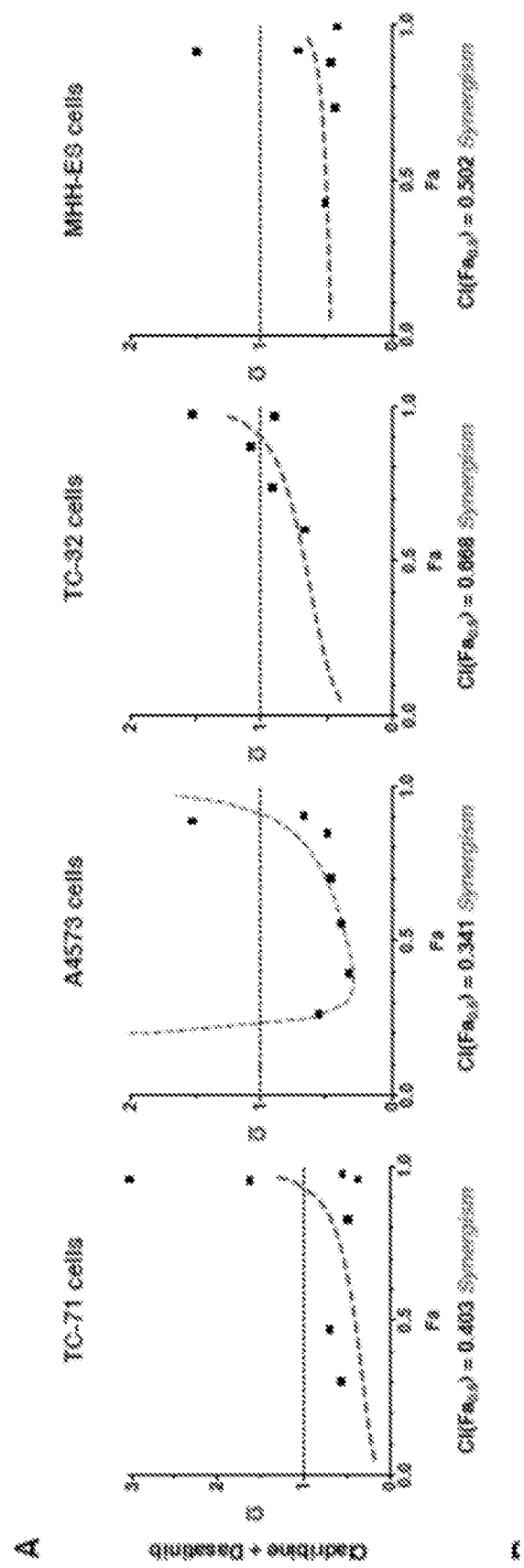
FIGS. 22A-B show that clofarabine and cladribine show synergistic cytotoxicity in combination with dasatinib in ES cells. Drug combination synergy between cladribine+dasatinib (FIG. 22A) and clofarabine+dasatinib (FIG. 22B) in TC-71, A4573, TC-32 and MHH-ES cells was analysed using the combination index (CI) from effect-oriented Fa-CI plots. Single points represent a series of dose-effect data points for each drug alone and their mixtures. Dashed line at CI=1 represents additive, CI>1 represents antagonistic and CI<1 represents synergistic effects of the drug combinations.
Figure 22B:
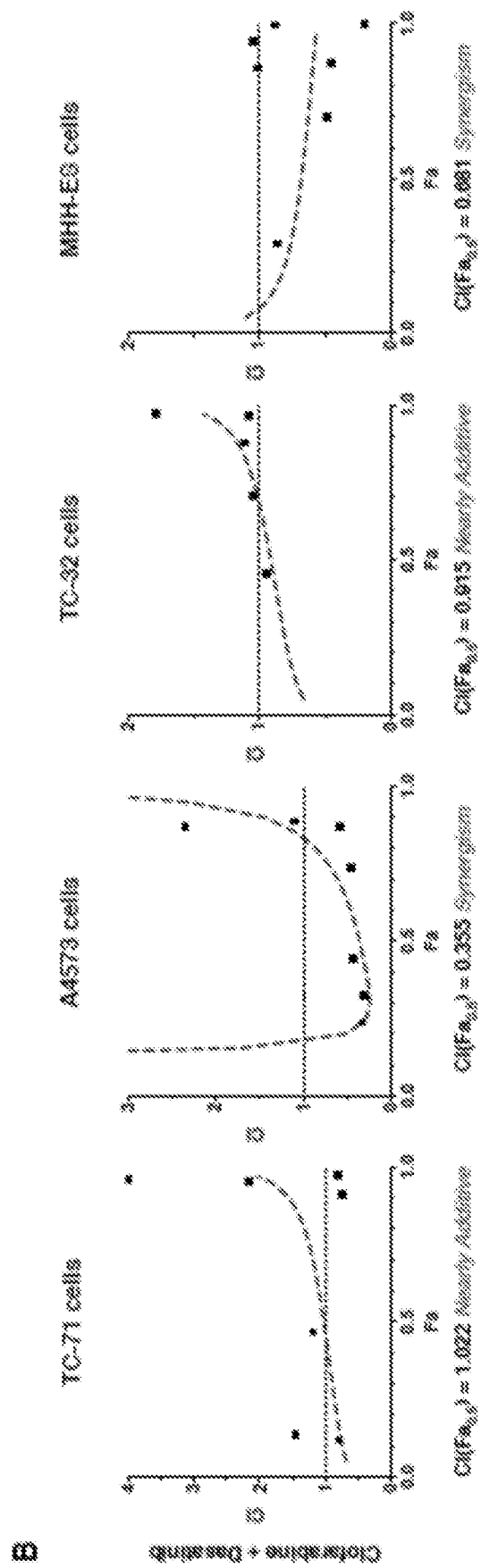

Clofarabine and Cladribine Show Synergistic Cytotoxicity When Combined with Dasatinib in ES Cells Twenty-four chemotherapeutic drugs were initially tested for a potential synergistic interaction with clofarabine on ES cells. TC-71 cells were treated with an $IC_{50}$ concentration of clofarabine alone or in combination with a sub-lethal concentration of individual drugs. From this screening, dasatinib was identified as a promising hit compound. The combination index (CI) method described by Chou and Talaly (*Adv. Enzyme Regul* 22:27-55 (1984)) was used to quantitate the drug interaction information. A synergistic interaction of cladribine and dasatinib was observed in TC-71, A4573, TC-32 and MHH-ES ES cells with combination indices between 0.34-0.67 at $F_{a0.5}$ (FIG. 22A). The combination of clofarabine and dasatinib in A4573 and MHH-ES cells also showed a synergistic interaction with CI values of 0.355 and 0.681, respectively, whereas an additive effect was displayed in TC-71 and TC-32 cell lines at $F_{a0.5}$ with CI values of 1.022 and 0.915, respectively (FIG. 22B). These data show clinical benefit arising from combination of anti-CD99 compounds with dasatinib would increase survival and reduce toxicity.

Clofarabine Activates MSK1/2

In order to gain a deeper insight into how clofarabine may regulate cellular signaling through inhibiting CD99, a Proteome Profiler Human Phosho-Kinase Array was utilized. This membrane-based sandwich immunoassay detects phosphorylation levels of 43 human kinases and kinase substrates simultaneously in the same lysate. Changes in phosphorylation were compared. The array data suggested that phosphorylation levels of 7 proteins were up- and of 2 proteins were down-regulated by both clofarabine and CD99 antibody treatment. Proteins that were regulated in the same pattern by both the CD99 antibody and clofarabine represent the most likely intracellular pathway(s) responsible for cell death due to CD99 inhibition. The most evident was the marked enhanced phosphorylation of mitogen- and stress-activated kinases 1 and 2 (MSK1/2). Four of the 7 proteins with increased phosphorylation were related to MSK1/2, which were MSK1/2 itself, its substrates CREB and c-Jun and its upstream kinase ERK1/2.

To corroborate the kinome array data, the levels of phospho-MSK1/2 in both STA-ET-7.2 and TC-32 cells treated with clofarabine were analyzed. In agreement with the array data, the phosphorylation levels of MSK1/2 were significantly elevated in cells following clofarabine treatment, relative to the cells treated with vehicle control (FIGS. 23A and 23B). To further support the finding that clofarabine leads to increased phosphorylation of MSK1/2 through inhibiting CD99, cells were treated with CD99 antibody to block its function or protein levels were depleted by using small interfering RNA duplexes. As expected, cells with inhibited CD99 function or depleted CD99 protein levels exhibited enhanced phosphorylation of MSK1/2 proteins (FIGS. 23A and 23B). In order to ascertain the tumor specificity of the drug-induced change in phosho-MSK1/2 levels, we treated both U2-OS and MG63.3 OS cells with clofarabine. Neither MG63.3 nor U2-OS cells showed a response to clofarabine treatment in terms of MSK1/2 phosphorylation (FIG. 23C).

Figure 23D:
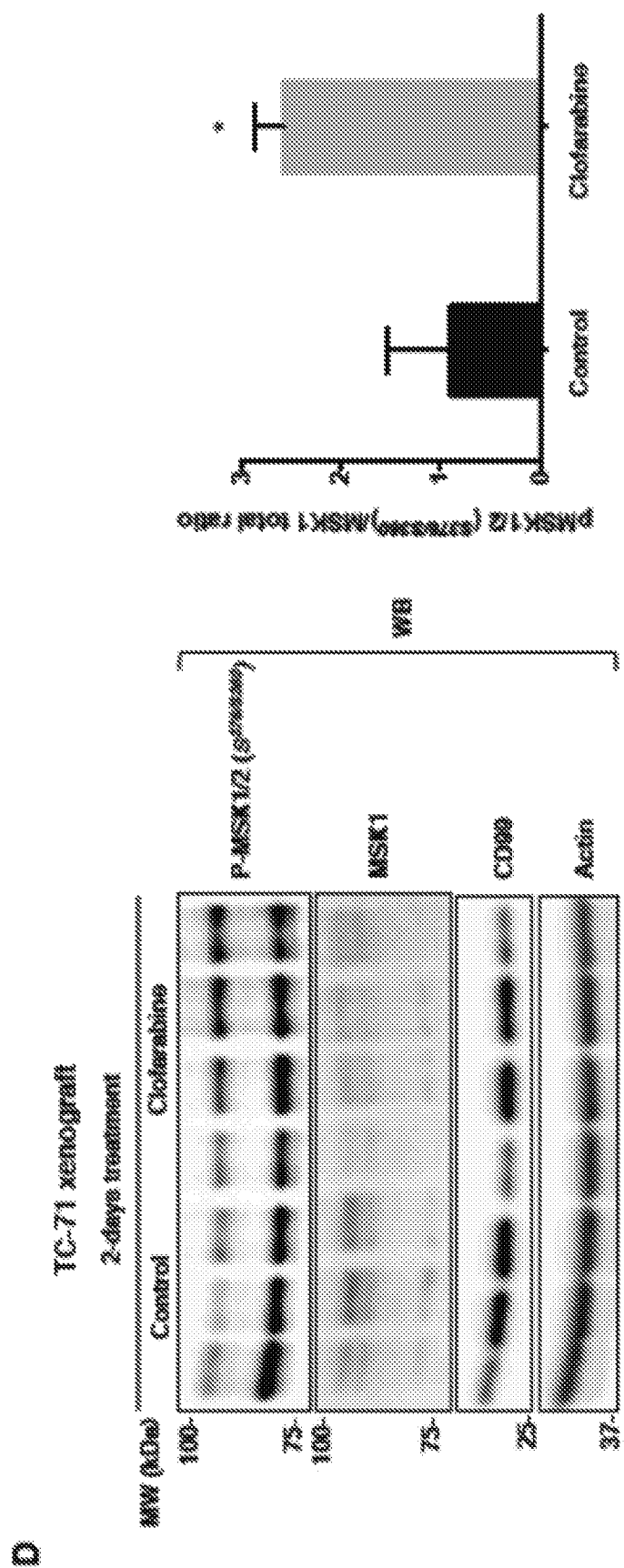

MSK1/2 was also evaluated as a potential pharmacodynamic marker for CD99 inhibitor activity. In a cohort of animals (n=3 for control group and n=4 for treatment group), TC-71 xenografts were grown to 200 mm³. Mice were then treated with oral clofarabine for two days and euthanized for tumor harvesting. Clofarabine induced a significant increase in phosphorylation levels of MSK1/2 in three out of four mice (FIG. 23D).

Clofarabine and Cladribine Kill ES vs. OS by Different Mechanisms

Figure 24:
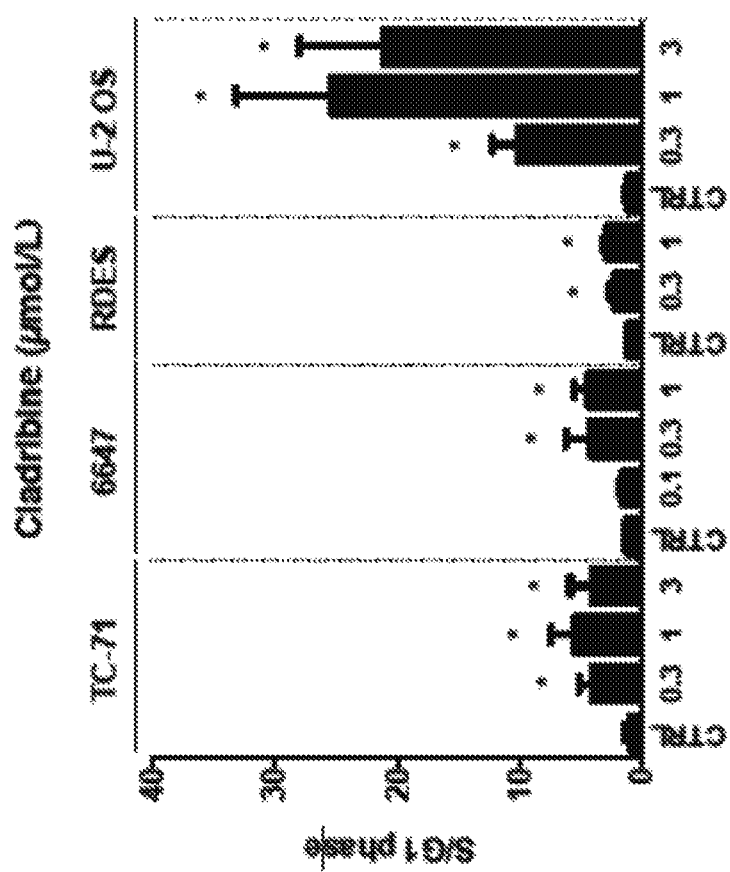
FIG. 24 shows that cladribine induces G1 arrest only in ES but not in OS cells. Cell cycle analysis was performed by flow cytometry on ES (TC-71, 6647 and RD-ES) and OS (U-2 OS) cells treated with both drugs at indicated concentrations for 48 h (doses are expressed as μmol/L). The percentage of cells incubated with drugs in the S phase significantly increased with a concomitant decrease in G1 phase in all the cell lines tested in comparison to control cells. Results shown are mean±SD of three independent experiments. Asterisks indicate statistically significant differences between treatments (*p<0.05; vs. control using a Student's unpaired t test).

Since ES cells express both DCK and CD99, clofarabine and cladribine effects on them are likely mediated by both inhibiting CD99 function and DNA synthesis. OS cells express DCK but do not express CD99. Therefore, the expected clofarabine and cladribine effect would be only inhibition of DNA synthesis without blocking CD99 related signaling. Cell cycle analysis was performed to characterize the mechanism by which clofarabine and cladribine exerts their growth-inhibitory effects in ES vs. OS cells. Treatment of TC-71, 6647 and RDES ES cells and U-2 OS cells with either clofarabine or cladribine for 48 h led to a significant increase of hypodiploid sub-G1 peak only in ES cells compared with U-2 OS cell line (FIG. 11A). Furthermore, cladribine led to a cell cycle arrest in S phase with a concomitant decrease in G1 phase in all the cells tested, however, this effect was more pronounced in OS cells compared with ES cells (FIG. 24). These observations suggest that cell cycle arrest in S phase by clofarabine and cladribine may be the result of inhibition of DNA synthesis due to their nucleoside analog activity. However, these findings also reflect a cytotoxic action of drugs in ES cells through an alternative mechanism involving CD99 rather than a cytostatic effect alone as observed in OS cells, and suggest that CD99 seems to be required for shifting the treatment response from cytostatic to cytotoxic.

These studies identified first-in-class small molecules targeting CD99 function. An innovative and stringent screening approach that combined a chemical library screening for testing direct binding ability of small molecules to the purified CD99 protein followed by a secondary cell-based cytotoxicity screening was used. This allowed identification of two FDA-approved chemotherapy drugs clofarabine and cladribine as novel inhibitors of CD99. These drugs were further characterized and validated in a variety of biochemical/molecular, cellular and in vivo assays. Clofarabine and cladribine selectively inhibited growth of cultured ES cells with $IC_{50}$ values at submicromolar ranges in comparison with non-ES cell lines and significantly suppressed the growth of tumor in xenograft models of ES.

In the animal experiments described herein, cladribine treatment was well tolerated in both experimental xenograft models. However, early deaths in clofarabine-treatment group during the treatment course in mice bearing TC-71 xenograft tumors were putatively because of higher dose-induced toxicity compared with SKES xenograft-bearing mice (30 vs. 20 mg/kg body weight). Although, survival curve for clofarabine-treatment group showed an improvement of life span in a proportion of TC-71 xenograft-bearing mice, this difference was not statistically significant due to the occurrence of early deaths. Drug-treated animals in both TC-71 and SKES xenograft models showed no evidence of body weight loss throughout the study compared with control mice.

Figure 21:
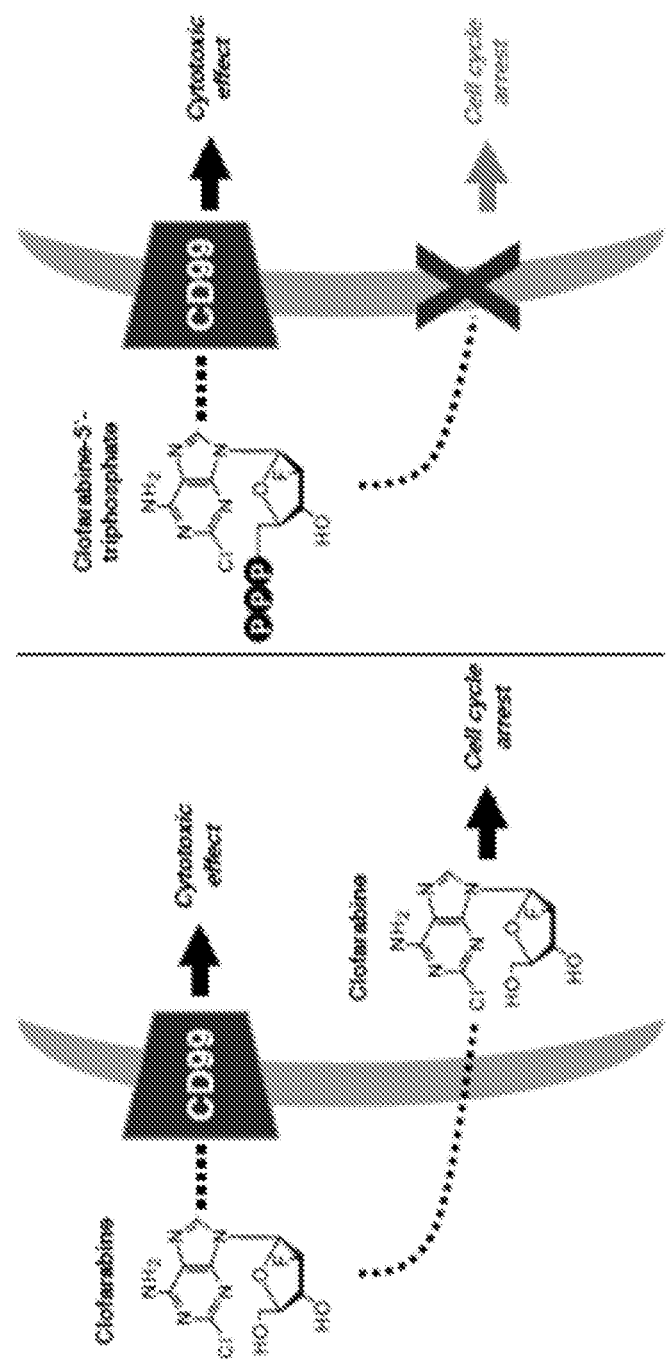
FIG. 21 shows that membrane-impermeable derivatives of clofarabine or cladribine could be more specific with reduced toxicity on normal proliferating cells. A carboxylic acid or phosphate ester derivative of clofarabine or cladribine can separate anti-CD99 activity of the molecule from its DNA-targeting effects, which may translate into high selectivity and reduced toxicity.

Because the antimetabolic effects of clofarabine and cladribine depend on their intracellular phosphorylation it was hypothesized that membrane-impermeable, carboxylic acid or phosphate ester derivatives of these drugs could be more specific in targeting CD99 with much lower toxicity on normal proliferating cells (FIG. 21). Accordingly, findings presented herein are encouraging in that clofarabine 5'-triphosphate binds with a $K_D$ value of 3.7 µmol/L and 7.6 µmol/L to the purified CD99 of mammalian and bacterial origin, respectively, and inhibits growth of ES cells with a very similar $IC_{50}$ value to that of clofarabine (FIGS. 10A-B).

In conclusion, novel small molecule inhibitors of CD99 were identified by screening small molecule libraries that bind directly to CD99 on ES cells. These molecules and membrane impermeable derivatives or analogs thereof are useful for the treatment of cancer and autoimmune disorders.

What is claimed is:

1. A method of treating a bone or connective tissue cancer in a subject in need thereof comprising administering to the subject with the bone or connective tissue cancer an effective amount of a CD99 inhibitor, wherein the bone or connective tissue cancer is a CD99+ cancer, and wherein the CD99 inhibitor is clofarabine, cladribine, a 5' triphosphate analog of clofarabine, a 5' triphosphate analog of cladribine, or pharmaceutically acceptable salts thereof.

2. The method of claim 1, wherein the CD99 inhibitor is a compound having the formula

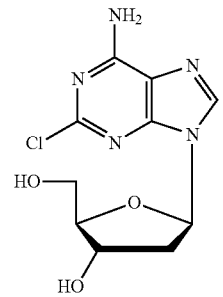

or a pharmaceutically acceptable salt thereof.

3. The method of claim 1, wherein the CD99 inhibitor is a compound having the formula

III or a pharmaceutically acceptable salt thereof.

4. The method of claim 1, wherein the analog is a compound having the formula

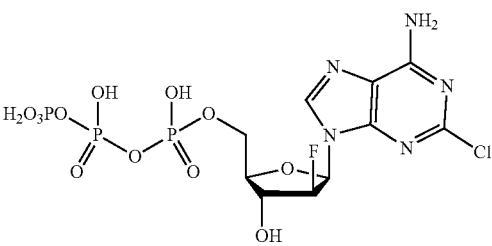

or a pharmaceutically acceptable salt thereof.

5. The method of claim 1, wherein the CD99 inhibitor is administered at a dosage of about 2 mg/kg or less.

6. The method of claim 1, wherein the inhibitor is administered systemically.

7. The method of claim 1, wherein the inhibitor is a pharmaceutical composition comprising a pharmaceutically acceptable carrier.

8. The method of claim 1, further comprising administering a tyrosine kinase inhibitor to the subject, wherein the tyroskine kinase inhibitor is dasastinib.

* * * * *